United States Patent
Ali et al.

(10) Patent No.: US 7,282,591 B2
(45) Date of Patent: Oct. 16, 2007

(54) 1H-BENZO{F}INDAZOL-5-YL DERIVATIVES AS SELECTIVE GLUCOCORTICOID RECEPTOR MODULATORS

(75) Inventors: Amjad Ali, Piscataway, NJ (US); James M. Balkovec, Martinsville, NJ (US); Donald W. Graham, Mountainside, NJ (US); Christopher F. Thompson, New York, NY (US); Nazia Quraishi, Bayonne, NJ (US)

(73) Assignee: Merck & Co., Inc., Rahway, NJ (US)

( * ) Notice: Subject to any disclaimer, the term of this patent is extended or adjusted under 35 U.S.C. 154(b) by 35 days.

(21) Appl. No.: 10/508,897

(22) PCT Filed: Apr. 8, 2003

(86) PCT No.: PCT/US03/10867

§ 371 (c)(1),
(2), (4) Date: Apr. 28, 2005

(87) PCT Pub. No.: WO03/086294

PCT Pub. Date: Oct. 23, 2003

(65) Prior Publication Data

US 2005/0256315 A1    Nov. 17, 2005

Related U.S. Application Data

(60) Provisional application No. 60/371,948, filed on Apr. 11, 2002.

(51) Int. Cl.
C07D 487/14    (2006.01)
(52) U.S. Cl. .................................... 548/359.1
(58) Field of Classification Search .............. 548/359.1
See application file for complete search history.

(56) References Cited

U.S. PATENT DOCUMENTS

| 4,349,558 A | 9/1982 | Bell |
|---|---|---|
| 4,349,559 A | 9/1982 | Bell et al. |
| 4,412,995 A | 11/1983 | Bell et al. |
| 6,506,766 B1 | 1/2003 | Coghlan et al. |
| 6,831,093 B2 * | 12/2004 | Scanlan et al. ............. 514/406 |
| 2003/0073703 A1 | 4/2003 | Coghlan et al. |
| 2003/0176478 A1 | 9/2003 | Scanlan et al. |

FOREIGN PATENT DOCUMENTS

| EP | 0 000 471 | 12/1978 |
|---|---|---|
| WO | WO99/41256 | 8/1999 |
| WO | WO02/02565 A2 | 1/2002 |
| WO | WO 03/061651 A1 | 7/2003 |

OTHER PUBLICATIONS

Scanlan et al., STN International, HCAPLUS Database, Accession No. 2003:89-6.*
Scanlan et al., STN International, HCAPLUS Database, Accession No. 2003:590999, Reg. Nos. 571202-89-6, 571202-90-9, 57120291-0, 571202-93-2, 57120294-3, 571202-95-4, 57120296-5, 571202-97-6, 571202-98-7 and 571202-99-8 (2006).*
R. Hirschmann, et al., J. Am Chem. Soc., vol. 85, p. 120, 1963.
J.H. Fried, et al., J. Am Chem. Soc., vol. 85, p. 236, 1963.
R. Hirschmann, et al., J. Am. Chem. Soc., vol. 86, p. 1520, 1964.
R. Hirschmann, et al., J. Med. Chem., vol. 7, p. 352, 1964.
Abstract of Papers of the American Chem. Soc., 2001, 221, No. 260, Shah, N.; Scanlan, T.
Bioorganic & Medicinal Chemistry Letters, vol. 14, p. 5199-5203, 2004.
A. Ali, et al., Journal of Medicinal Chemistry, vol. 47, p. 2441, 2004.
R. Newton, Thorax, vol. 55, p. 603, 2000, "Molecular mechanisms of glucocorticoid action: What is important?".

* cited by examiner

Primary Examiner—Golam M. M. Shameem
Assistant Examiner—Andrew B. Freistein
(74) Attorney, Agent, or Firm—Raynard Yuro

(57) ABSTRACT

The present invention encompasses compounds of Formula I: (I) or pharmaceutically acceptable salts or hydrates thereof, which are useful as selective glucocorticoid receptor ligands for treating a variety of autoimmune and inflammatory diseases or conditions. Pharmaceutical compositions and methods of use are also included.

2 Claims, No Drawings

1H-BENZO{F}INDAZOL-5-YL DERIVATIVES AS SELECTIVE GLUCOCORTICOID RECEPTOR MODULATORS

CROSS REFERENCE TO RELATED APPLICATIONS

This application is a U.S. National Phase application under 35 U.S.C. § 371 of PCT Application No. PCT/US03/10867, filed Apr. 8, 2003, which claims priority under 35 U.S.C. 119 to U.S. No. 60/371,948, filed Apr. 11, 2002.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor has an essential role in regulating human physiology and immune response. Steroids that interact with the glucocorticoid receptor have been shown to be potent antfinflammatory agents. The present invention is directed to a novel class of compounds that are selective glucocorticoid receptor modulators that have potent aniinflammatory and immunosupresive activity and possess advantages over steroidal glucocorticoid ligands with respect to side effects, efficacy, toxicity and/or metabolism.

SUMMARY OF THE INVENTION

The present invention encompasses compounds of Formula I:

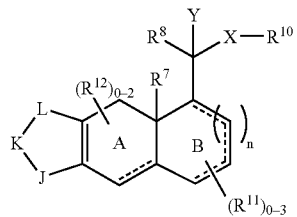

I or pharmaceutically acceptable salts or hydrates thereof, which are useful as selective glucocorticoid receptor ligands for treating a variety of autoimmune and inflammatory diseases or conditions. Pharamaceutical compositions and methods of use are also included.

DETAILED DESCRIPTION OF THE INVENTION

The present invention encompasses a compound represented by Formula I

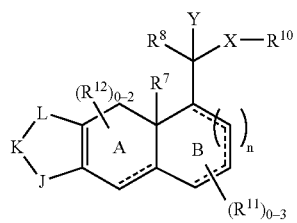

I or a pharmaceutically acceptable salt or hydrate thereof, wherein:

n is 0, 1 or 2;
J is selected from $NR^1$ or $C(R^1)(R^2)$;
K is selected from $NR^3$ or $C(R^3)(R^4)$;
L is selected from $NR^5$ or $C(R^5)(R^6)$;
X is a bond, —C(O), —N($R^{14}$)—, —N($R^{14}$)—C(O)—, or

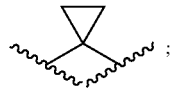

$R^1$, $R^8$ and $R^{10}$ are each independently selected from the group consisting of:
(1) $C_{1-6}$alkyl,
(2) $C_{2-6}$alkenyl,
(3) $C_{3-6}$akynyl,
(4) $C_{3-6}$cycloalkyl,
(5) $C_{1-6}$alkoxy,
(6) $C_{1-6}$alkyl-S(O)$_k$—, wherein k is 0, 1 or 2,
(7) aryl,
(8) aralkyl,
(9) HET,
(10) —$C_{1-6}$alkyl-HET,
(11) aryloxy,
(12) aroyloxy,
(13) aralkenyl,
(14) aralkynyl,
(15) hydrogen,
(16) hydroxy and
(17) $C_{1-6}$alkyl-N($R^{14}$)—S(O)$_k$—, wherein k is 0, 1 or 2, wherein items (1) to (6) above and the alkyl portions of items (8), (10) and (17) above and the alkenyl portion of item (13) above and the alkynyl portion of item (14) above are optionally substituted from one up to the maximum number of substitutable positions with a substituent independently selected from the group consisting of: halo, $OR^{13}$, $N(R^{14})_2$, $C_{3-6}$cycloalkyl, $C_{1-6}$alkyl-S(O)$_k$— and aryl-S(O)$_k$—, wherein k is 0, 1 or 2, and wherein items (7), (9), (11) and (12) above and aryl portion of items (8), (13) and (14) above and the HET portion of item (10) above are optionally substituted from one up to the maximum number of substitutable positions with a substituent independently selected from the group consisting of:
(a) halo,
(b) $OR^{13}$,
(c) $N(R^{14})_2$,
(d) $C_{1-6}$alkyl,
(e) $C_{2-6}$alkenyl,
(f) $C_{3-6}$akynyl,
(g) $C_{1-6}$alkyl-S(O)$_k$—, wherein k is 0, 1 or 2,
(h) aryl,
(i) aryl-S(O)$_k$—, wherein k is 0, 1 or 2,
(j) B ET,
(k) aralkyl,
(l) aroyl,
(m) aryloxy,
(n) aralkoxy and
(o) CN, wherein items (d) to (g) above and the alkyl portions of item (k) above are optionally substituted from one up to the maximum number of substitutable positions with a substituent independently selected from the group consisting of: halo, $OR^{13}$ and $N(R^{14})_2$, and wherein items (h), (i), (j), (l) and (m) above and the aryl portions of items (k) and (n) above are optionally substituted from one up to the maximum number of substitutable positions with a substituent independently selected from the group consisting of: halo, $OR^{13}$ and $C_{1-4}$alkyl, or when X is a bond then $R^8$ and $R^{10}$ may be joined together to form a 4- to 8-membered monocylic ring, optionally containing 1-3 heteroatoms selected from O, S and $NR^{14}$, and optionally containing 1 or 2 double bonds;

$R^2$, $R^3$, $R^4$, $R^5$ and $R^6$ are each independently selected from the group consisting of:
- (1) hydrogen,
- (2) halo,
- (3) $C_{1-6}$alkyl,
- (4) $C_{2-6}$alkenyl,
- (5) $C_{3-6}$akynyl,
- (6) $C_{3-6}$cycloalkyl,
- (7) $C_{1-6}$alkoxy,
- (8) $C_{1-6}$alkyl-$S(O)_k$—, wherein k is 0, 1 or 2,
- (9) aryl,
- (10) aralkyl,
- (11) BET and
- (12) —$C_{1-6}$alkyl-HET, wherein items (3) to (8) above and the alkyl portions of items (10) and (12) above are optionally substituted from one up to the maximum number of substitutable positions with a substituent independently selected from the group consisting of: halo, $OR^{13}$, $N(R^{14})_2$ and $C_{1-6}$alkyl-$S(O)_k$—, wherein k is 0, 1 or 2; and wherein items (9) and (11) and the aryl portion of items (10) and the HET portion of item (12) are optionally substituted from one up to the maximum number of substituable positions with a substituent independently selected from the group consisting of:
- (a) halo,
- (b) $OR^{13}$,
- (c) $N(R^{14})_2$,
- (d) $C_{1-6}$alkyl,
- (e) $C_{2-6}$alkenyl,
- (f) $C_{3-6}$akynyl and
- (g) $C_{1-6}$allyl-$S(O)_k$—, wherein k is 0, 1 or 2, wherein items (d) to (g) above are optionally substituted with from one up to the maximum number of substitutable positions with a substituent independently selected from the group consisting of: halo, $OR^{13}$ and $N(R^{14})_2$, or $R^1$ and $R^3$ or $R^3$ and $R^5$ may be joined together to form a double bond;

$R^7$ is selected from the group consisting of:
- (1) hydrogen,
- (2) $OR^{13}$,
- (3) $C_{1-4}$alkyl,
- (4) aryl and
- (5) aralkyl, wherein item (3) above and the alkyl portion of item (5) above are optionally substituted with from one up to the maximum number of substitutable positions with a substituent independently selected from the group consisting of: halo, $OR^{13}$ and $N(R^{14})_2$, and wherein item (4) above and the aryl portion of item (5) above are optionally substituted with from one up to the maximum number of substitutable positions with a substituent independently selected from the group consisting of:
- (a) halo,
- (b) $OR^{13}$,
- (c) $N(R^{14})_2$,
- (d) $C_{1-6}$alkyl,
- (e) $C_{2-6}$alkenyl and
- (f) $C_{3-6}$akynyl, wherein items (d) to (f) above are optionally substituted with from one up to the maximum number of substitutable positions with a substituent independently selected from the group consisting of: halo, $OR^{13}$ and $N(R^{14})_2$;

Y is selected from the group consisting of:
- (1) hydrogen,
- (2) —O—$R^9$,
- (3) —$S(O)_k$—$R^9$, wherein k is 0, 1 or 2,
- (4) —C—W—$R^9$, wherein W is O or $S(O)_k$,
- (5) —$N(R^{15})_2$,
- (6) —$S(O)_k$—$N(R^{15})_2$,
- (7) —$N(R^{15})$—$S(O)_k$—$N(R^{15})_2$,
- (8) $NO_2$,
- (9) —C(O)—$R^{15}$,
- (10) —C(O)O—$R^{15}$,
- (11) —CN,
- (12) halo and
- (13) —O—$S(O)_k$—$R^{15}$, $R^9$ is selected from the group consisting of: hydrogen, $C_{1-12}$alkyl and aryl, wherein $C_{1-12}$alkyl and aryl are optionally substituted from one up to the maximum number of substituents with halo, or when Y is $OR^9$ then $R^8$ and $R^9$ may be joined together to form a carbonyl group;

each $R^{11}$ and $R^{12}$ is independently selected from the group consisting of:
- (1) halo,
- (2) $C_{1-6}$alkyl,
- (3) $C_{2-6}$alkenyl,
- (4) $C_{1-6}$alkoxy and
- (5) hydroxy, wherein items (2) to (4) above are optionally substituted from one up to the maximum number of substitutable positions with a substituent independently selected from the group consisting of: halo, $OR^{12}$, $N(R^{13})_2$ and $C_{1-6}$alkyl-$S(O)_k$—, wherein k is 0, 1 or 2;

each $R^{13}$ and $R^{14}$ is independently selected from the group consisting of hydrogen, $C_{1-4}$alkyl and $C_{2-4}$alkenyl, each of said $C_{1-4}$alkyl and $C_{2-4}$alkenyl optionally substituted from one up to the maximum number of substitutable positions with a substituent independently selected from the group consisting of: halo, $C_{1-4}$alkoxy, aryl, $C_{3-6}$cycloalkyl, CN and $C_{1-4}$alkyl-$S(O)_k$, wherein k is 0, 1 or 2;

each $R^{15}$ is independently selected from the group consisting of: hydrogen, $C_{1-6}$alkyl, aryl and $C_{1-12}$alkoxycarbonyl, wherein said $C_{1-6}$alkyl and $C_{1-12}$alkoxycarbonyl are optionally substituted from one up to the maximum number of substituable positions with halo and said aryl is optionally substituted from one up to the maximum number of substituable positions with halo and $C_{1-4}$alkyl, optionally substituted with 1-3 halo groups; and HET is a 5- to 10-membered aromatic, partially aromatic or non-aromatic mono- or bicyclic ring, containing 1-4 heteroatoms selected from O, S and N, and optionally substituted with 1-2 oxo groups.

An embodiment of the invention encompasses a compound of Formula I

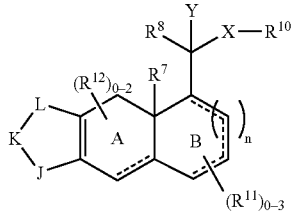

or a pharmaceutically acceptable salt or hydrate thereof, wherein:

n is 0, 1 or 2;
J is selected from $NR^1$ or $C(R^1)(R^2)$;
K is selected from $NR^3$ or $C(R^3)(R^4)$;
L is selected from $NR^5$ or $C(R^5)(R^6)$;
X is a bond, —C(O), —N($R^{14}$)—, —N($R^{14}$)—C(O)— or

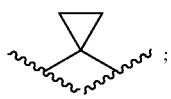

$R^1$, $R^8$ and $R^{10}$ are each independently selected from the group consisting of:
(1) $C_{1-6}$alkyl,
(2) $C_{2-6}$alkenyl,
(3) $C_{3-6}$akynyl,
(4) $C_{3-6}$cycloalkyl,
(5) $C_{1-6}$alkoxy,
(6) $C_{1-6}$alkyl-S(O)$_k$—, wherein k is 0, 1 or 2,
(7) aryl,
(8) aralkyl,
(10) —$C_{1-6}$alkyl-HET,
(11) aryloxy,
(12) aroyloxy,
(13) aralkenyl,
(14) aralkynyl,
(15) hydrogen,
(16) hydroxy and wherein items (1) to (6) above and the alkyl portions of items (8) and (10) above and the alkenyl portion of item (13) above and the alkynyl portion of item (14) above are optionally substituted from one up to the maximum number of substitutable positions with a substituent independently selected from the group consisting of: halo, $OR^{13}$, $N(R^{14})_2$, $C_{3-6}$cycloalkyl and $C_{1-6}$alkyl-S(O)$_k$—, wherein k is 0, 1 or 2, and wherein items (7), (9), (11) and (12) above and aryl portion of items (8), (13) and (14) above and the BET portion of item (10) above are optionally substituted from one up to the maximum number of substitutable positions with a substituent independently selected from the group consisting of:
(a) halo,
(b) $OR^{13}$,
(c) $N(R^{14})_2$,
(d) $C_{1-6}$alkyl,
(e) $C_{2-6}$alkenyl,
(f) $C_{3-6}$akynyl,
(g) $C_{1-6}$alkyl-S(O)$_k$—, wherein k is 0, 1 or 2, (h) aryl,
(i) aryl-S(O)$_k$—, wherein k is 0, 1 or 2,
(j) HET,
(k) aralkyl,
(l) aroyl,
(m) aryloxy,
(n) aralkoxy and
(o) CN, wherein items (d) to (g) above and the alkyl portions of item (k) above are optionally substituted from one up to the maximum number of substitutable positions with a substituent independently selected from the group consisting of: halo, $OR^{13}$ and $N(R^{14})_2$, and wherein items (h), (i), (j), (l) and (m) above and the aryl portions of items (k) and (n) above are optionally substituted from one up to the maximum number of substitutable positions with a substituent independently selected from the group consisting of: halo, $OR^{13}$ and $C_{1-4}$alkyl, or when X is a bond then $R^8$ and $R^{10}$ may be joined together to form a 4- to 8-membered monocylic ring, optionally containing 1-3 heteroatoms selected from O, S and $NR^{14}$, and optionally containing 1 or 2 double bonds;

$R^2$, $R^3$, $R^4$, $R^5$ and $R^6$ are each independently selected from the group consisting of:
(1) hydrogen,
(2) halo,
(3) $C_{1-6}$alkyl,
(4) $C_{2-6}$alkenyl,
(5) $C_{3-6}$akynyl,
(6) $C_{3-6}$cycloalkyl,
(7) $C_{1-6}$alkoxy,
(8) $C_{1-6}$alkyl-S(O)$_k$—, wherein k is 0, 1 or 2,
(9) aryl,
(10) aralkyl,
(11) HET and
(12) $C_{1-6}$alkyl-HET, wherein items (3) to (8) above and the alkyl portions of items (10) and (12) above are optionally substituted from one up to the maximum number of substitutable positions with a substituent independently selected from the group consisting of: halo, $OR^{13}$, $N(R^{14})_2$ and $C_{1-6}$alkyl-S(O)$_k$—, wherein k is 0, 1 or 2; and wherein items (9) and (11) and the aryl portion of items (10) and the HET portion of item (12) are optionally substituted from one up to the maximum number of substitutable positions with a substituent independently selected from the group consisting of:
(a) halo,
(b) $OR^{13}$,
(c) $N(R^{14})_2$,
(d) $C_{1-6}$alkyl,
(e) $C_{2-6}$alkenyl,
(f) $C_{3-6}$akynyl and
(g) $C_{1-6}$alkyl-S(O)$_k$—, wherein k is 0, 1 or 2, wherein items (d) to (g) above are optionally substituted with from one up to the maximum number of substitutable positions with a substituent independently selected from the group consisting of: halo, $OR^{13}$ and $N(R^{14})_2$, or $R^1$ and $R^3$ or $R^3$ and $R^5$ may be joined together to form a double bond;

$R^7$ is selected from the group consisting of:
(1) hydrogen,
(2) $OR^{13}$, (3) $C_{1-4}$alkyl,
(4) aryl and
(5) aralkyl, wherein item (3) above and the alkyl portion of item (5) above are optionally substituted with from one up to the maximum number of substitutable positions with a substituent independently selected from the group consisting of: halo, $OR^{13}$ and $N(R^{14})_2$, and wherein item (4) above and the aryl portion of item (5) above are optionally substituted with from one up to the maximum number of substitutable positions with a substituent independently selected from the group consisting of:
(a) halo,
(b) $OR^{13}$,
(c) $N(R^{14})_2$,
(d) $C_{1-6}$alkyl,
(e) $C_{2-6}$alkenyl and
(f) $C_{3-6}$akynyl, wherein items (d) to (f) above are optionally substituted with from one up to the maximum number of substitutable positions with a substituent independently selected from the group consisting of: halo, $OR^{13}$ and $N(R^{14})_2$;

Y is selected from the group consisting of:
(1) hydrogen,
(2) —O—$R^9$,
(3) —S(O)$_k$—$R^9$, wherein k is 0, 1 or 2,
(4) —C—W—$R^9$, wherein W is O or S(O)$_k$,
(5) —N($R^{15}$)$_2$,
(6) —S(O)$_k$—N($R^{15}$)$_2$,
(7) —N($R^{15}$)—S(O)$_k$—N($R^{15}$)$_2$,
(8) NO$_2$,
(9) —C(O)—$R^{15}$,
(10) —C(O)O—$R^{15}$,
(11) —CN,
(12) halo and
(13) —O—S(O)$_k$—$R^{15}$, $R^9$ is selected from the group consisting of: hydrogen, $C_{1-12}$alkyl and aryl, wherein $C_{1-12}$alkyl and aryl are optionally substituted from one up to the maximum number of substituents with halo, or when Y is $OR^9$ then $R^8$ and $R^9$ may be joined together to form a carbonyl group;

each $R^{11}$ and $R^{12}$ is independently selected from the group consisting of:
(1) halo,
(2) $C_{1-6}$alkyl,
(3) $C_{2-6}$alkenyl,
(4) $C_{1-6}$alkoxy and
(5) hydroxy, wherein items (2) to (4) above are optionally substituted from one up to the maximum number of substitutable positions with a substituent independently selected from the group consisting of: halo, $OR^{12}$, $N(R^{13})_2$ and $C_{1-6}$alkyl-S(O)$_k$—, wherein k is 0, 1 or 2;

each $R^{13}$ and $R^{14}$ is independently selected from the group consisting of hydrogen and $C_{1-4}$alkyl, optionally substituted from one up to the maximum number of substitutable positions with halo; and each $R^{15}$ is independently selected from the group consisting of: hydrogen, $C_{1-6}$alkyl, aryl and $C_{1-12}$alkoxycarbonyl, wherein said $C_{1-6}$alkyl and $C_{1-12}$alkoxycarbonyl are optionally substituted from one up to the maximum number of substitutable positions with halo and said aryl is optionally substituted from one up to the maximum number of substituable positions with halo and $C_{1-4}$alkyl, optionally substituted with 1-3 halo groups.

The optional double bond shown in ring A of the compound of Formula I is depicted as a dotted line and means that the double bond may or may not be present as shown below:

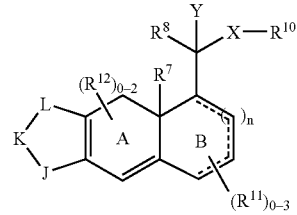

optional double bond is present in ring A

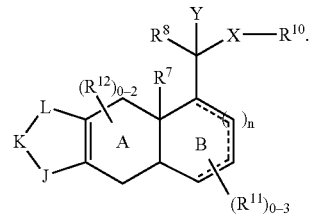

optional double bond is not present in ring A

The substituent $R^{12}$ in Formula I may or may not be present. When present, one or two $R^{12}$ groups may occupy the following positions:

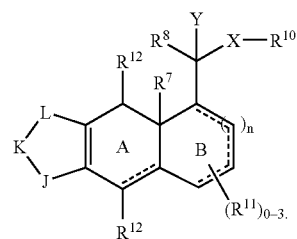

Two $R^{12}$ groups may reside on the same carbon atom.

The substituent $R^{11}$ in Formula I may or may not be present. When present, one, two or three $R^{11}$ groups may occupy the following positions:

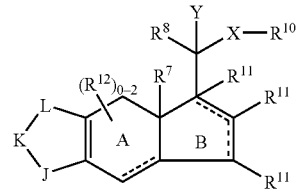

n = 0

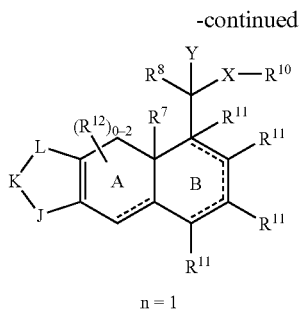
n = 1
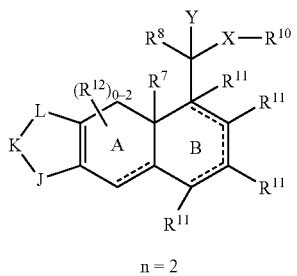
n = 2
Two R$^{11}$ groups may reside on the same carbon atom.
The optional double bonds show in ring B of the compound of Formula I may occupy the following positions:
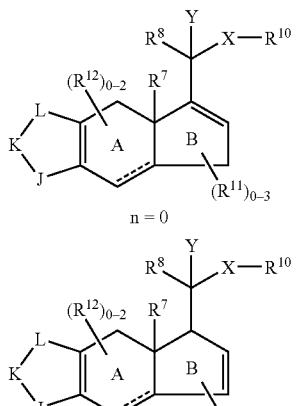
n = 0
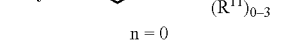
n = 0
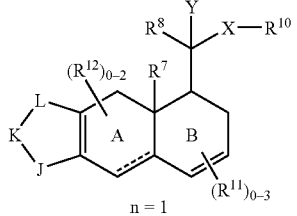
n = 1
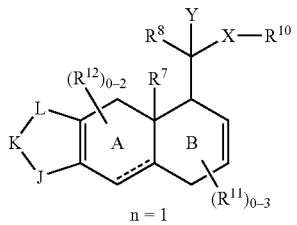
n = 1
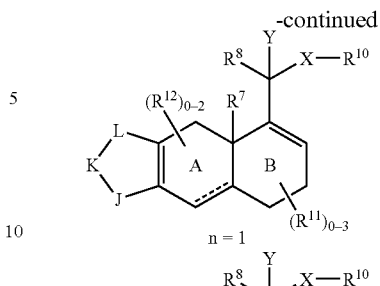
n = 1
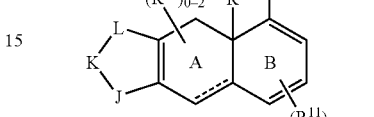
n = 1
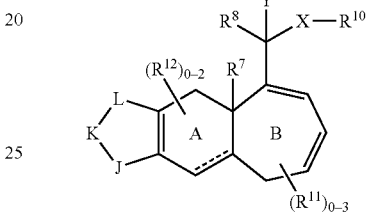
n = 2
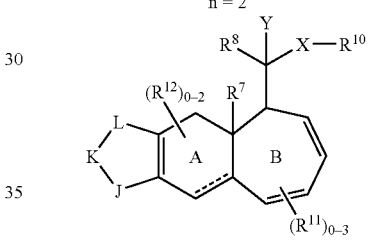
n = 2
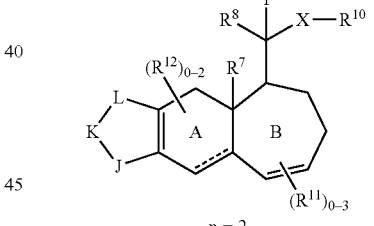
n = 2
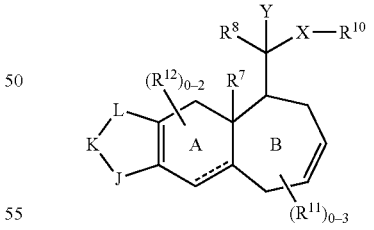
n = 2
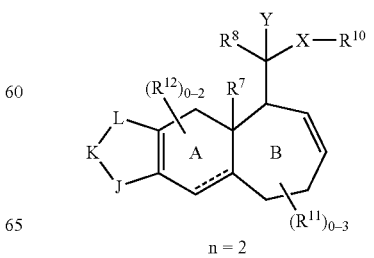
n = 2

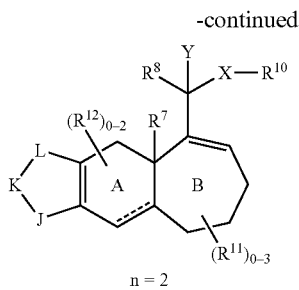
n = 2
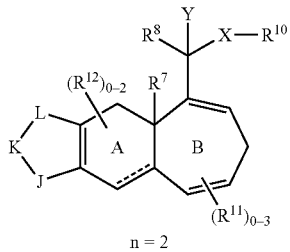
n = 2
J, K and L as defined in Formula I mean, for example, the following structures:
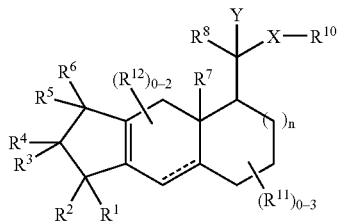
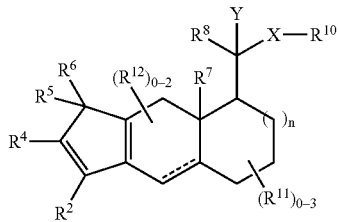
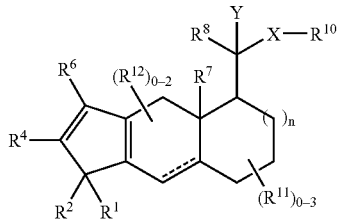
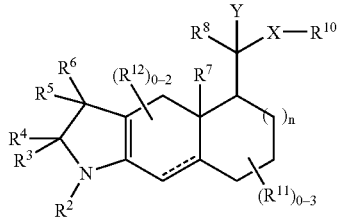
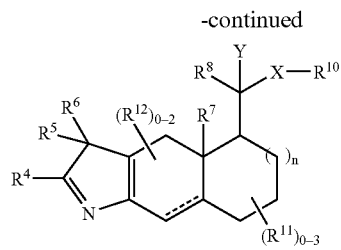
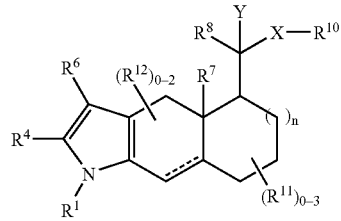
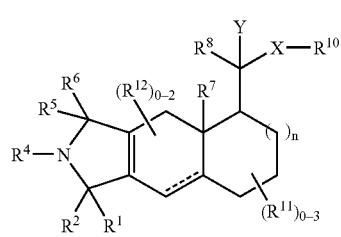
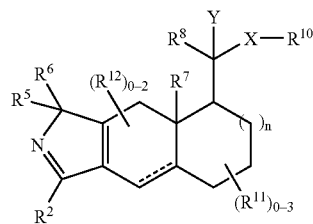
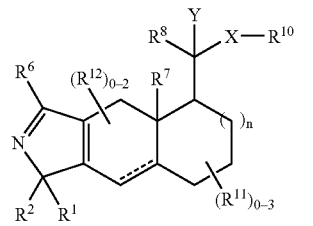
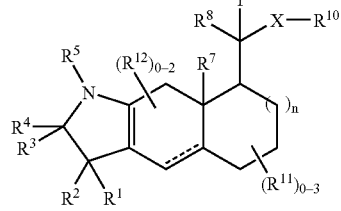
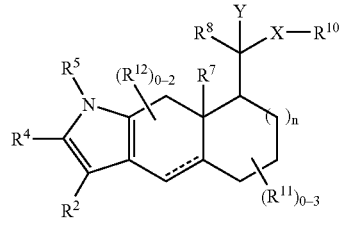

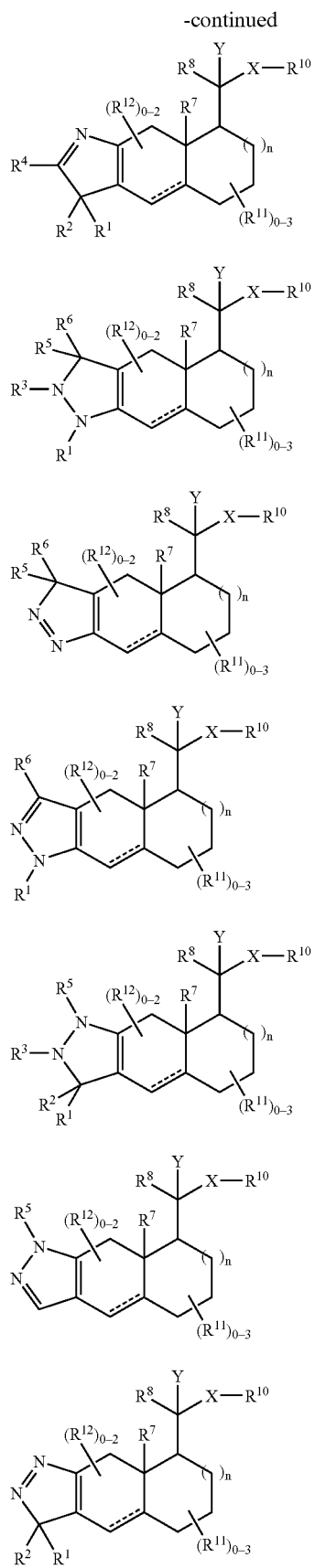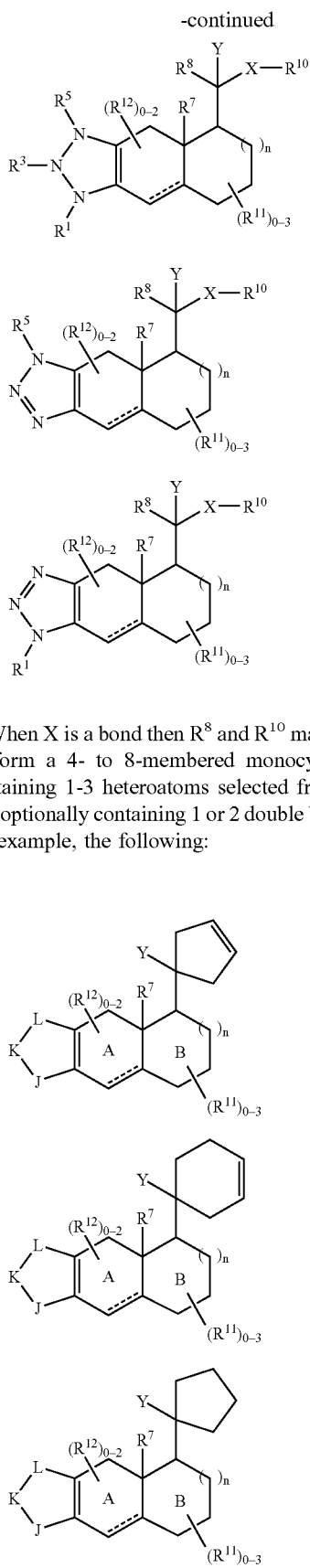
When X is a bond then $R^8$ and $R^{10}$ may be joined together to form a 4- to 8-membered monocylic ring, optionally containing 1-3 heteroatoms selected from O, S and $NR^{14}$, and optionally containing 1 or 2 double bonds, which means, for example, the following:

-continued

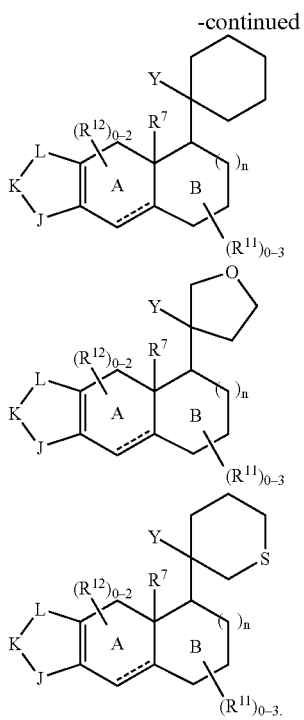

These compounds can be made, for example, by following the procedures outlined in J. Am. Chem. Soc., vol. 118, 100-110, 1996 and J. Am. Chem Soc., vol. 115, p. 9856-9924, 1993, which are hereby incorporated by reference in their entirety.

When Y is $OR^9$ then $R^8$ and $R^9$ may be joined together to form a carbonyl group, which means the following:

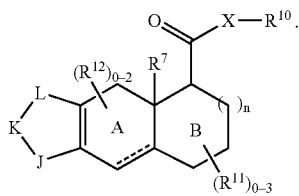

When X is $-N(R^{14})-C(O)-$ the group is attached as follows:

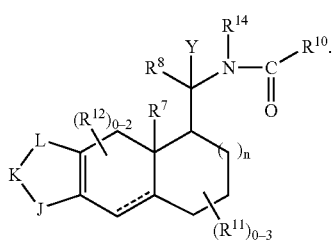

Another embodiment of the invention encompasses a compound of Formula I wherein:
J is $NR^1$;
K is $NR^3$;
L is $C(R^5)(R^6)$; and
$R^3$ and $R^5$ are joined together to form a double bond.

Another embodiment of the invention encompasses a compound of Formula I wherein the optional double bond shown in ring A of the compound of Formula I is present.

Another embodiment of the invention encompasses a compound of Formula I wherein $R^1$ is aryl or BET, said aryl or HET optionally substituted from one up to the maximum number of substitutable positions with a substituent independently selected from the group consisting of:
 (a) halo,
 (b) $OR^{13}$,
 (c) $N(R^{14})_2$,
 (d) $C_{1-6}$alkyl,
 (e) $C_{2-6}$alkenyl,
 (f) $C_{3-6}$akynyl,
 (g) $C_{1-6}$alkyl-$S(O)_k-$, wherein k is 0, 1 or 2,
 (h) aryl,
 (i) aryl-$S(O)_k-$, wherein k is 0, 1 or 2,
 (k) aralkyl,
 (l) aroyl,
 (m) aryloxy,
 (n) aralkoxy and
 (o) CN, wherein items (d) to (g) above and the alkyl portions of item (k) are optionally substituted from one up to the maximum number of substitutable positions with a substituent independently selected from the group consisting of: halo, $OR^{13}$ and $N(R^{14})_2$, and wherein items (h), (i), (j), (l) and (m) above and the aryl portions of items (k) and (n) above are optionally substituted from one up to the maximum number of substitutable positions with a substituent independently selected from the group consisting of: halo, $OR^{13}$ and $C_{1-4}$alkyl.

Within this embodiment of the invention is encompassed a compound of Formula I wherein $R^1$ is phenyl, optionally substituted with 1-3 halo groups.

Another embodiment of the invention encompasses a compound of Formula I wherein Y is $OR^9$. Within this embodiment of the invention is encompassed a compound of Formula I wherein $R^9$ is hydrogen.

Another embodiment of the invention encompasses a compound of Formula I wherein $R^7$ is methyl.

Another embodiment of the invention encompasses a compound of Formula I wherein $R^8$ is hydrogen or methyl.

Another embodiment of the invention encompasses a compound of Formula I wherein X is a bond.

Another embodiment of the invention encompasses a compound of Formula I wherein $R^{10}$ is selected from the group consisting of:
 (1) $C_{1-6}$alkyl,
 (2) $C_{2-6}$alkenyl,
 (3) $C_{3-6}$akynyl,
 (4) $C_{3-6}$cycloalkyl,
 (5) $C_{1-6}$alkoxy,
 (6) $C_{1-6}$alkyl-$S(O)_k-$, wherein k is 0, 1 or 2, wherein items (1) to (6) above are optionally substituted from one up to the maximum number of substitutable positions with a substituent independently selected from the group consisting of: halo, $OR^{13}$, $N(R^{14})_2$, $C_{3-6}$cycloalkyl and $C_{1-6}$alkyl-$S(O)_k$, wherein k is 0, 1 or 2.

Another embodiment of the invention encompasses a compound of Formula I wherein $R^{10}$ is selected from the group consisting of:
 (1) phenyl
 (2) naphthyl,
 (3) benzyl, (4) phenethyl,
(5) phenoxy,
(6) benzoyl and
(7) benzoyloxy, wherein the aryl portions of items (1) to (7) above are optionally substituted from one up to the maximum number of substitutable positions with a substituent independently selected from the group consisting of:
(a) halo,
(b) $OR^{13}$,
(c) $N(R^{14})_2$,
(d) $C_{1-6}$alkyl,
(e) $C_{2-6}$alkenyl,
(f) $C_{3-6}$akynyl,
(g) $C_{1-6}$alkyl-S(O)$_k$—, wherein k is 0, 1 or 2,
(h) aryl,
(i) aryl-S(O)$_k$—, wherein k is 0, 1 or 2,
(j) HET,
(k) aralkyl,
(l) aroyl,
(m) aryloxy,
(n) aralkoxy and
(o) CN, wherein items (d) to (g) above and the alkyl portions of item (k) are optionally substituted from one up to the maximum number of substitutable positions with a substituent independently selected from the group consisting of: halo, $OR^{13}$ and $N(R^{14})_2$, and wherein items (h), (i), (j), (l) and (m) above and the aryl portions of items (k) and (n) above are optionally substituted from one up to the maximum number of substitutable positions with a substituent independently selected from the group consisting of: halo, $OR^{13}$ and $C_{1-4}$alkyl.

Another embodiment of the invention encompasses a compound of Formula I wherein $R^{10}$ is BET or —$C_{1-4}$alkyl-BET wherein HET is selected from the group consisting of:
(1) pyridine,
(2) thiophene and
(3) furan, or benzofused analogs of (1) to (3) above.

Another embodiment of the invention encompasses a compound of Formula II:

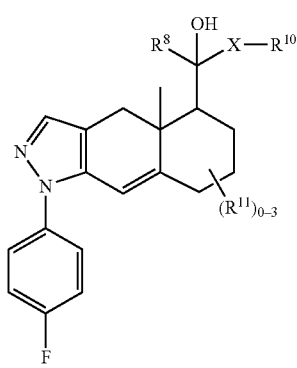

II or a pharmaceutically acceptable salt or hydrate thereof, wherein:
X is a bond;

$R^8$ and $R^{10}$ are each independently selected from the group consisting of:
(1) $C_{1-6}$alkyl, optionally substituted with hydroxy,
(2) $C_{2-6}$alkenyl,
(3) $C_{3-6}$akynyl,
(4) $C_{3-6}$cycloalkyl,
(5) phenyl
(6) naphthyl,
(7) benzyl,
(8) phenethyl and
(9) pyridine, thiophene or furan, or benzofused analogs thereof, and $R^8$ is additionally selected from hydrogen, wherein items (5), (6) and (9) above and aryl portion of items (7) and (8) above and are optionally substituted from one up to the maximum number of substitutable positions with a substituent independently selected from the group consisting of:
(a) halo,
(b) hydroxy,
(c) methoxy,
(d) $C_{1-4}$alkyl,
(e) trifluoromethyl,
(f) phenoxy,
(g) benzyloxy, optionally substituted with methoxy, and
(h) CN;

each $R^{11}$ is independently selected from the group consisting of:
(1) halo,
(2) methyl and
(3) hydroxy; and $R^{14}$ is independently selected from the group consisting of hydrogen and $C_{1-4}$alkyl.

Another embodiment of the invention encompasses a compound of Formula II wherein $R^8$ is selected from the group consisting of hydrogen or $C_{1-4}$alkyl.

Another embodiment of the invention encompasses a compound of Formula III:

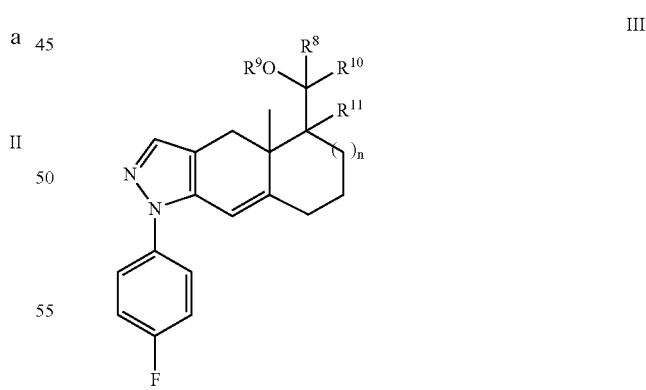

III or a pharmaceutically acceptable salt or hydrate thereof, wherein:
n is 0 or 1,
$R^8$ is hydrogen or methyl,
$R^9$ is hydrogen or methyl or
$R^8$ and $R^9$ may be joined together with the oxygen atom shown in Formula III to form a carbonyl group;

$R^{10}$ is selected from the group consisting of:
  (1) phenyl,
  (2) naphthyl,
  (3) pyridyl,
  (4) furyl or benzofuryl,
  (5) thienyl or benzothienyl, or the S,S-dioxide thereof,
  (6) benzyl,
  (7) quinoline,
  (8) thiazolyl or benzothiazolyl, and
  (9) phenylsulfonylmethyl or phenylsulfonylethyl, wherein groups (1) to (9) are optionally substituted with 1 to 3 substituents independently selected from the group consisting of:
  (a) halo,
  (b) trifluoromethyl,
  (c) trifluoromethoxy,
  (d) —N($R^{14}$), wherein each $R^{14}$ is indepedently hydrogen or $C_{1-4}$alkyl,
  (e) pyrrolyl,
  (f) methoxy, ethoxy or isopropoxy, each optionally substituted with a substituent selected from: methoxy, benzyl, cyclopropylmethyl, cyano, methylthio, methylsulfinyl and methylsulfonyl,
  (g) methyl,
  (h) vinyl and
  (i) hydroxy, and
$R^{11}$ is hydrogen or halo.

Another embodiment of the invention encompasses a compound of Formula IV:

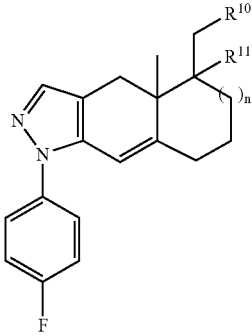

IV or a pharmaceutically acceptable salt or hydrate thereof, wherein:
n is 0 or 1,
$R^{10}$ is selected from the group consisting of:
  (1) —CH($OR^{13}$)-aryl, wherein aryl is phenyl or napthyl,
  (2) —CH($OR^{13}$)-HET, and
  (3) —CH($OR^{13}$)-$C_{1-4}$alkyl or CH($OR^{13}$)—$C_{2-4}$alkenyl, said —CH($OR^{13}$)—$C_{1-4}$alkyl or —CH($OR^{13}$)—$C_{2-4}$alkenyl optionally substituted with phenylsulfonyl,
$R^{13}$ is hydrogen or methyl,
HET is selected from the group consisting of:
  (1) pyridyl,
  (2) furyl or benzofuryl,
  (3) thienyl or benzothienyl, or the S,S-dioxide thereof,
  (4) benzyl,
  (5) quinoline,
  (6) thiazolyl or benzothiazolyl, said aryl or HET are optionally substituted with 1 to 3 substituents independently selected from the group consisting of:
  (a) halo,
  (b) trifluoromethyl,
  (c) trifluoromethoxy,
  (d) —N($R^{14}$), wherein each $R^{14}$ is indepedently hydrogen or $C_{1-4}$alkyl,
  (e) pyrrolyl,
  (f) methoxy, ethoxy or isopropoxy, each optionally substituted with a substituent selected from: methoxy, benzyl, cyclopropylmethyl, cyano, methylthio, methylsulfinyl and methylsulfonyl,
  (g) methyl,
  (h) vinyl and
  (i) hydroxy, and
$R^{11}$ is hydrogen or halo.

Another embodiment of the invention encompasses a pharmaceutical composition comprising a compound of Formula I in combination with a pharmaceutically acceptable carrier.

Another embodiment of the invention encompasses a method for treating a glucocorticoid receptor mediated disease or condition in a mammalian patient in need of such treatment comprising administering the patient a compound of Formula I in an amount that is effective for treating the glucocorticoid receptor mediated disease or condition.

Within this embodiment is encompassed the above method wherein the glucocorticoid receptor mediated disease or condition is selected from the group consisting of: tissue rejection, leukemias, lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity, metabolic syndrome, inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, cirrhosis, inflammatory scalp alopecia, panniculitis, psoriasis, discoid lupus erythematosus, inflamed cysts, atopic dermatitis, pyoderma gangrenosum, pemphigus vulgaris, buflous pemphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma, Human Immunodeficiency Virus (HIV), cell apoptosis, cancer, Kaposi's sarcoma, retinitis pigmentosa, cognitive performance, memory and learning enhancement, depression, addiction, mood disorders, chronic fatigue syndrome, schizophrenia, sleep disorders, and anxiety.

Another embodiment of the invention encompasses a method of selectively modulating the activation, repression, agonism and antagonism effects of the glucocorticoid receptor in a mammal comprising administering to the mammal a compound of Formula I in an amount that is effective to modulate the glucocorticoid receptor.

The invention is exemplified by the compounds that follow.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_1$-$C_6$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes, propenyl, 1-methylethenyl, butenyl and the like.

The term "cycloalkyl" means mono-, bi- or tricyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by an sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET" is defined as a 5- to 10-membered aromatic, partially aromatic or non-aromatic mono- or bicyclic ring, containing 1-4 heteroatoms selected from O, S and N, and optionally substituted with 1-2 oxo groups. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or HET is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

For all of the above definitions, each reference to a group is independent of all other references to the same group when referred to in the Specification. For example, if both $R^1$ and $R^2$ are HET, the definitions of HET are independent of each other and $R^1$ and $R^2$ may be different HET groups, for example furan and thiophene.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:
AIBN=2,2'-azobisisobutyronitrile
B.P.=benzoyl peroxide
Bn=benzyl
$CCl_4$=carbon tetrachloride
D=—O(CH$_2$)$_3$O—
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMW=N,N-dimethylformamide
DMSO=dimethyl sulfoxide
Et$_3$N=triethylamine
LDA=lithium diisopropylamide
m-CPBA=metachloroperbenzoic acid NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^s$=—CH$_2$SCH$_2$CH$_2$Ph
r.t.=room temperature
rac.=racemic
THF=tetrahydrofuran
THP=tetrahydropyran-2-yl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of glucocorticoid receptor mediated diseases the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

The ability of the compounds of Formula I to selectively modulate glucocorticoid receptors makes them useful for treating, preventing or reversing the progression of a variety of inflammatory and autoimmune diseases and conditions. Thus, the compounds of the present invention are useful to treat, prevent or ameliorate the following diseases or conditions: inflammation, tissue rejection, auto-immunity, various malianancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, IPA axis suppression and regulation, hypercortisolernia, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, obesity and metabolic syndrome.

The compounds of the present invention are also useful for treating, preventing or reversing the progression of disease states involving systemic inflammation such as inflammatory bowel disease, systemic lupus erythematosus, polyartitis nodosa, Wegener's granulomatosis, giant cell arteritis, rheumatoid arthritis, juvenile rheumatoid arthritis, uveitis, hay fever, allergic rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis, and cirrhosis.

The compounds of the present invention are useful for treating, preventing or reversing the progression of a variety of topical diseases such as inflammatory scalp alopecia, panniculitis, psoriasis, discoid lupus erythematosus, inflamed cysts, atopic dermatitis, pyoderma gangrenosum, pemphigus vulgaris, buflous pemphigoid, systemic lupus erythematosus, dermatomyositis, herpes gestationis, eosinophilic fasciitis, relapsing polychondritis, inflammatory vasculitis, sarcoidosis, Sweet's disease, type I reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma.

The compounds of the present invention are also useful in treating, preventing or reversing the progression of disease states associated with Human Immunodeficiency Virus (HIV), cell apoptosis, and cancer including, but not limited to, Kaposi's sarcoma, immune system activation and modulation, desensitization of inflammatory responses, IIL-I expression, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

The invention also encompasses a method for treating a glucocorticoid receptor mediated disease comprising concomitantly administering to a patient in need of such treatment a compound of Formula I and one or additional more agents. For treating or preventing asthma or chronic obstructive pulmonary disease, the compounds of Formula I may be combined with one or more agents selected from the group consisting of: β-agonists (e.g., salmeterol), theophylline, anticholinergics (e.g., atropine and ipratropium bromide), cromolyn, nedocromil and leukotriene modifiers (e.g., montelukast). For treating or preventing inflammation, the compounds of Formula I may be combined with one or the following: a salicylate, including acetylsalicylic acid, a non-steroidal antiinflammatory drug, including indomethacin, sulindac, mefenamic, meclofenamic, tolfenamic, tolmetin, ketorolac, dicofenac, ibuprofen, naproxen, fenoprofen, ketoprofen, flurbiprofin and oxaprozin, a TNF inhibitor, including etanercept and infliximab, an IL-1 receptor antagonist, a cytotoxic or immunosuppressive drug, including methotrexate, leflunomide, azathioprine and cyclosporine, a gold compound, hydroxychloroquine or sulfasalazine, penicillamine, darbufelone, and a ρ38 kinase inhibitor. The compound of Formula I may also be used in combination with bisphonates such as alendronate to treat a glucocorticoid mediated disease and simultaneously inhibit osteoclast-mediated bone resorption.

Methods of Synthesis

Generally, compounds of the present invention may be synthesized by following the following synthetic scheme:

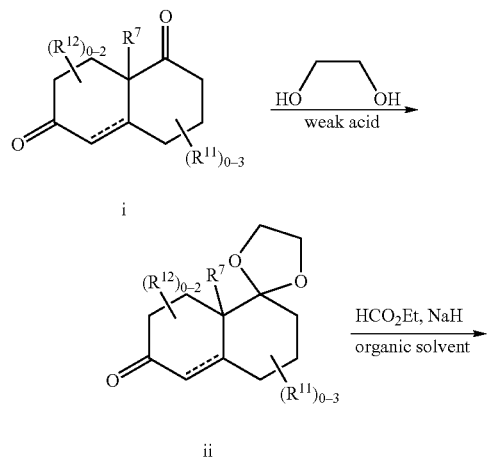

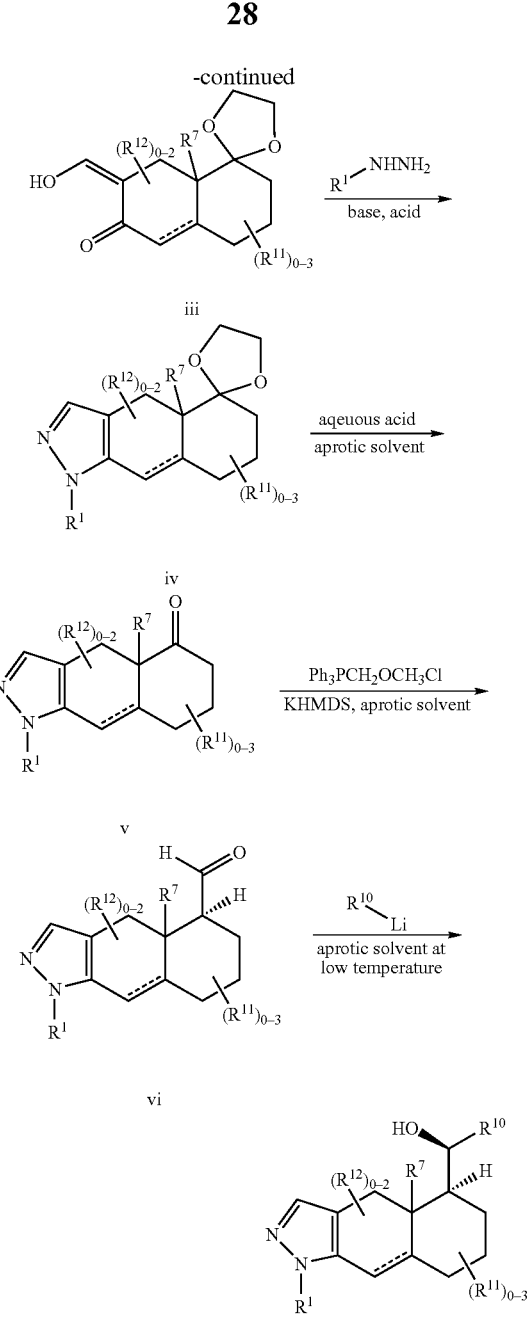

Acid, such as p-toluenesulfonic acid, is added to a solution of the Wieland-Miescher ketone i in ethylene glycol to give ketal ii. Ethyl formate and sodium hydride are added to ketal ii in an organic solvent such as anhydrous benzene to afford hydroxyketone iii. The hydroxyketone iii is dissolved in an appropriate acid such as glacial acetic acid and the appropriate hydrazine such as p-fluorophenylhyradzine hydrocloride and appropriate base such as sodium acetate is added to give pyrazole ketal iv. The pyrazole ketal iv is dissolved in an aprotic solvent such as THF and an aqeuous acid such as aqeuous 6N HCl is added to yield the ketone v.

Potassium bis(trimethylsilyl amide) is added to (methoxymethyl)triphenylphosponium chloride in an aprotic solvent such as THF. Ketone v is added to afford compound vi.

$R^{10}$-Li is added in an aprotic solvent such as THF at low temperature to yield the final product vii.

Methods for making compounds of Formula I outside the scope of formula vii are easily discernible by those having ordinary skill in the art in view of the above method and the examples set for the below. See, for example, Syth. Commun., 1994, vol. 24, pp. 279-292; Org. Syth., 1985, vol. 63, pp. 37-43; Org. Syth., 1985, vol. 63, pp. 26-36; and Setroids, 1963, vol. 2, p. 399.

The invention will now be illustrated by the following non-limiting examples in which, unless stated otherwise:

(i) all operations were carried out at room or ambient temperature, that is, at a temperature in the range 18-25° C., (ii) evaporation of solvent was carried out using a rotary evaporator under reduced pressure (600-4000 pascals: 4.5-30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 500 MHz or 600 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (litre(s)), mL (millilitres), g (gram(s)), mg (milligrams(s)), mol (moles), mmol (millimoles), eq (equivalent(s)).

PREPARATIVE EXAMPLES

Ketone A

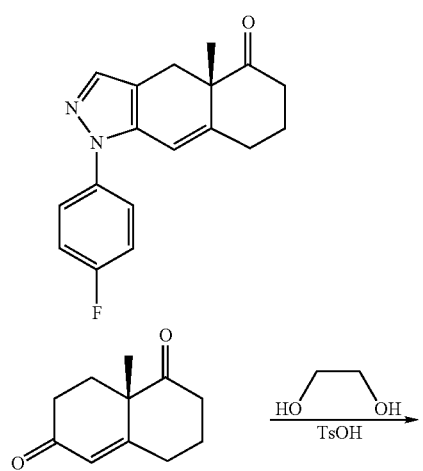

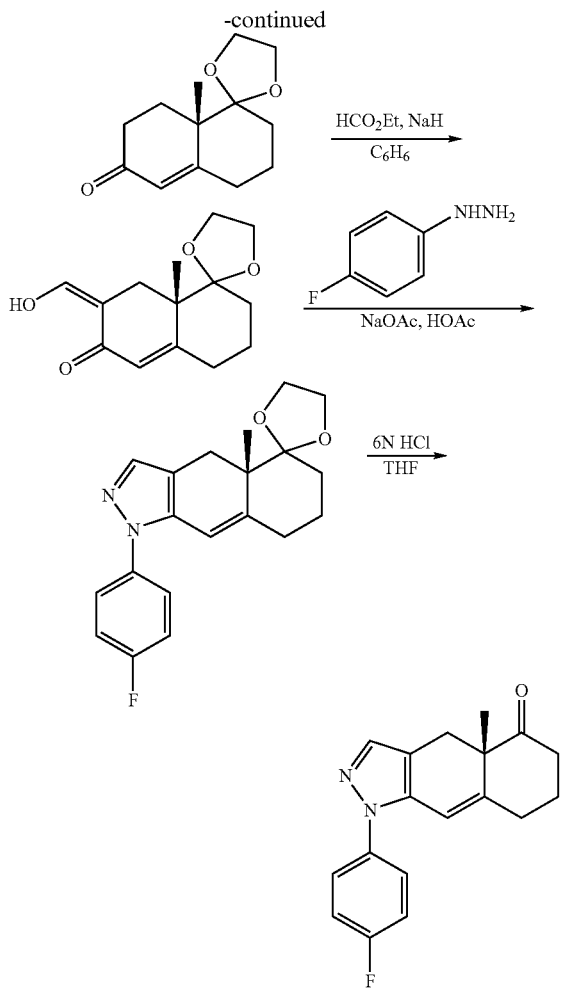

Step 1:

4 Å molecular sieves (~5 g) and p-toluenesulfonic acid (5.34 g, 28.05 mmol) were added to a solution of the Wieland-Miescher ketone (5 g, 28.05 mmol) in ethylene glycol (140 mL). After stirring at room temperature for 23 min., the reaction was poured slowly into a 2:1 mixture of ice water/sat. aqeuous NaHCO$_3$ (150 mL). The reaction was extracted with EtOAc (4×100 mL) and the combined organic layers were washed with brine (100 mL), dried over MgSO$_4$, filtered and concentrated in vacuo. The residue was purified by flash chromatography (0 to 40% EtOAc/hexanes) on silica gel to afford 5.77 g (93%) of the ketal as a white solid. LCMS=223; (M+1)$^+$. $^1$H NMR (CDCl$_3$, 500 MHz): δ 5.83 (br d, J=1.8 Hz, 1H), 4.43-3.94 (m, 4H), 2.49-2.40 (m, 3H), 2.39-2.27 (m, 2H), 1.95-1.88 (m, 1H), 1.84-1.78 (m, 1H), 1.76-1.64 (m, 3H), 1.37 (s, 3H).

Step 2:

Ethyl formate (7.36 mL, 86.48 mmol) and sodium hydride (60% suspension in mineral oil; 3.46 g, 86.48 mmol) were added to a cooled solution (–40° C.) of the ketal in anhydrous benzene (200 mL). MeOH (450 μL) was added dropwise over 15 min. and the reaction allowed to warm to room temperature. After stirring for 3 h, the reaction was cooled to 0° C. and 50 mL H$_2$O was added. The biphasic system was shaken and the organic layer was washed with H$_2$O (3×50 mL). The combined aqueous layers were washed with diethyl ether (100 mL) and then acidified to pH 5.5-6 with sat. aqueous KH$_2$PO$_4$. The aqueous layer was extracted with EtOAc (5×200 mL). The combined extracts were dried over Na$_2$SO$_4$ and concentrated in vacuo to afford 5.04 g (93%) of hydroxyketone product as an orange oil. LCMS=251; (M+1)$^+$.

Step 3:

The hydroxyketone (4.1 g, 16.4 mmol) was dissolved in glacial acetic acid (40 mL) and p-fluorophenylhyradzine hydrocloride (2.8 g, 17.22 mmol) and sodium acetate (1.41 g, 17.22 mmol) were added. After stirring at room temperature for 2 h, the reaction was poured slowly into 10% NaHCO$_3$ (1 L) and extracted with EtOAc (6×500 mL). The combined extracts were washed with brine (500 mL), dried over MgSO$_4$ and concentrated in vacuo. The crude material was purified by flash chromatography (10% EtOAc/hexanes) on silica gel to afford 2.26 g (41%) of the pyrazole ketal as an orange solid. LCMS=421; (M+1)$^+$. $^1$H NMR (CDCl$_3$, 500 MHz): δ 7.47-7.44 (m, 2H), 7.43 (s, 1H), 7.18-7.16 (d, J=8.5 Hz, 1H), 7.16-7.14 (d, J=8.7 Hz, 1H), 6.22 (br d, J=2.2 Hz, 1H), 4.11-4.01 (m, 4H), 3.20-3.16 (d, J=15.7 Hz, 1H), 2.54-2.51 (d, J=16 Hz, 1H), 2.51-2.40 (m, 1H), 2.34-2.28 (m, 1H), 1.88-1.64 (m, 4H), 1.23 (s, 3H).

Step 4:

The pyrazole ketal (2.26 g; 6.65 mmol) was dissolved in THF (65 mL) and 6N HCl (4.43 mL, 26.6 mL) was added. The reaction was heated at 65° C. for 3.5 h and then poured slowly into 10% NaHCO$_3$ (150 mL). The mixture was extracted with EtOAc (4×250 mL) and the combined extracts washed with brine (2×200 mL), dried over MgSO$_4$ and concentrated in vacuo to afford 1.97 g (100%) of Ketone A as a brown oil. LCMS=297; (M+1)$^+$. $^1$H NMR (CDCl$_3$, 500 MHz): δ 7.50 (s, 1H), 7.49-7.45 (m, 2H), 7.20-7.16 (m, 2H), 6.31 (br d, J=2 Hz, 1H), 2.96-2.88 (m, 2H), 2.72-2.62 (m, 2H), 2.59-2.53 (m, 2H), 2.14-2.08 (m, 1H), 1.75-1,64 (qt, J=13.1 Hz, J=4.3 Hz, 1H), 1.27 (s, 3H).

Aldehyde B

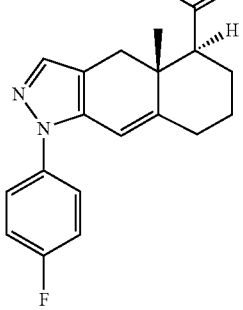

B

Step 1: Preparation of Aldehyde B

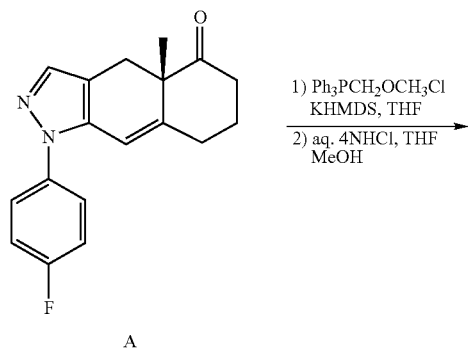

A

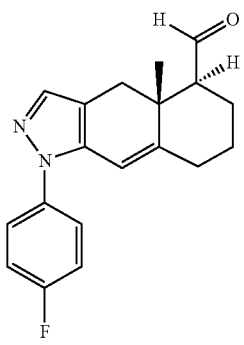

B

A suspension of (methoxymethyl)triphenylphosponium chloride (4.17 g, 12.16 mmol) in THF (40 mL) was cooled to −40° C. Potassium bis(trimethylsilyl amide) (20.3 mL of a 0.5 M solution in toluene, 10.15 mmol) was added dropwise by syringe and the reaction was allowed to warm to 0° C. and held at that temperature for 15 min. A solution of ketone A (1.2 g, 4.05 mmol) in THF (12 mL) was added and the reaction was allowed to warm to room temperature. After stirring at room temperature for 24 h, 10 mL of a 1:1 solution of TBF/MeOH was added to the reaction followed by 10 mL of 4 N HCl. The reaction became biphasic and stirring was continued at room temperature. After 36 h, the reaction was diluted with EtOAc (300 mL) and washed with H$_2$O, saturated NaHCO$_3$, and brine (50 mL each). The organic layer was dried over Na$_2$SO$_4$, filtered and concentrated in vacuo. The residue was purified by flash chromatography (5 to 25% EtOAc/hexanes) on silica gel to afford 939.7 mg (75%) of the product B as a tan solid; 8:1 (β:α) mixture of aldehyde diastereomers. R$_f$=0.19 (25% EtOAc/hexanes). LCMS=311; (M+1)$^+$. $^1$H NMR (major isomer) (CDCl$_3$, 500 MHz) δ 9.91 (d, J=1.8 Hz, 1H), 7.43-7.46 (m, 3H), 7.16 (t, J=8.6 Hz, 2H), 6.17 (d, J=1.9 Hz, 1H), 3.11 (d, J=15.6 Hz, 1H), 2.91 (d, J=15.6 Hz, 1H), 2.32-2.45 (m, 3H), 1.87-1.98 (m, 2H), 1.75 (m, 1H), 1.43 (m, 1H), 1.12 (s, 3H).

Ketone C was prepared in the same manner as ketone A.

Aldehyde F

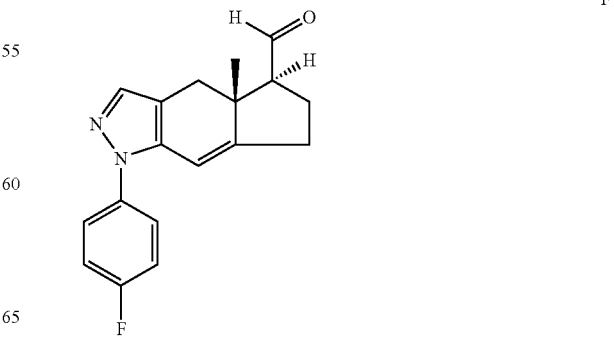

F

Step 1:

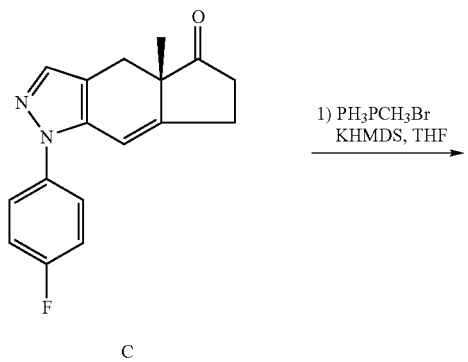

C

1) PH₃PCH₃Br
KHMDS, THF
→

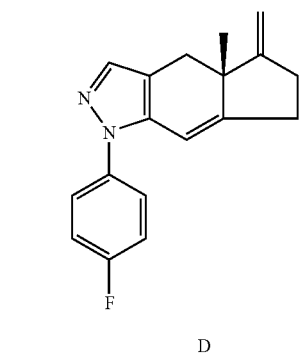

D

A suspension of methyltriphenylphosphonium bromide (2.05 g, 5.75 mmol) in THF (25 mL) was cooled to −40° C. Potassium bis(trimethylsilyl amide) (9.2 mL of a 0.5 M solution in toluene, 4.6 mmol) was added dropwise by syringe and the reaction was allowed to warm to 0° C. and held at that temperature for 15 minutes. Next, a solution of ketone C (323.7 mg, 1.15 mmol) in THF (5 mL) was added by cannula. The reaction was allowed to warm to room temperature. After stirring at room temperature for 2 hours, the reaction was filtered through a plug of silica gel with 50% EtOAc/hexanes. The filtrate was concentrated and the residue was purified by flash chromatography with 15% EtOAc/hexanes to afford 265.2 mg (83%) of D. $R_f$=0.39 (25% EtOAc/hexanes). LCMS=281; (M+1)⁺. ¹H NMR (CDCl₃, 500 MHz) δ 7.46-7.49 (m, 2H), 7.44 (s, 1H), 7.13-7.17 (m, 2H), 6.19 (s, 1H), 4.95 (s, 1H), 4.86 (s, 1H), 2.81 (d, J=15.3 Hz, 1H), 2.73 (m, 1H), 2.69 (d, J=15.6 Hz, 1H), 2.54-2.67 (m, 2H), 2.48 (m, 1H), 1.17 (s, 3H).

Step 2:

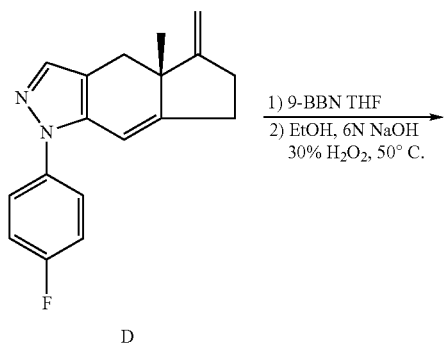

D 1) 9-BBN THF
2) EtOH, 6N NaOH
30% H₂O₂, 50° C.
→

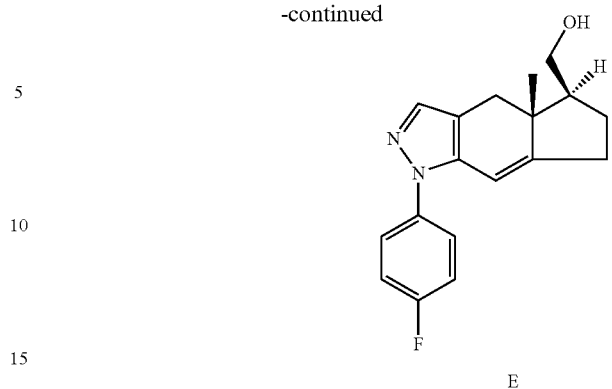

E

To a solution of D (265.2 mg, 0.947 mmol) in TBF (17 mL) was added 9-BBN (5.7 mL of a 0.5 M solution in TBF, 2.84 mmol). The reaction was stirred at room temperature for 1.5 hours and then cooled to 0° C. EtOH (6.8 mL), 6N NaOH (2.25 mL) and 30% H₂O₂ (1.2 mL) were added, the ice bath was removed, and the reaction was heated to 50° C. for 1 hour. The reaction was then cooled to room temperature, diluted with EtOAc (100 mL), and washed with H₂O and brine (50 mL each). The organic layer was dried over Na₂SO₄, filtered, and concentrated in vacuo.

The residue was purified by flash chromatography with 60% EtOAc/hexanes to afford 282.2 mg (100%) of E. $R_f$=0.19 (55% EtOAc/hexanes). LCMS=299; (M+1)⁺. ¹H NMR (CDCl₃, 500 MHz) δ 7.46-7.48 (m, 2H), 7.41 (s, 1H), 7.13-7.16 (m, 2H), 6.14 (s, 1H), 3.81 (dd, J=10.6, 7.1 Hz, 1H), 3.75 (dd, J=10.8, 7.0 Hz, 1H), 2.92 (d, J=15.3 Hz, 1H), 2.66 (d, J=15.3 Hz, 1H), 2.63 (m, 1H), 2.47 (m, 1H), 2.10 (m, 1H), 2.03 (m, 1H), 1.58 (m, 1H), 0.97 (s, 3H).

Step 3:

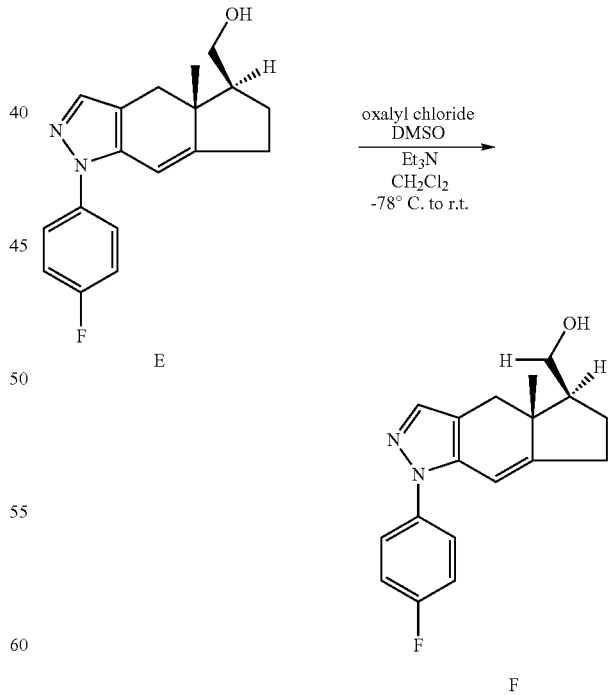

To a solution of oxalyl chloride (46 μL, 0.524 mmol) in CH₂Cl₂ (2 mL) at −78° C. was added DMSO (75 μL, 1.05 mmol) in CH₂Cl₂ (1 mL). The reaction was stirred at −78° C. for 5 minutes and then alcohol E (52.1 mg, 0.175 mmol) in CH₂Cl₂ (2 mL) was added. The reaction was stirred for 15 minutes and then Et₃N (295 µL, 2.1 mmol) was added. The reaction was warmed to room temperature, stirred for 20 minutes, and diluted with EtOAc (50 mL). The organic solution was washed with H₂O, saturated NaHCO₃, brine, 1N HCl, saturated NaHCO₃, and brine (15 mL each). The organic layer was dried over Na₂SO₄, filtered and concentrated in vacuo. The residue was purified by flash chromatography (40% EtOAc/hexanes) to afford 41.5 mg (80%) of F as a clear oil. $R_f$=0.27 (40% EtOAc/hexanes). LCMS=297; (M+1)⁺. ¹H NMR (CDCl₃, 500 MHz) δ 9.89 (d, J=1.6 Hz, 1H), 7.43-7.46 (m, 2H), 7.42 (s, 1H), 7.13-7.16 (m, 2H), 6.17 (s, 1H), 3.01 (d, J=15.4 Hz, 1H), 2.88 (d, J=15.4 Hz, 1H), 2.67-2.75 (m, 2H), 2.51 (m, 1H), 2.56 (m, 1H), 2.06 (m, 1H), 1.06 (s, 3H).

EXAMPLES

Example 1

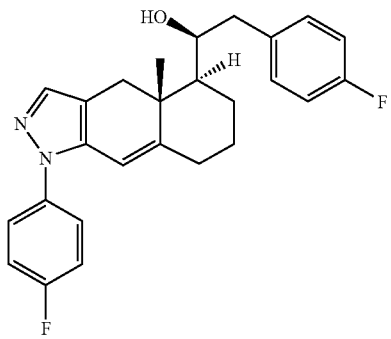

Step 1: Addition of Aryl Grignard Reagents to Aldehyde B

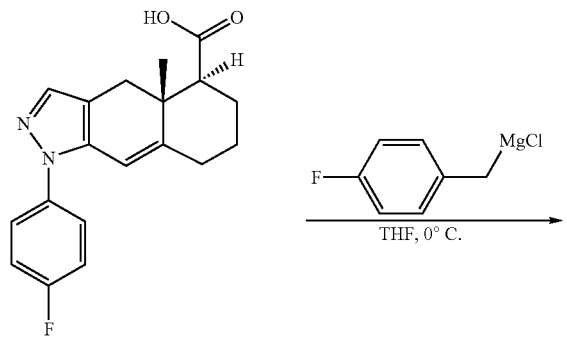

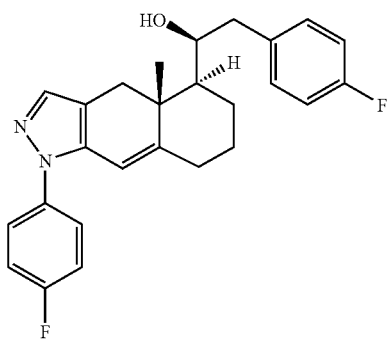

Example 1

Aldehyde B (42.7 mg, 0.138 mmol) was dissolved in TBF (4 mL) and cooled to 0° C. 4-fluorobenzyl magnesium chloride (5.5 mL of a 0.25 M solution in Et₂O, 1.38 mmol) was added dropwise by syringe. The reaction was stirred at 0° C. for 1 h and then quenched with saturated NH₄Cl (25 mL). The mixture was extracted with EtOAc (100 mL) and the organic layer was washed with H₂O and brine (25 mL each), dried over Na₂SO₄, filtered, and concentrated in vacuo. The major product was isolated by flash chromatography (5 to 25% EtOAc/hexanes) to afford 40.6 mg (70%) of Example 1 as a single diastereomer. $R_f$=0.11 (25% EtOAc/hexanes). LCMS=421; (M+1)⁺. ¹H NMR (CDCl₃, 500 MHz): δ 7.42-7.44 (m, 2H), 7.38 (s, 1H), 7.13-7.20 (m, 4H), 7.02 (t, J=8.6 Hz, 2H), 6.09 (d, J=2.3 Hz, 1H), 4.16 (br s, 1H), 2.85-2.90 (m, 2H), 2.68 (dd, J=13.5, 5.7 Hz, 1H), 2.41 (m, 1H), 2.26-2.32 (m, 2H), 1.95 (m, 1H), 1.80 (m, 1H), 1.71 (qd, J=13.0, 3.3 Hz, 1H), 1.56 (dd, J=12.5, 3.5 Hz, 1H), 1.40 (m, 1H), 1.12 (s, 3H).

The following compounds are synthesized following procedures analogous to that described in Example 1:

| Compound | Molecular structure | LCMS (M + 1)⁺ |
| --- | --- | --- |
| 2 | 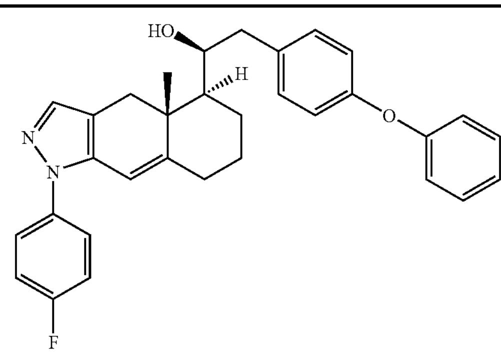 | 481 |

-continued

| Compound | Molecular structure | LCMS (M + 1)+ |
|---|---|---|
| 3 | 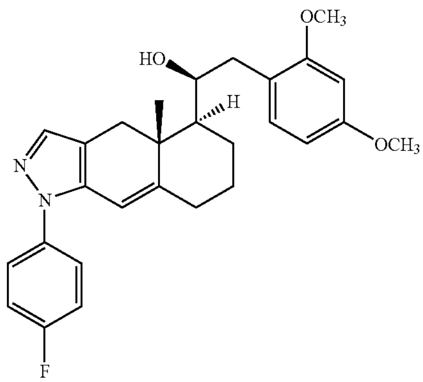 | 449 |
| 4 | 1:1 mixture of E and Z isomers | 353 |
| 5 | mixture of E and Z isomers | 367 |
| 6 | 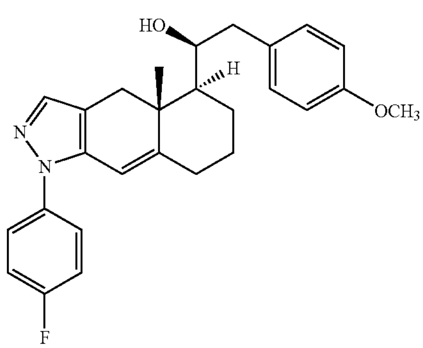 | 433 |

-continued

| Compound | Molecular structure | LCMS (M + 1)+ |
|---|---|---|
| 7 | 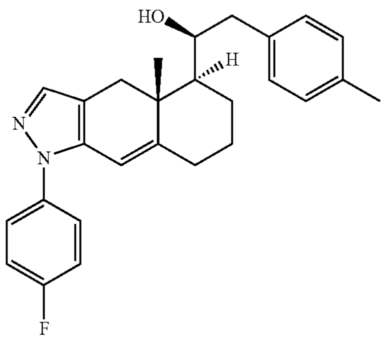 | 417 |
| 8 | 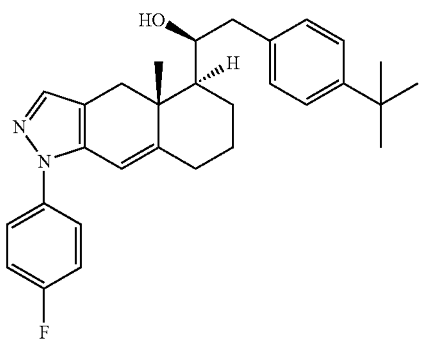 | 459 |
| 9 | 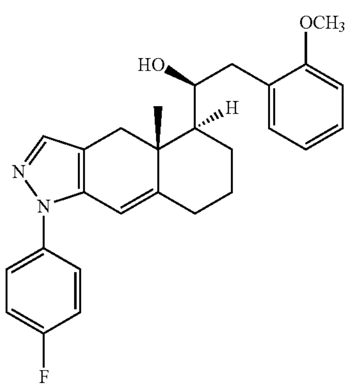 | 433 |
| 10 | 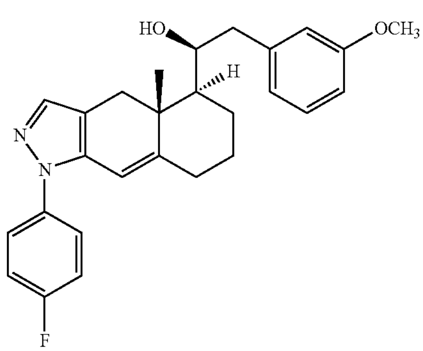 | 433 |

-continued

| Compound | Molecular structure | LCMS (M + 1)+ |
|---|---|---|
| 11 | 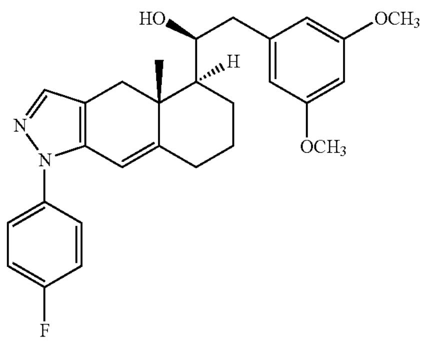 | 463 |
| 12 | 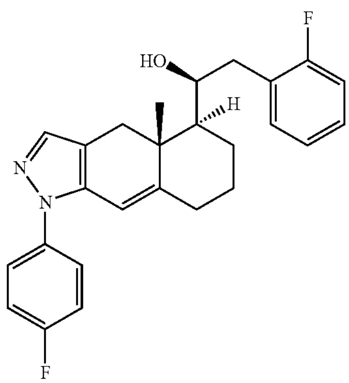 | 421 |
| 13 | 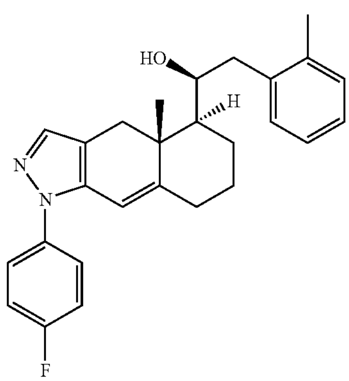 | 417 |
| 14 | 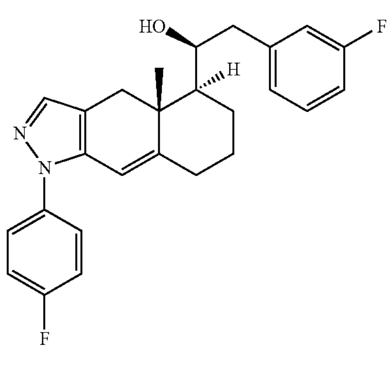 | 421 |

-continued

| Compound | Molecular structure | LCMS (M + 1)+ |
|---|---|---|
| 15 | 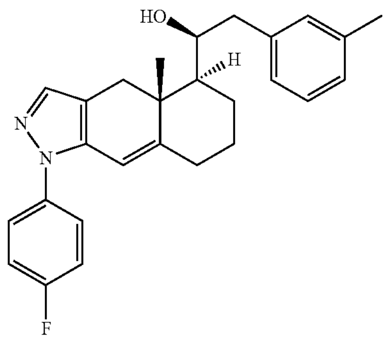 | 417 |
| 16 | 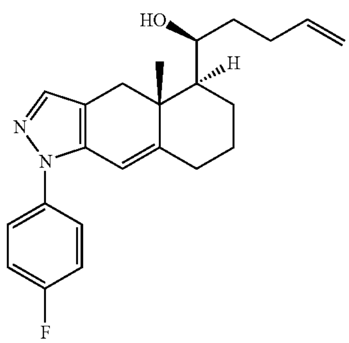 | 367 |
| 17 | 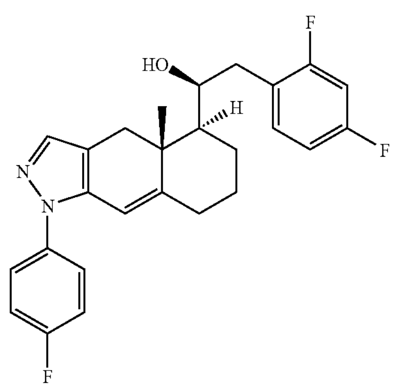 | 439 |
| 18 | 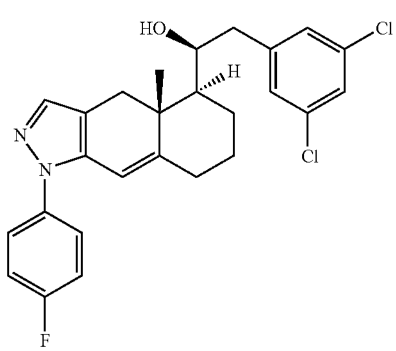 | 472 |

-continued

| Compound | Molecular structure | LCMS (M + 1)+ |
|---|---|---|
| 19 | 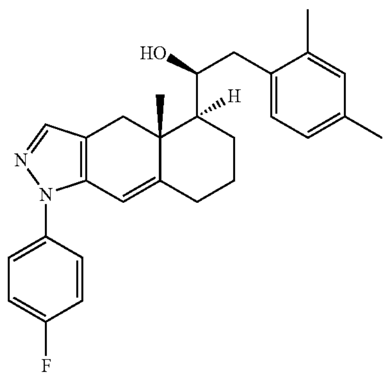 | 431 |
| 20 | 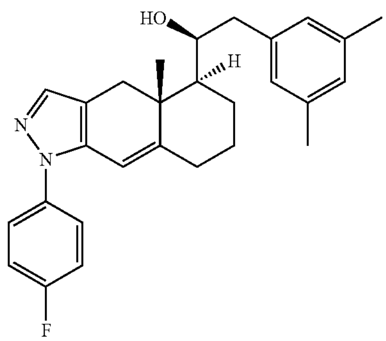 | 431 |
| 21 | 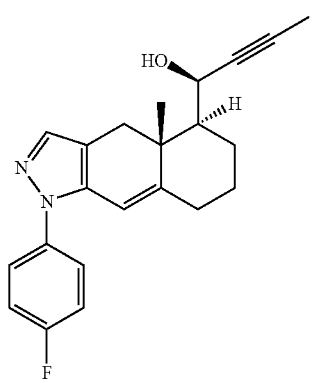 | 351 |
| 22 | 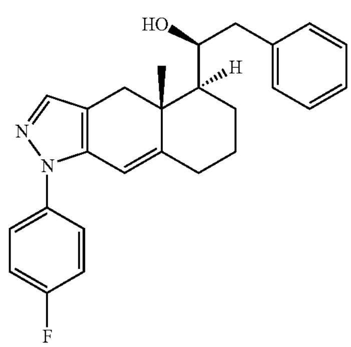 | 403 |

-continued

| Compound | Molecular structure | LCMS (M + 1)+ |
| --- | --- | --- |
| 23 | 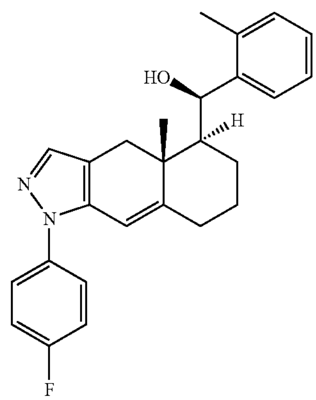 | 403 |
| 24 | 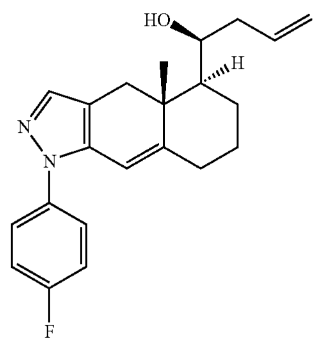 | 353 |
| 25 | 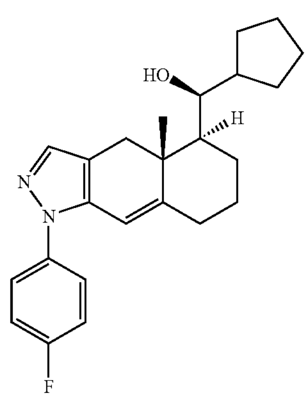 | 381 |
| 26 | 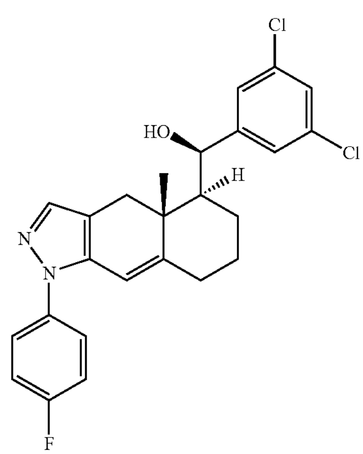 | 457 |

-continued

| Compound | Molecular structure | LCMS (M + 1)+ |
|---|---|---|
| 27 | 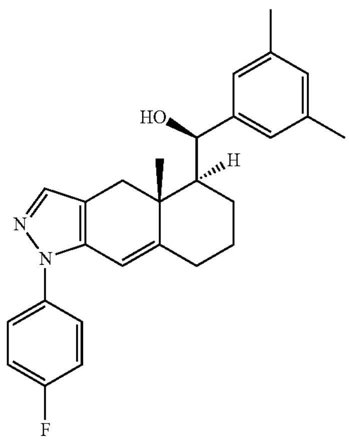 | 417 |
| 28 | 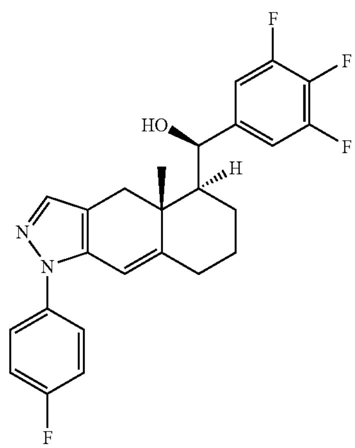 | 443 |
| 29 | 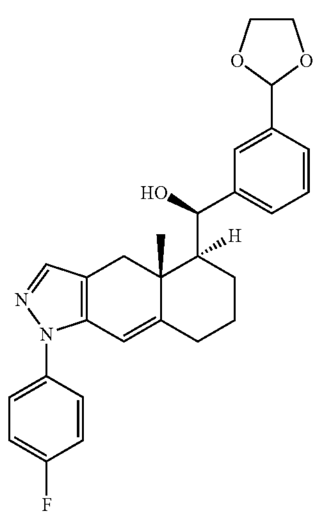 | 461 |

| Compound | Molecular structure | LCMS (M + 1)+ |
|---|---|---|
| 30 | 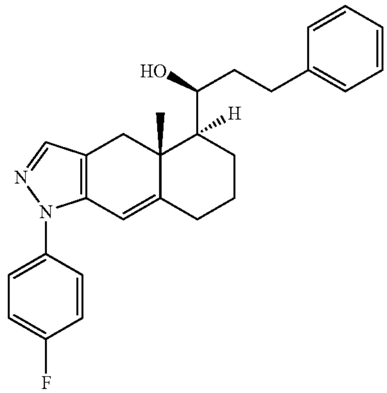 | 417 |
| 31 | 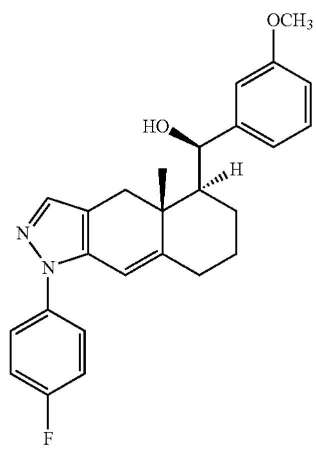 | 419 |
Example 32
Step 1: Addition of Aryl or Vinyl Lithium Reagents to Aldehyde B
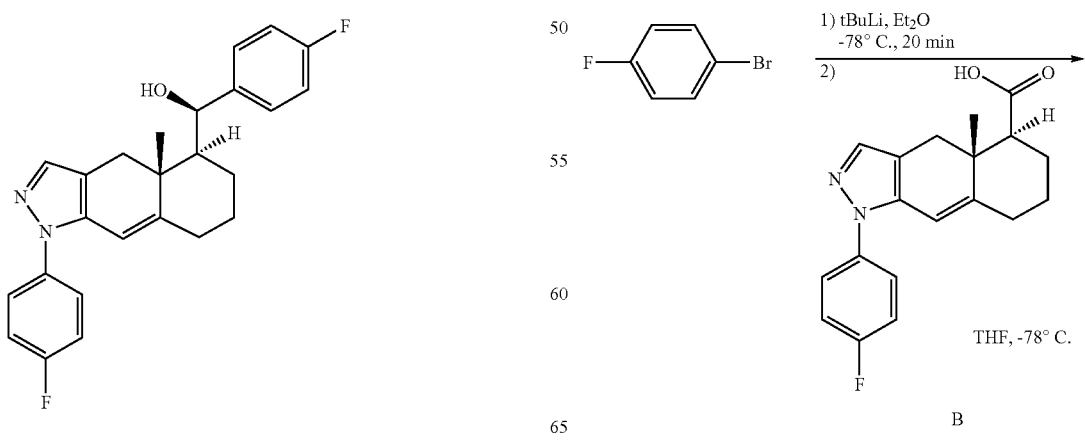

-continued

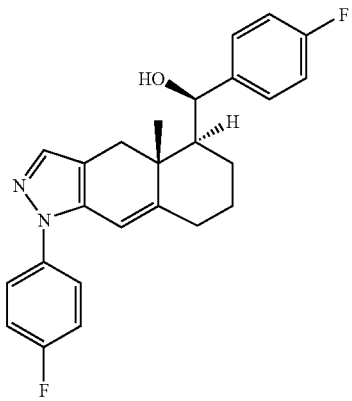

Example 32

A solution of 1-bromo-4-fluorobenzene (176 μL, 1.6 mmol) in Et$_2$O (16 mL) was cooled to −78° C. and tBuLi (1.9 mL of a 1.7 M solution in pentanes, 3.2 mmol) was added dropwise by syringe. The reaction was stirred at −78° C. for 20 min. and then aldehyde B (49.6 mg, 0.16 mmol) in TBF (4 mL) was added by cannula. The reaction was stirred at −78° C. for 45 min. 1 mL of isopropyl alcohol was added at −78° C. and the reaction was poured into saturated NH$_4$Cl. The mixture was extracted with EtOAc (100 mL) and the organic layer was washed with water and brine (25 mL each). The organic layer was dried over Na$_2$SO$_4$, filtered, and concentrated in vacuo. Purification by flash chromatography (5 to 20% EtOAc/hexanes) gave 52.8 mg of Example 32 contaminated with minor diastereomers. Further purification by chiral HPLC (AD column, 20% isopropyl alcohol/heptanes) gave 35.6 mg (55%) of pure Example 32. R$_f$=0.16 (25% EtOAc/hexanes). LCMS=407; (M+1)$^+$. $^1$H NMR (CDCl$_3$, 500 MHz): δ 7.45 (m, 4H), 7.32 (dd, J=9.5, 5.0 Hz, 2H), 7.15 (t, J=8.5 Hz, 2H), 7.04 (t, J=8.8 Hz, 2H), 6.12 (d, J=2.1 Hz, 1H), 5.18 (s, 1H), 3.18 (d, J=15.1 Hz, 1H), 2.75 (d, J=15.1 Hz, 1H), 2.41 (m, 1H), 2.28 (bd, J=15.1 Hz, 1H), 1.82 (m, 1H), 1.66-1.71 (m, 2H), 1.58 (m, 1H), 1.26 (s, 3H), 1.20 (m, 1H).

The following compounds were synthesized following procedures analogous to that described in Example 32:

| Compound | Molecular structure | LCMS (M + 1)$^+$ |
|---|---|---|
| 33 | | 407 |
| 34 | 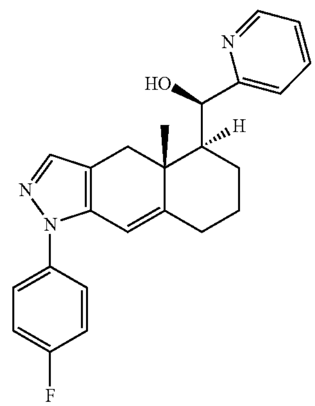 | 390 |
| 35 | 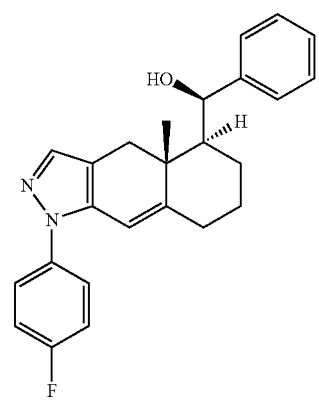 | 389 |
| 36 | 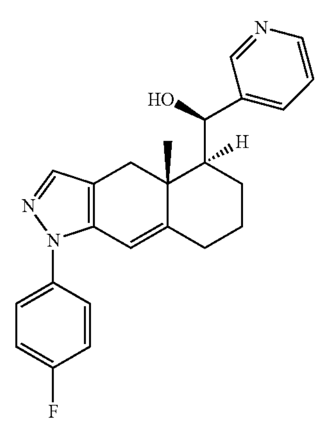 | 390 |

-continued
| Compound | Molecular structure | LCMS (M + 1)+ |
|---|---|---|
| 37 | 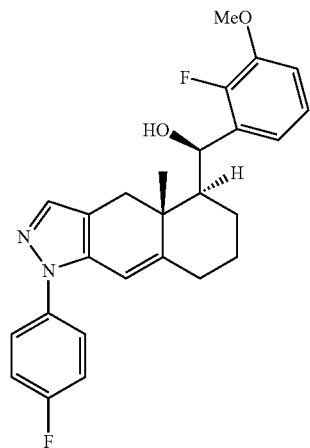 | 437 |
| 38 | 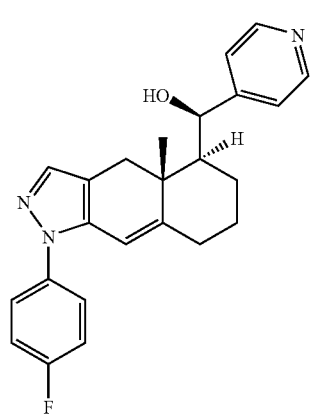 | 390 |
| 39 | 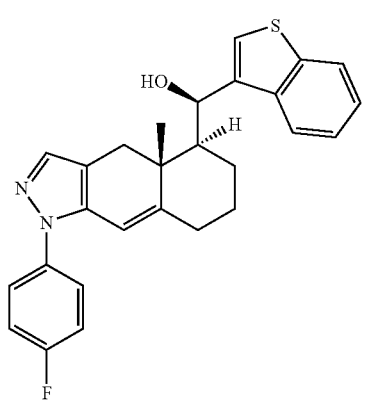 | 445 |
-continued
| Compound | Molecular structure | LCMS (M + 1)+ |
|---|---|---|
| 40 | 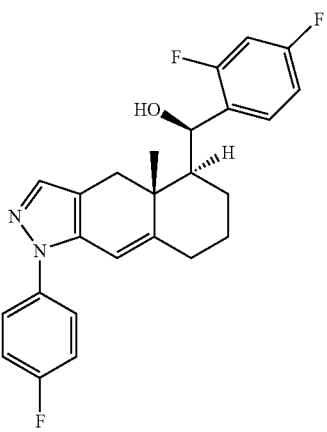 | 425 |
| 41 | 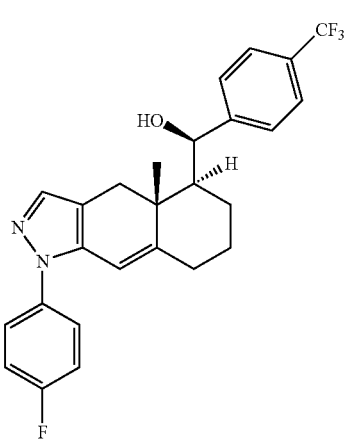 | 457 |
| 42 | 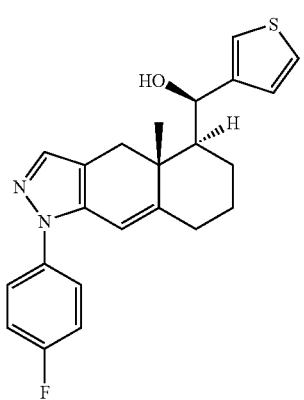 | 395 |

| Compound | Molecular structure | LCMS (M + 1)+ |
|---|---|---|
| 43 | 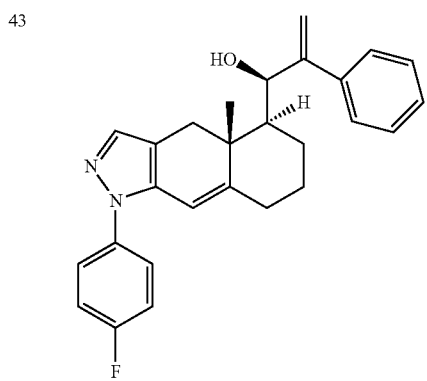 | 415 |
| 44 | 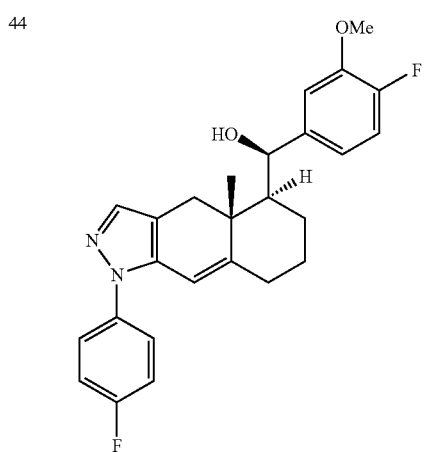 | 437 |
| 45 | 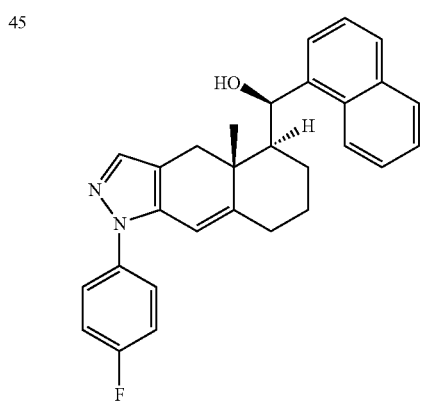 | 439 |
| Compound | Molecular structure | LCMS (M + 1)+ |
|---|---|---|
| 46 | 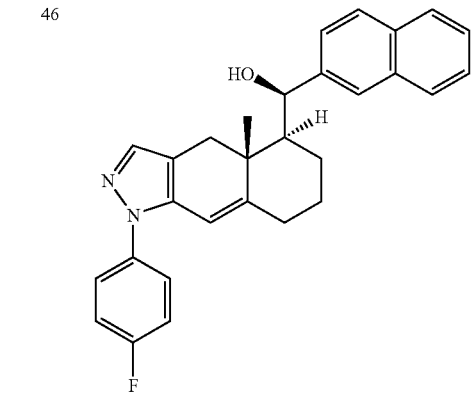 | 439 |
| 47 | 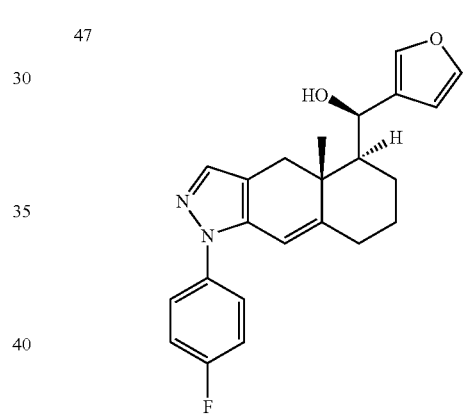 | 379 |
| 48 | 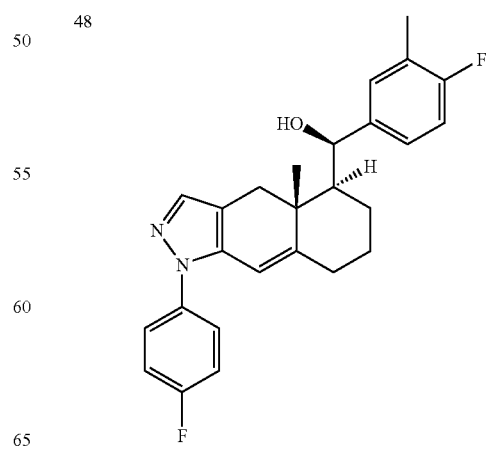 | 421 |

-continued
| Compound | Molecular structure | LCMS (M + 1)+ |
|---|---|---|
| 49 | 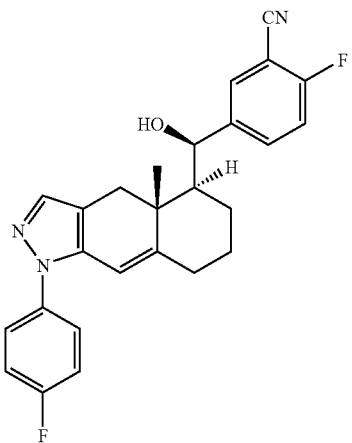 | 433 |
| 50 | 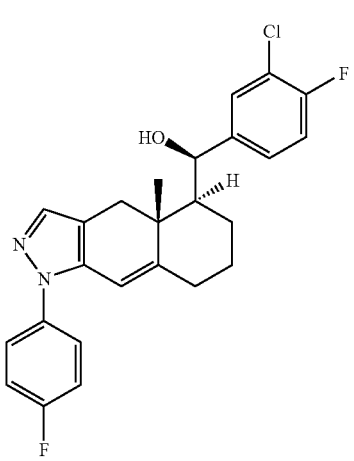 | 441 |
| 51 | 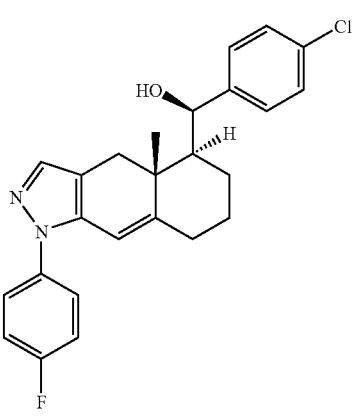 | 423 |
-continued
| Compound | Molecular structure | LCMS (M + 1)+ |
|---|---|---|
| 52 | 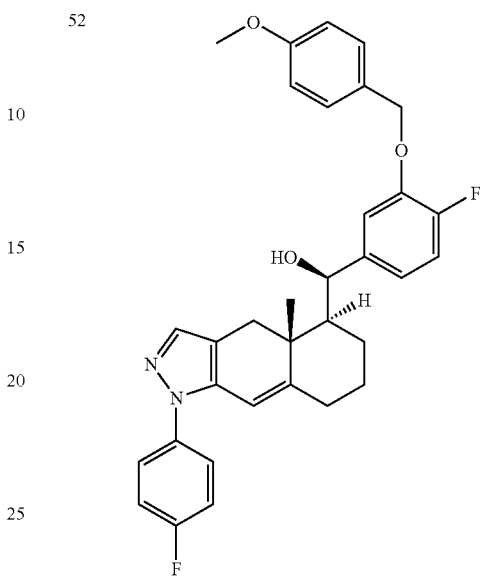 | 543 |
| 53 | 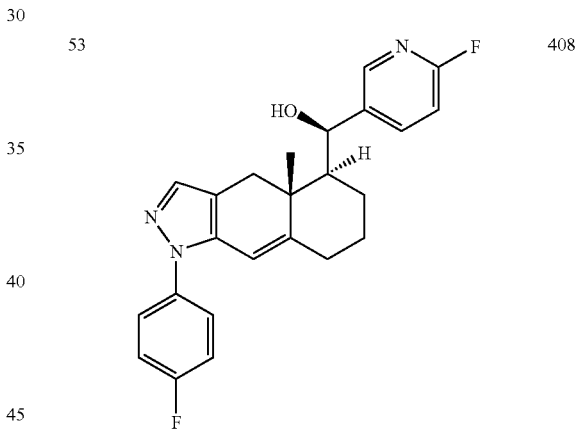 | 408 |
| 54 | 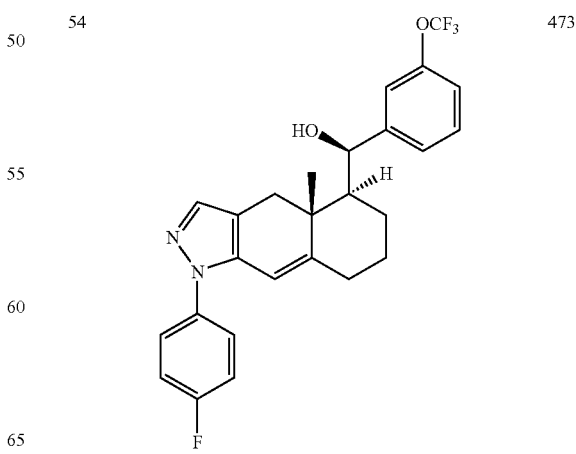 | 473 |

-continued
| Compound | Molecular structure | LCMS (M + 1)+ |
|---|---|---|
| 55 | 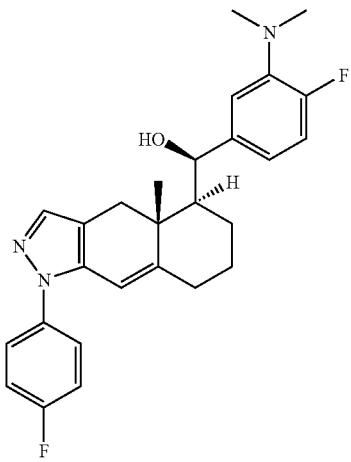 | 450 |
| 56 | 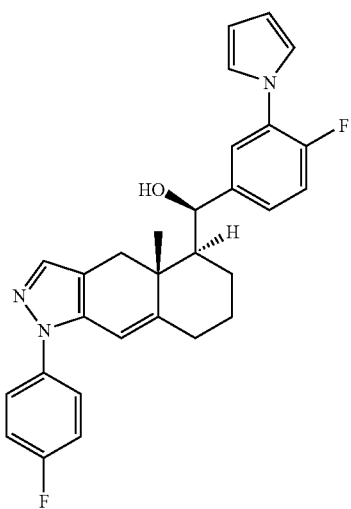 | 472 |
| 57 | 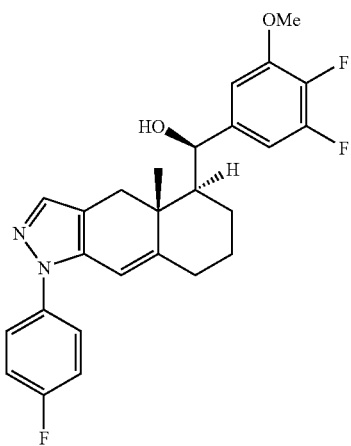 | 455 |
-continued
| Compound | Molecular structure | LCMS (M + 1)+ |
|---|---|---|
| 58 | 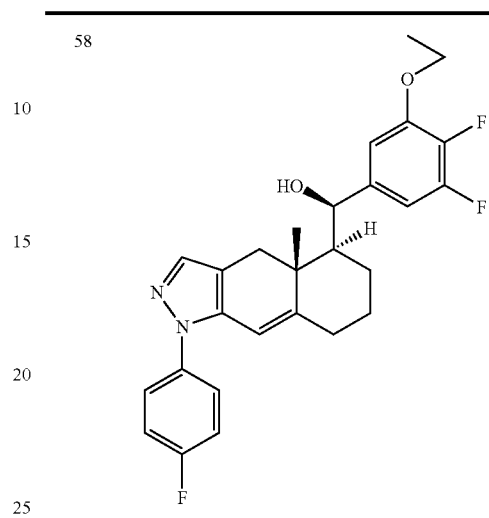 | 469 |
| 59 | 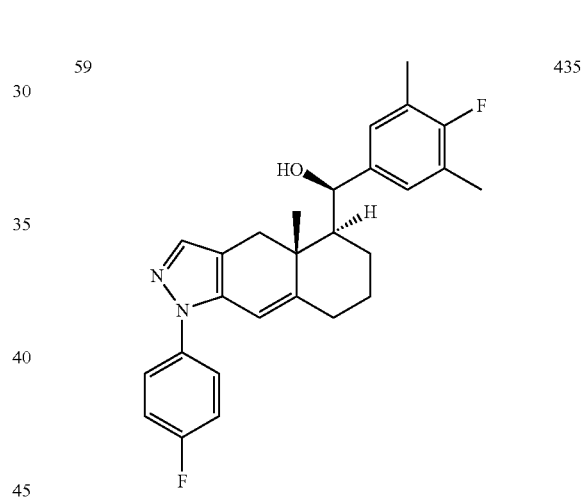 | 435 |
| 60 | 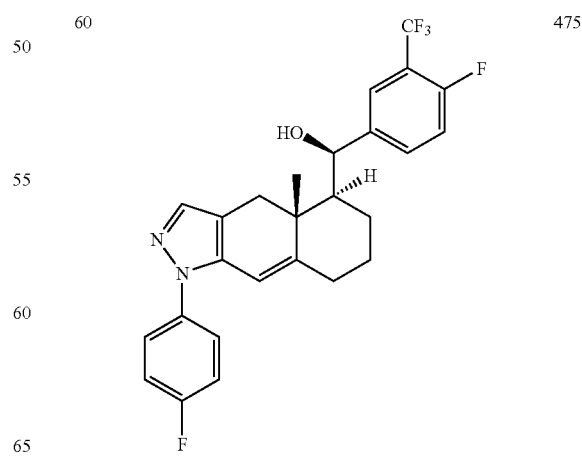 | 475 |

-continued

| Compound | Molecular structure | LCMS (M + 1)+ |
|---|---|---|
| 61 | 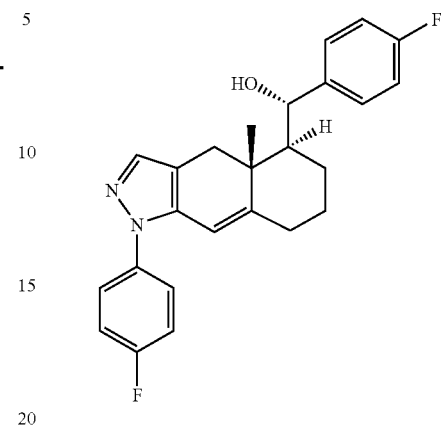 | 433 |
| 62 | 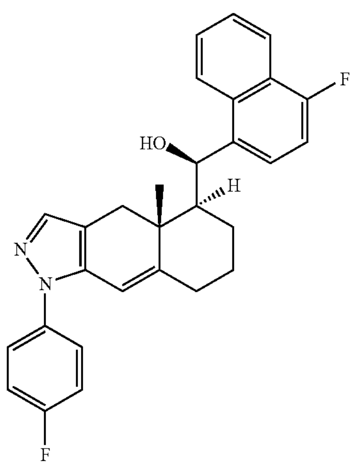 | 457 |
| 63 | 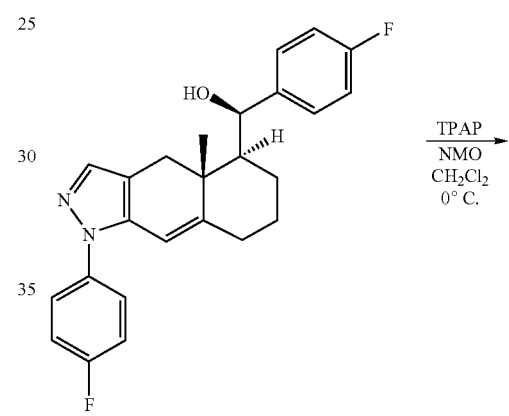 | 463 |

Example 64

Step 1: Oxidation to the ketone.

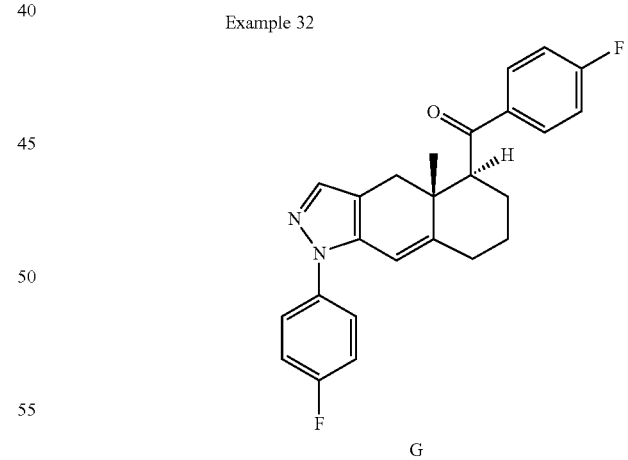

Example 32

G

A solution of Example 32 (23.0 mg, 0.057 mmol) in $CH_2Cl_2$ (2 mL) was cooled to 0° C. and NMO (10 mg, 0.085 mmol) was added. After 5 minutes, TPAP (2 mg, 0.0057 mmol) was added to the reaction. The reaction was stirred at 0° C. for 3 hours and then loaded directly onto a column of silica gel. Elution with 100% $CH_2Cl_2$ followed by 25% EtOAc/hexanes afforded 19.2 mg (84%) of product G. $R_f$=0.32 (25% EtOAc/hexanes). LCMS=405; $(M+1)^+$.

Step 2: Reduction of ketone.

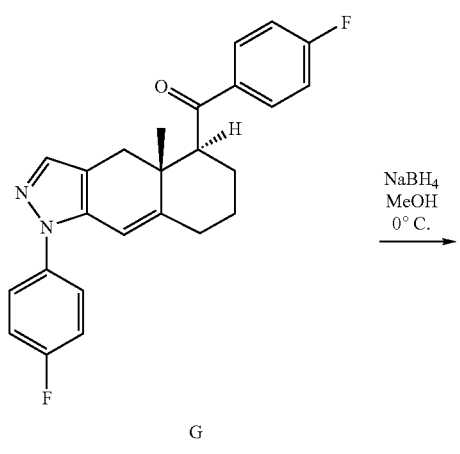

G

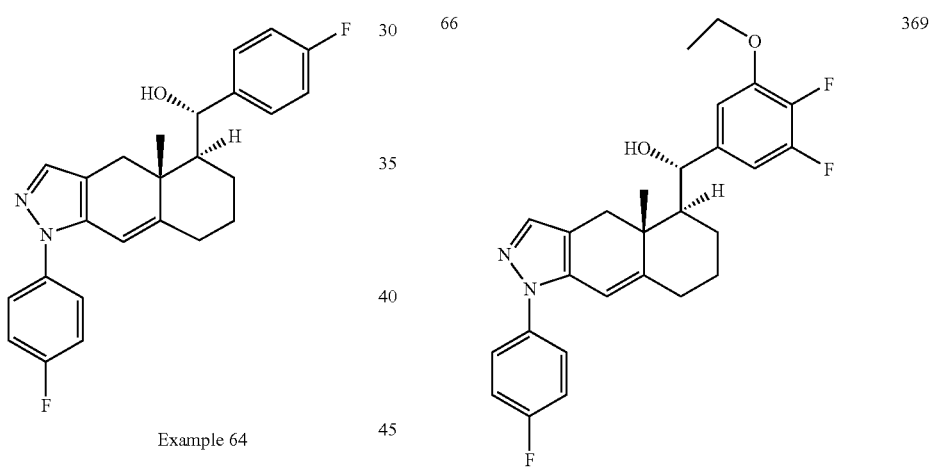

Example 64

Compound G (19.2 mg, 0.048 mmol) was dissolved in MeOH (2 mL) and cooled to 0° C. NaBH$_4$ (10 mg 0.238 mmol) was added. The reaction was stirred at 0° C. for 15 min. and then quenched with saturated NH$_4$Cl (5 mL). The mixture was extracted with EtOAc (30 mL). The organic layer was washed with H$_2$O and brine (10 mL each), dried over Na$_2$SO$_4$, filtered, and concentrated in vacuo. The residue was purified by flash chromatography (40% EtOAc/hexanes) followed by chiral HPLC to remove minor impurities (AD column, 12% IPA/hexanes) to give 12.6 mg (65%) of pure Example 64. R$_f$=0.16 (25% EtOAc/heptanes). LCMS=407; (M+1)$^+$.

$^1$H NMR (CDCl$_3$, 600 MHz): δ 7.45 (dd, J=9.0, 4.8 Hz, 2H), 7.40 (s, 1H), 7.32 (dd, J=8.4, 5.4 Hz, 2H), 7.14 (t, J=8.4 Hz, 2H), 7.04 (t, J=8.4 Hz, 2H), 6.15 (s, 1H), 4.64 (d, J=9.0 Hz, 1H), 3.63 (d, J=16.2 Hz, 1H), 2.78 (d, J=16.2 Hz, 1H), 2.27-2.29 (m, 2H), 2.07 (bs, 1H), 1.89 (m, 1H), 1.68 (m, 1H), 1.05-1.25 (m, 2H), 1.13 (s, 3H).

The following examples were synthesized following a procedure analogous to that described in Example 64:

| Compound | Molecular structure | LCMS (M + 1)$^+$ |
|---|---|---|
| 65 | 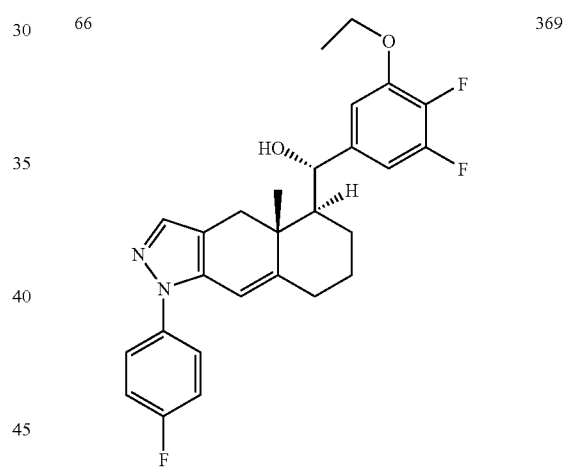 | 390 |
| 66 | 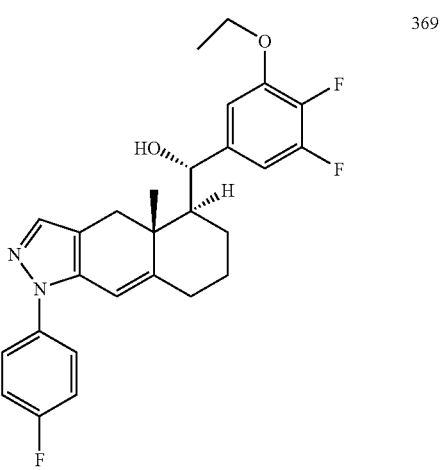 | 369 |
| 67 | 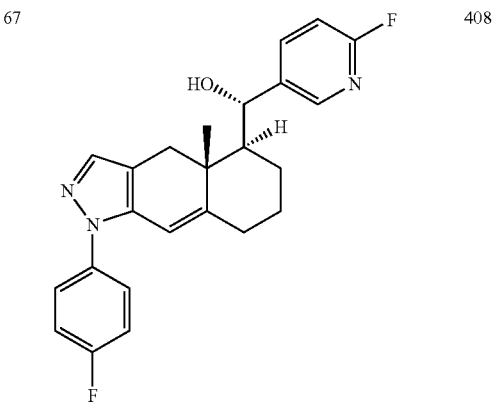 | 408 |

-continued

| Compound | Molecular structure | LCMS (M + 1)+ |
|---|---|---|
| 68 | 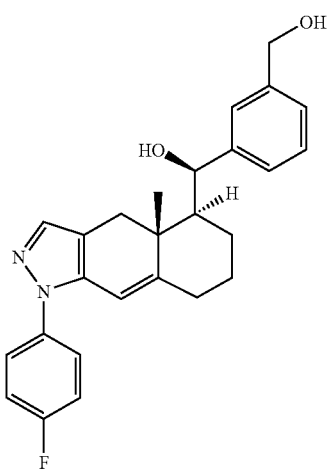 | 445 |

Example 69

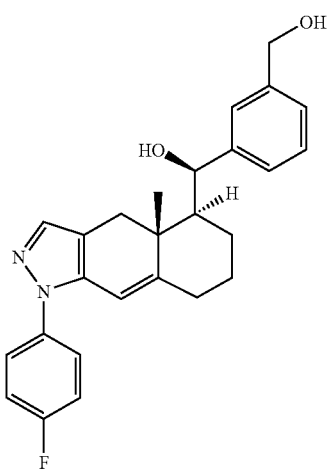

Step 1: Addition of Aryl Lithium to Aldehyde B.

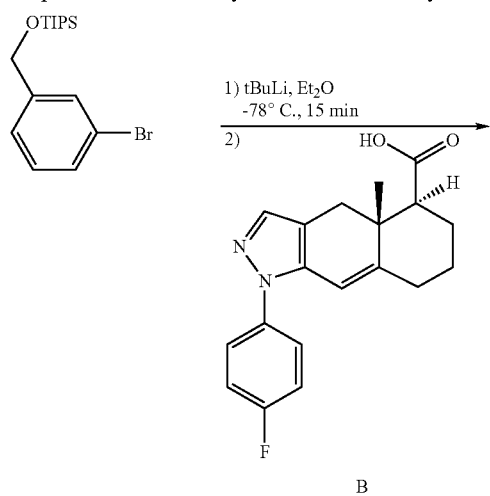

-continued

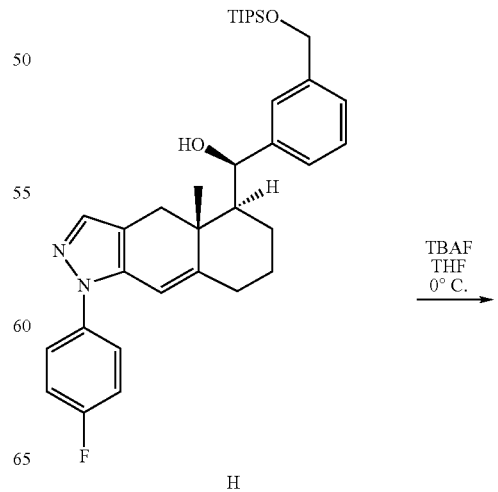

A solution of O-triisopropylsilyloxy-3-bromobenzyl alcohol (230 mg, 0.67 mmol) in $Et_2O$ (6.5 mL) was cooled to −78° C. and t-BuLi (785 μL of a 1.7 M solution in pentanes, 1.34 mmol) was added. The reaction was stirred at −78° C. for 15 min. Aldehyde B (20.7 mg, 0.067 mmol) was added by cannula as a solution in TBF (2 mL). The reaction was stirred at −78° C. for 30 min. 1 mL of isopropyl alcohol was added and the reaction was poured into saturated $NH_4Cl$ (15 mL). The mixture was extracted with EtOAc (50 mL). The organic layer was washed with $H_2O$ and brine (15 mL each), dried over $Na_2SO_4$, filtered, and concentrated in vacuo. The residue was purified by flash chromatography (silica gel, 5 to 15% EtOAc/hexanes) to give 32.4 mg of product containing 1 major and 2 minor diastereomers. Further purification by chiral HPLC (AD column, 15% IPA/heptanes) afforded 19.4 mg (51%) of pure H (major diastereomer). $R_f$=0.22 (25% EtOAc/hexanes). LCMS=575; (M+1)+. $^1$H NMR ($CDCl_3$, 500 MHz): δ 7.45-7.48 (m, 3H), 7.36 (s, 11), 7.33 (t, J=7.6 Hz, 1H), 7.24 (t, J=6.8 Hz, 2H), 7.13-7.17 (m, 2H), 6.11 (d, J=2.0 Hz, 1H), 5.19 (s, 1H), 4.86 (s, 2H), 3.19 (d, J=15.1 Hz, 1H), 2.76 (d, J=15.1 Hz, 1H), 2.41 (m, 1H), 2.27 (br d, J=15.1 Hz, 1H), 1.63-1.82 (m, 5H), 1.27 (s, 3H), 1.15-1.22 (m, 3H), 1.10 (d, J=6.9 Hz, 18H).

Step 2: Desilyation of the Protected Alcohol or Phenol

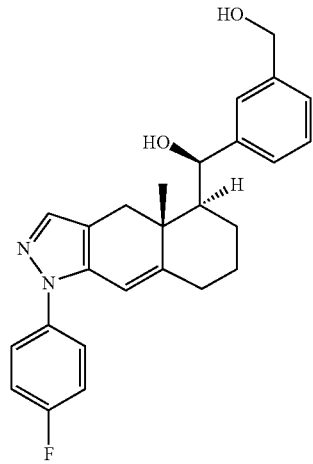

Example 69

Compound H (19.4 mg, 0.034 mmol) was dissolved in THF (3 mL) and cooled to 0° C. TBAF (169 μL of a 1 M solution it THF, 0.169 mmol) was added. The reaction was stirred at 0° C. for 20 min. and then quenched with saturated NH$_4$Cl (5 mL). The mixture was extracted with EtOAc (30 mL). The organic layer was washed with H$_2$O and brine (10 mL each), dried over Na$_2$SO$_4$, filtered, and concentrated in vacuo. The residue was purified by flash chromatography (75% EtOAc/hexanes) to give 12.9 mg (91%) of pure Example 69. R$_f$=0.28 (75% EtOAc/hexanes). LCMS=419; (M+1)$^+$. $^1$H NMR (DMSO, 500 MHz): δ 7.50-7.53 (m, 3H), 7.34 (t, J=8.8 Hz, 2H), 7.29 (s, 1H), 7.25 (t, J=7.4 Hz, 1H), 7.21 (d, J=7.6 Hz, 1H), 7.12 (d, J=7.3 Hz, 1H), 6.17 (s, 1H), 5.12 (t, J=5.8 Hz, 1H), 4.99-5.03 (m, 2H), 4.48 (d, J=5.7 Hz, 2H), 3.19 (d, J=15.3 Hz, 1H), 2.73 (d, J=15.3 Hz, 1H), 2.26-2.36 (m, 2H), 1.63-1.71 (m, 2H), 1.53 (d, J=11.2 Hz, 1H), 1.38 (d, J=12.8 Hz, 1H), 1.17 (s, 3H), 1.03 (m, 1H).

The following examples were synthesized following a procedure analogous to that described in Example 69:

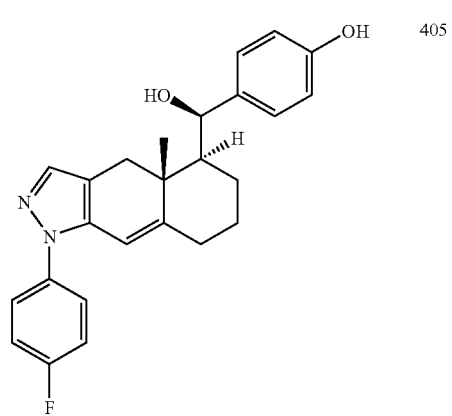

| Compound | Molecular structure | LCMS (M + 1)$^+$ |
|---|---|---|
| 70 |  | 405 |
| 71 | 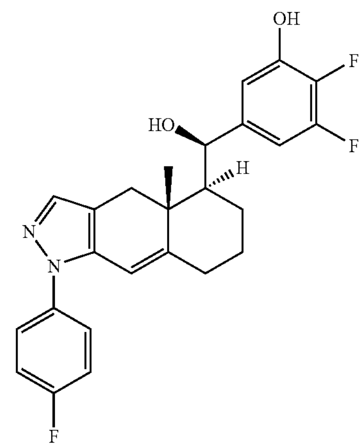 | 441 |
| 72 | 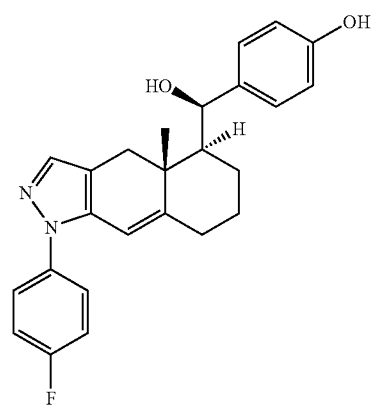 | 405 |
| 73 | 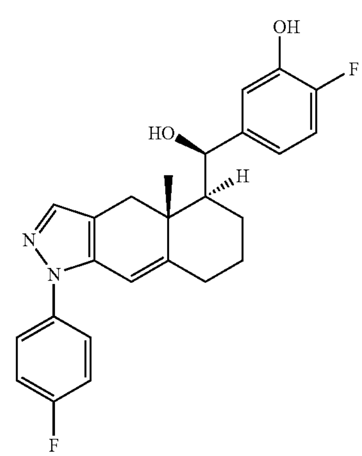 | 405 |

Example 74

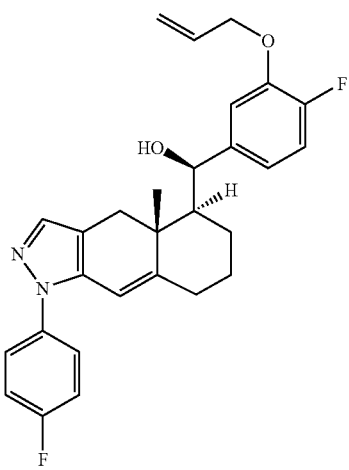

Step 1: Alkylation of Example 73.

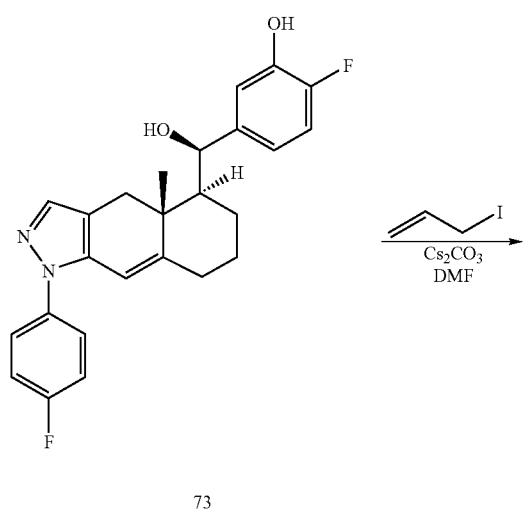

Example 73 (10.5 mg, 0.025 mmol) and Cs$_2$CO$_3$ (32.4 mg, 0.100 mmol) were combined in a 10 mL flask and DMF (1 mL) was added. Allyl iodide (5 µL, 0.055 mmol) was added and the reaction was stirred at room temperature for 1 hour. Next, the reaction was poured into H$_2$O (5 mL) and the aqueous solution was extracted with EtOAc (25 mL). The organic layer was washed with brine (5 mL), dried over Na$_2$SO$_4$, filtered, and concentrated in vacuo. Purification of the residue by flash chromatography (40% EtOAc/hexanes) afforded 11.4 mg (99%) of Example 74. R$_f$=0.25 (40% EtOAc/hexanes). LCMS=463; (M+1)$^+$. $^1$H NMR (CDCl$_3$, 500 MHz): δ 7.44-7.47 (m, 3H), 7.16 (t, J=8.5 Hz, 2H), 7.05 (dd, J=11.0, 8.0 Hz, 1H), 6.99 (dd, J=8.5, 2.0 Hz, 1H), 6.85 (m, 1H), 6.11 (d, J=1.5 Hz, 1H), 6.07 (m, 1H), 5.43 (dd, J=17.5, 1.5 Hz, 1H), 5.31 (dd, J=10.5, 1.0 Hz, 1H), 5.13 (s, 1H), 4.63 (d, J=4.5 Hz, 1H), 3.17 (d, J=15.0 Hz, 1H), 2.73 (d, J=15.0 Hz, 1H), 2.40 (m, 1H), 2.28 (d, J=15.0 Hz, 1H), 1.58-1.83 (m, 4H), 1.25 (s, 3H), 1.21 (m, 1H).

The following examples were synthesized following a procedure analogous to that described in Example 74:

| Compound | Molecular structure | LCMS (M + 1)$^+$ |
|---|---|---|
| 75 | 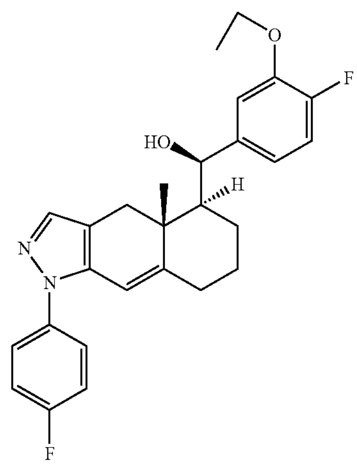 | 451 |
| 76 | 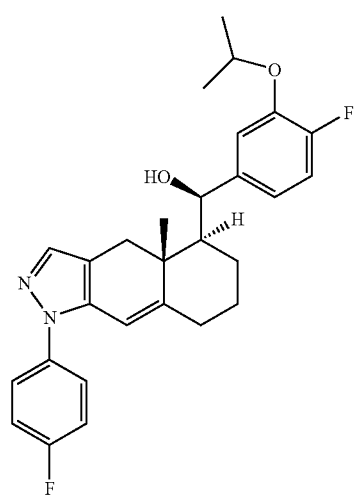 | 465 |

-continued
| Compound | Molecular structure | LCMS (M + 1)+ |
|---|---|---|
| 77 | 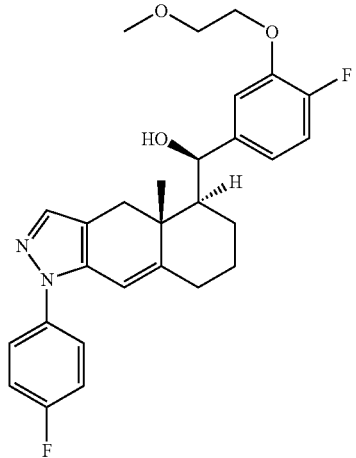 | 481 |
| 78 | 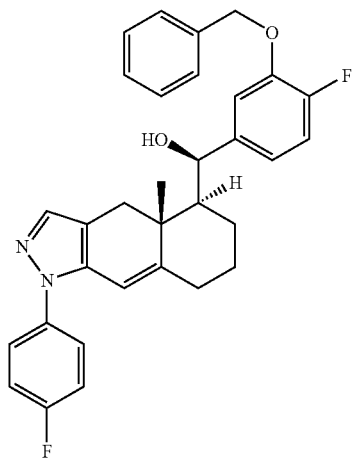 | 513 |
| 79 | 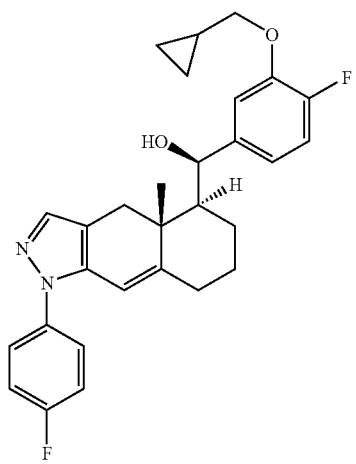 | 477 |
-continued
| Compound | Molecular structure | LCMS (M + 1)+ |
|---|---|---|
| 80 | 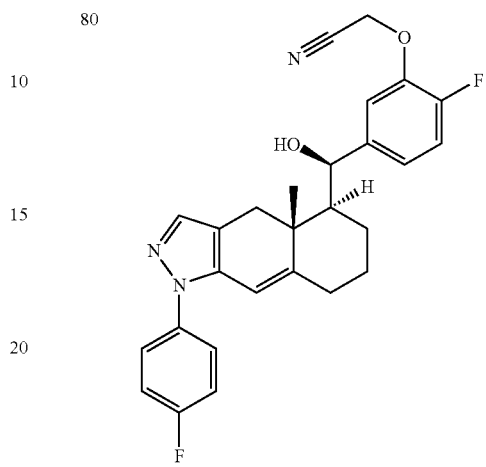 | 462 |
| 81 | 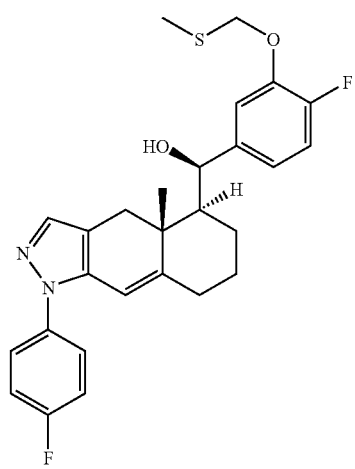 | 483 |
Example 82
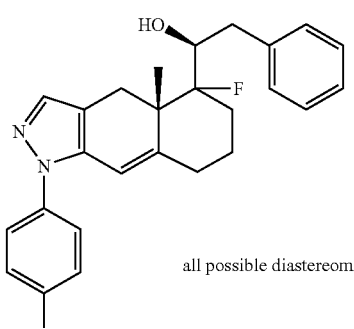
all possible diastereomers Step 1:

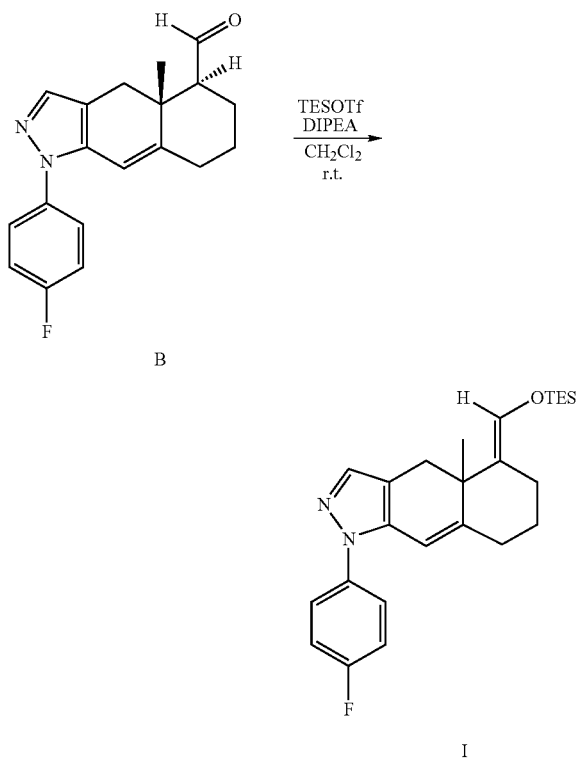

Aldehyde B (105.5 mg, 0.34 mmol) was dissolved in CH$_2$Cl$_2$ (8 mL) and N,N-diisopropylethylamine (1.42 mL, 8.16 mmol) was added followed by TESOTf (1.08 mL, 4.08 mmol). The reaction was stirred at room temperature for 6 h, quenched with 1 mL of isopropyl alcohol and diluted with EtOAc (50 mL). The organic solution was washed with saturated NaHCO$_3$ and brine (10 mL each), dried over Na$_2$SO$_4$, filtered, and concentrated in vacuo. The residue was purified by flash chromatography (15% EtOAc/hexanes) to afford I which was used directly in the next reaction without further characterization.

Step 2:

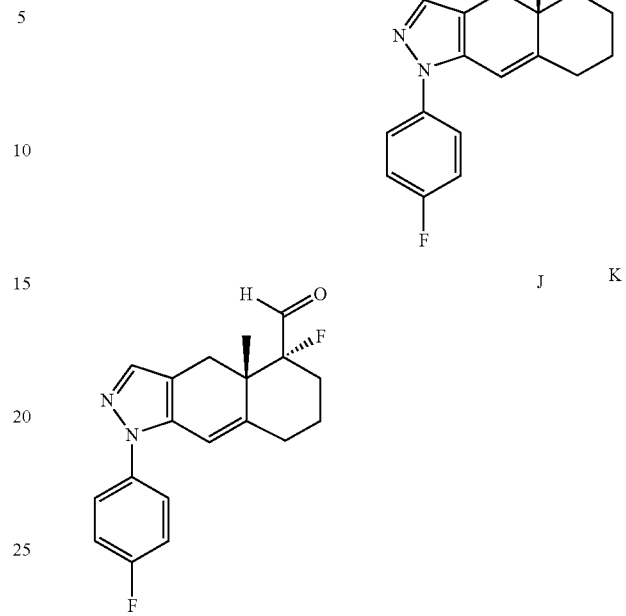

I was dissolved in CH$_2$Cl$_2$ (5 mL) and N-fluorobenzenesulfonimide (536 mg, 1.7 mmol) was added. The reaction was stirred at room temperature for 15 h and then concentrated. The residue was purified by flash chromatography (5 to 15% EtOAc/hexanes) to afford 52.1 mg (47%) of two separable diastereomers, 19.5 mg (18%) of the less polar diastereomer J and 32.6 mg (29%) of the more polar diastereomer K.

Less polar diastereomer J: R$_f$=0.24 (50/42/8 hexanes/CH$_2$Cl$_2$/TIME). LCMS=329; (M+1)$^+$. $^1$H NMR (CDCl$_3$, 500 MHz): δ 9.88 (d, J=7.1 Hz, 1H), 7.42-7.45 (m, 2H), 7.37 (s, 1H), 7.14-7.18 (m, 2H), 6.25 (s, 1H), 2.89 (d, J=16 Hz, 1H), 2.78 (d, J=16 Hz, 1H), 2.53 (m, 1H), 2.33 (br d, J=14 Hz, 1H), 2.06 (m, 1H), 1.97 (m, 1H), 1.83 (m, 1H), 1.69 (m, 1H), 1.32 (d, J=1.4 Hz, 3H).

More polar diastereomer K: R$_f$=0.21 (50/42/8 hexanes/CH$_2$Cl$_2$/TBME). LCMS=329; (M+1)$^+$. $^1$H NMR (CDCl$_3$, 500 MHz): δ 9.91 (d, J=5.7 Hz, 1H), 7.42-7.45 (m, 3H), 7.16 (t, J=8.6 Hz, 2H), 6.27 (d, J=2.1 Hz, 1H), 3.51 (d, J=15.3 Hz, 1H), 2.44-2.52 (m, 2H), 2.39 (br d, J=15.8 Hz, 1H), 2.10 (m, 1H), 1.76-1.90 (m, 2H), 1.30 (m, 1H), 1.18 (s, 3H).

Step 3:

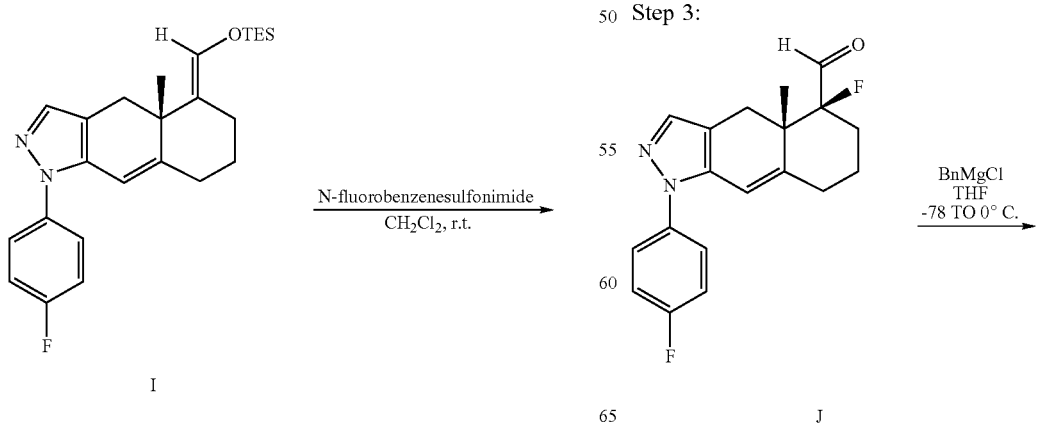

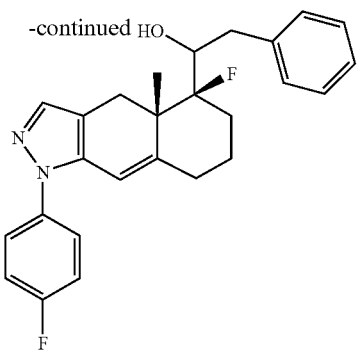

Example 82

Fluoroaldehyde diastereomer J (17.6 mg, 0.054 mmol) was dissolved in THF (2 mL) and cooled to −78° C. BnMgCl (536 μL of a 1 M solution in Et$_2$O, 0.536 mmol) was added dropwise by syringe. The reaction was warmed to 0° C. for 10 min and then quenched with isopropyl alcohol (500 μL) and poured into saturated NH$_4$Cl (10 mL). The mixture was extracted with EtOAc (50 mL). The organic layer was washed with H$_2$O and brine (15 mL each), dried over Na$_2$SO$_4$, filtered and concentrated in vacuo. The residue was purified by flash chromatography (5 to 15% EtOAc/hexanes) to give 5.3 mg (24%) of a less polar diastereomer of Example 82 and 3.8 mg (17%) of a more polar diastereomer of Example 82.

Less polar diastereomer of Example 82: R$_f$=0.40 (25% EtOAc/hexanes, 2 elutions). LCMS=421; (M+1)$^+$. $^1$H NMR (CDCl$_3$, 500 MHz) δ 7.41-7.44 (m, 2H), 7.38 (s, 1H), 7.31-7.34 (m, 2H), 7.24-7.26 (m, 3H), 7.12-7.16 (m, 2H), 6.14 (s, 1H), 4.21 (t, J=9.5 Hz, 1H), 3.19 (d, J=16.0 Hz, 1H), 3.11 (d, J=13.3 Hz, 1H), 7.75 (dd, J=13.5, 10.5 Hz, 1H), 2.67 (d, J=16.0 Hz, 1H), 2.61 (m, 1H), 2.30 (m, 1H), 2.16 (m, 1H), 1.97-2.12 (m, 2H), 1.81 (m, 1H), 1.26 (d, J=2.5 Hz, 3H).

More polar diastereomer of Example 82: R$_f$=0.37 (25% EtOAc/hexanes, 2 elutions). LCMS=421; (M+1)$^+$. $^1$H NMR (CDCl$_3$, 500 MHz) δ 7.45 (dd, J=8.5, 4.8 Hz, 2H), 7.42 (s, 3H), 7.33 (t, J=7.4 Hz, 2H), 7.14-7.18 (m, 3H), 6.18 (s, 1H), 4.05 (dd, J=21, 10.5 Hz, 1H), 3.12 (d, J=13.5 Hz, 1H), 2.97 (s, 2H), 2.78 (dd, J=13.5, 10.4 Hz, 1H), 2.69 (m, 1H), 2.24 (m, 1H), 1.89-2.05 (m, 3H), 1.79 (br s, 1H), 1.67 (m, 1H), 1.35 (d, J=3 Hz, 1H).

The two other possible diastereomers of 82 were prepared in similar manner from the more polar fluoroaldehyde diastereomer K.

Example 83 and 84

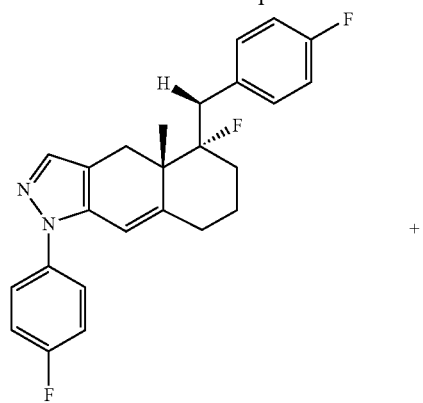

83

+

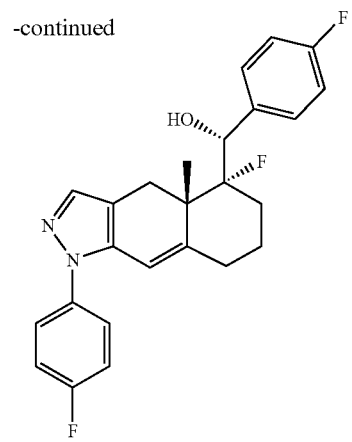

84

Step 1: Addition of Grignard Reagents to Fluoroaldehyde K

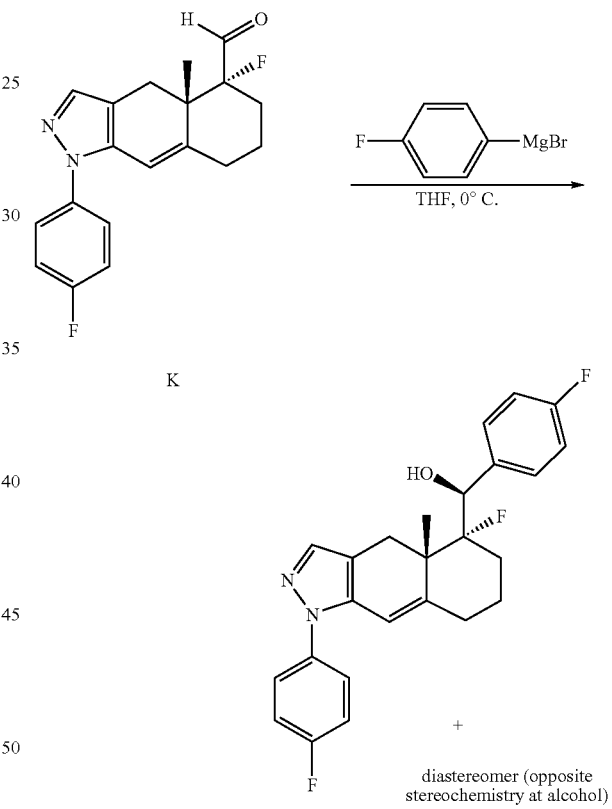

K

+ diastereomer (opposite stereochemistry at alcohol)

Fluoroaldehyde K (28.7 mg, 0.0875 mmol) was dissolved in THF (6 mL) and cooled to 0° C. 4-fluorobenzyl magnesium bromide (218 μL of a 2.0 M solution in diethyl ether, 0.438 mmol) was added dropwise by syringe. The reaction was stirred at 0° C. for 1 hour and then quenched with saturated NH$_4$Cl (10 mL). The mixture was extracted with EtOAc (40 mL) and the organic layer was washed with H$_2$O and brine (10 mL each), dried over Na$_2$SO$_4$, filtered, and concentrated in vacuo. Purification by flash chromatography (5 to 80% EtOAc/hexanes) yielded a mixture of 2 diastereomers. Further purification by PILC (40/40/20 hexanes/CH$_2$Cl$_2$/Et$_2$O) afforded 18.4 mg (50%) of the less polar diastereomer and 11.1 mg (30%) of the more polar diastereomer.

Less Polar diastereomer: $R_f$=0.20 (25% EtOAc/hexanes). LCMS=425; (M+1)+. 1H NMR (CDCl$_3$, 500 MHz): δ 7.43 (m, 2H), 7.40 (s, 1H), 7.36 (t, J=6 Hz, 2H), 7.13 (t, J=8.4 Hz, 2H), 7.05 (t, J=9 Hz, 2H), 6.17 (s, 1H), 5.20 (s, 1H), 3.36 (d, J=15 Hz, 1H), 2.81 (s, 1H), 2.77 (d, J=15 Hz, 1H), 2.47 (m, 1H), 2.29 (m, 1H), 2.15 (m, 1H), 1.82 (m, 1H), 1.57 (m, 2H), 1.33 (s, 3H).

More Polar diastereomer: $R_f$=0.20 (25% EtOAc/hexanes). LCMS=425; (M+1)+. 1H NMR (CDCl$_3$, 500 MHz): δ 7.43-7.36 (m, 5H), 7.13 (t, J=8.4 Hz, 2H), 7.05 (t, J=9 Hz, 2H), 6.18 (s, 1H), 4.93 (d, J=15.5 Hz, 1H), 3.42 (d, J=16 Hz, 1H), 3.12 (d, J=16 Hz, 1H), 2.52 (m, 1H), 2.36 (m, 1H), 1.90 (m, 1H), 1.66 (m, 1H), 1.03 (s, 3H).

Example 84 and 85

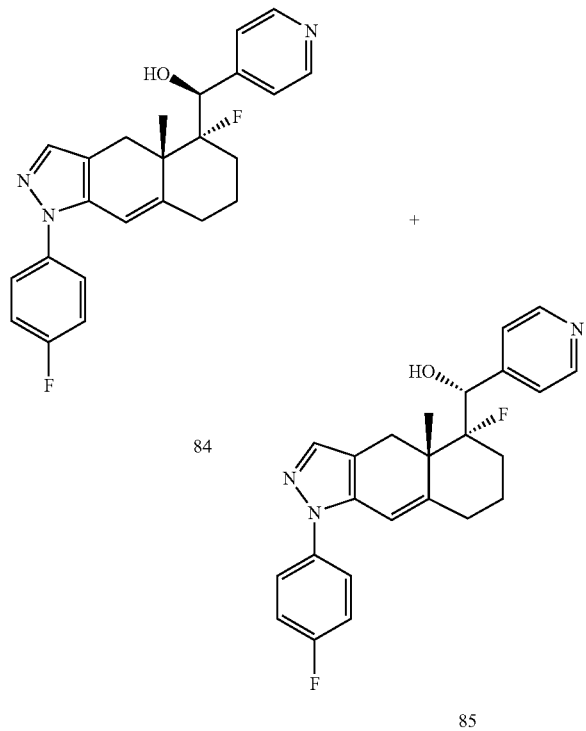

Step 1: Addition of Aryl Lithium to Fluoroaldehyde K.

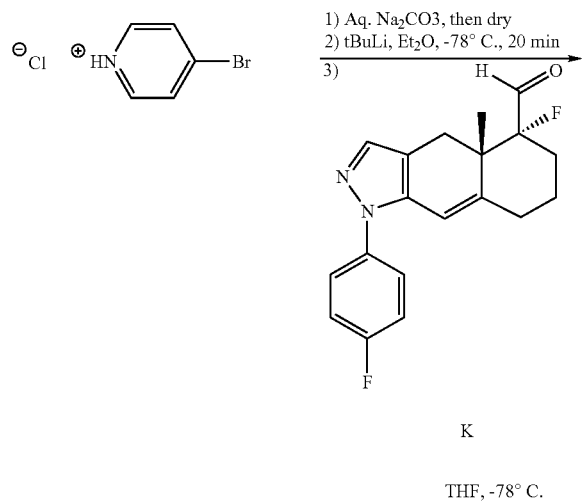

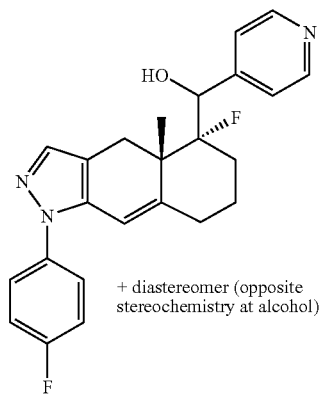

+ diastereomer (opposite stereochemistry at alcohol)

Example 84 + 85

4-bromopyridine HCl (257.9 mg, 1.33 mmol) was dissolved in 5% Na$_2$CO$_3$ (8 mL). The solution was then extracted with Et$_2$O (12 mL) and the Et$_2$O layer was dried over Mg$_2$SO$_4$, filtered, and concentrated to dryness. The residue was azeotroped with benzene (1 mL) and was then dissolved in Et$_2$O (11.2 ml) and cooled to −78° C. t-BuLi (527 μL of a 1.7 M solution in pentanes, 0.973 mmol) was added dropwise by syringe. The reaction was stirred at −78° C. for 20 minutes and then fluoroaldehyde K (29.0 mg, 0.088 mmol) in THF (3 mL) was added by cannula. The reaction was stirred at −78° C. for 45 minutes. 1 mL of isopropyl alcohol was added at −78° C. and then the reaction was poured into saturated NH$_4$Cl (10 mL). The mixture was extracted with EtOAc (50 mL) and the organic layer was washed with water and brine (15 mL each). The organic layer was dried over Na$_2$SO$_4$, filtered, and concentrated in vacuo. Purification by flash chromatography (20 to 100% EtOAc/hexanes) yielded a mixture of 2 diastereomers. Further purification using an AD chiral column (25% IPA/heptanes) afforded 19.1 mg (53%) of peak 1 and 4.8 mg (13%) of peak 2.

Peak 1: $R_f$=0.50 (100% EtOAc). LCMS=408; (M+1)+. 1H NMR (CDCl$_3$, 600 MHz): δ 8.42 (s, 2H), 7.40 (m, 2H), 7.36 (s, 1H), 7.34 (m, 2H), 7.12 (t, J=8.4 Hz, 2H), 6.16 (s, 1H), 3.37 (d, J=16 Hz, 1H), 2.77 (d, J=16 Hz, 1H), 2.46 (m, 1H), 2.20 (m, 2H), 1.52 (m, 3H), 1.18 (s, 3H).

Peak 2: $R_f$=0.50 (100% EtOAc). LCMS=408; (M+1)+. 1H NMR (CDCl$_3$, 600 MHz): δ 8.63 (s, 2H), 7.42 (m, 2H), 7.36 (m, 2H), 7.26 (s, 1H), 7.15 (t, J=8.4 Hz, 2H), 6.29 (s, 1H), 4.92 (d, J=18.6 Hz, 1H), 3.43 (d, J=16 Hz, 1H), 3.13 (d, J=15.6 Hz, 1H), 2.36 (m, 2H), 1.69 (m, 1H), 1.65 (m, 2H), 1.12 (s, 3H).

The following compound was synthesized following procedures analogous to those described for fluoroaldehyde K and beginning from aldehyde F:

| Compound | Molecular structure | LCMS (M + 1)+ |
|---|---|---|
| L | 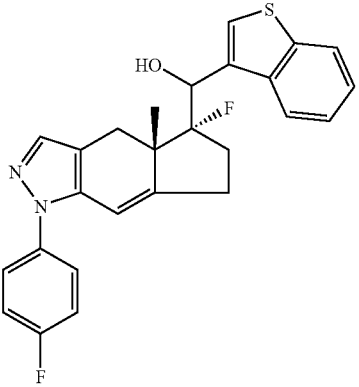 | 315 |

Example 86

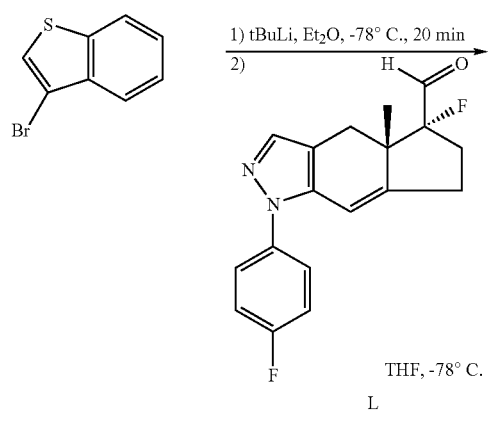

Step 1: Addition of Aryl Lithium to Fluoroaldehyde L.

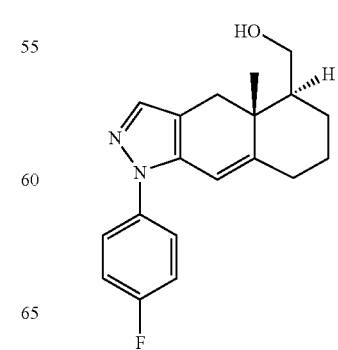

-continued

Example 86

A solution of 3-Bromothianapthene (113.3 μL, 0.866 mmol) in Et$_2$O (8 mL) was cooled to −78° C. and t-BuLi (1.01 mL of a 1.7 M solution in pentanes, 1.73 mmol) was added dropwise by syringe. The reaction was stirred at −78° C. for 20 minutes and then fluoroaldehyde L (27.2 mg, 0.0866 mmol) in TBF (2 mL) was added by cannula. The reaction was stirred at −78° C. for 45 minutes. 1 mL of isopropyl alcohol was added at −78° C. and then the reaction was poured into saturated NH$_4$Cl (10 mL). The mixture was extracted with EtOAc (50 mL) and the organic layer was washed with water and brine (15 mL each). The organic layer was dried over Na$_2$SO$_4$, filtered, and concentrated in vacuo. Purification by flash chromatography (5 to 20% EtOAc/hexanes) followed by PTLC (20/40/40 hexanes/CH$_2$Cl$_2$/Et$_2$O) followed by an AD chiral column (25% IPA/heptanes) afforded 1.6 mg (4%) of example 86: R$_f$=0.43 (60% EtOAc/hexanes). LCMS=449; (M+1)$^+$. $^1$H NMR (CDCl$_3$, 500 MHz): δ 7.95 (d, J=7.8 Hz, 1H), 7.90 (d, J=8.4 Hz, 1H), 7.65 (s, 1H), 7.42 (m, 4H), 7.15 (t, J=8.4 Hz, 2H), 6.27 (s, 1H), 5.38 (dd, J=5.4 Hz, 22.2 Hz, 1H), 3.38 (d, J=16.2 Hz, 1H), 3.06 (d, J=16.2 Hz, 1H), 2.58 (m, 2H), 2.04 (m, 1H), 1.73 (m, 1H), 1.36 (s, 3H).

Example 87

Step 1:

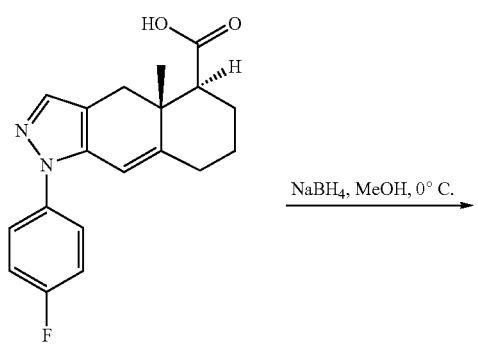

B

NaBH₄, MeOH, 0° C.

Step 1

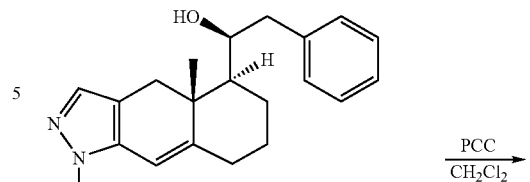

Example 22

PCC
CH₂Cl₂

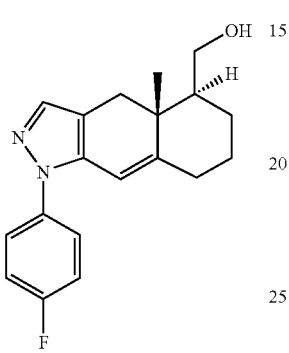

Example 87

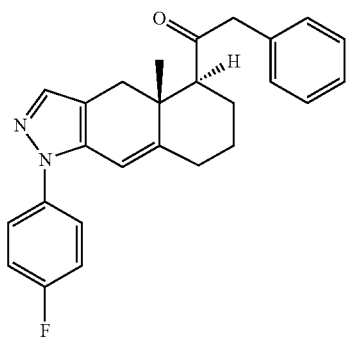

Example 88

Aldehyde B (19.7 mg, 0.0635 mmol) was dissolved in MeOH (2 mL), and the solution was cooled to 0° C. NaBH₄ (12 mg, 0.317 mmol) was added and the reaction was stirred at 0° C. for 30 min. 1 mL of saturated NH₄Cl was added to quench the reaction, and the mixture was extracted with EtOAc (25 mL). The organic layer was washed with H₂O and brine (10 mL each), dried over Na₂SO₄, filtered and concentrated in vacuo. The residue was purified by flash chromatography (5 to 30% EtOAc/hexanes) to afford 13.2 mg (67%) of 87 as a white solid (9:1 ratio of diastereomers). R_f=0.13 (25% EtOAc/hexanes). LCMS=313; (M+1)⁺. ¹H NMR (major diastereomer) (CDCl₃, 500 MH) δ 7.43-7.47 (m, 2H), 7.40 (s, 1H), 7.15 (t, J=8.5 Hz, 1H), 6.12 (d, J=1.9 Hz, 1H), 3.91 (dd, J=10.5, 3.9 Hz, 1H), 3.51 (dd, J=10.0, 8.9 Hz, 1H), 2.96 (d, J=15.5 Hz, 1H), 2.66 (d, J=15.5 Hz, 1H), 2.30-2.42 (m, 2H), 2.02 (m, 1H), 1.89 (m, 1H), 1.66 (m, 1H), 1.34-1.45 (m, 2H), 0.95 (s, 3H).

Example 88

Example 22 (9.5 mg, 0.0236 mmol) was dissolved in CH₂Cl₂ (1 mL) and PCC (15.2 mg, 0.0708 mmol) was added. The reaction was stirred at room temperature for 1 hr and then diluted with hexanes (2 mL) and filtered through a plug of silica gel with 40% EtOAc/hexanes. The filtrate was concentrated and the residue was purified by preparatory thin layer chromatography (25% EtOAc/hexanes) to afford 5.0 mg (53%) of Example 88 as a white solid. R_f=0.27 (25% EtOAc/hexanes). LCMS=401; (M+1)⁺. ¹H NMR (CDCl₃, 500 MHz) δ 7.42-7.45 (m, 1H), 7.37 (s, 1H), 7.35 (t, J=7.4 Hz, 1H), 7.28 (d, J=7.3 Hz, 1H), 7.22 (d, J=7.1 Hz, 1H), 7.13-7.22 (m, 1H), 6.11 (d, J=2.3 Hz, 1H), 3.81 (d, J=15.3 Hz, 1H), 3.77 (d, J=15.3 Hz, 1H), 2.83 (dd, J=12.5, 3.1 Hz, 1H), 2.76 (d, J=15.2 Hz, 1H), 2.67 (d, J=15.2 Hz, 1H), 2.42 (m, 1H), 2.29 (m, 1H), 1.77-1.89 (m, 2H), 1.67 (m, 1H), 1.35 (m, 1H), 1.20 (s, 3H).

Example 89

Step 1:

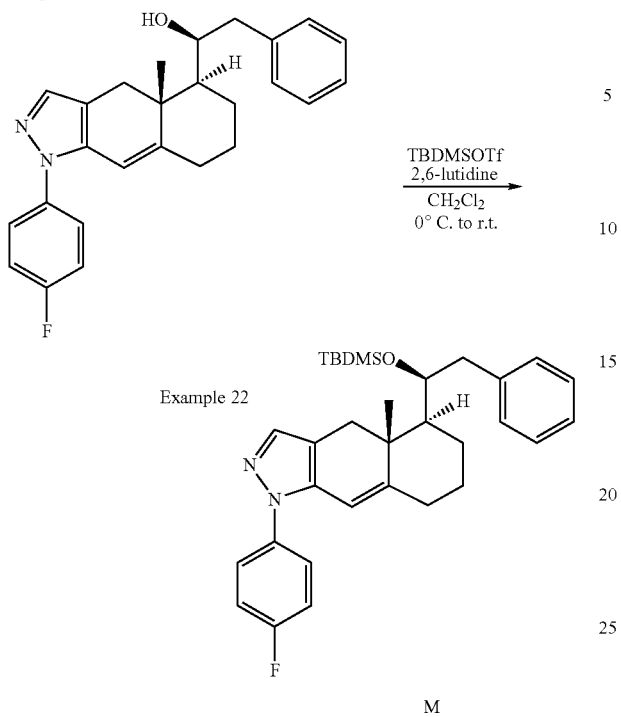

Example 22

Example 22 (165.9 mg, 0.412 mmol) was dissolved in CH$_2$Cl$_2$ (20 mL) and the solution was cooled to 0° C. 2,6-lutidine (265 μL, 2.27 mmol) and TBDMSOTf (142 μL, 0.618 mmol) were added and the reaction was allowed to warm to room temperature. After stirring for 16 h, additional 2,6-lutidine (300 μL, 2.58 mmol) and TBDMSOTf (300 μL, 1.31 mmol) were added to the reaction. The reaction was stirred for an additional 3 h and then quenched with isopropyl alcohol (1 mL). The reaction was diluted with EtOAc (100 mL) and the organic solution was washed with saturated NaHCO$_3$, brine, 1N HCl, saturated NaHCO$_3$, and brine (25 mL of each). The organic layer was dried over Na$_2$SO$_4$, filtered, and concentrated. Purification by flash chromatography (15% TBME/hexanes) gave 207.1 mg (97%) of compound M. R$_f$=0.38 (15% EtOAc/hexanes). $^1$H NMR (CDCl$_3$, 500 MHz) δ 7.37-7.39 (m, 2H), 7.26-7.30 (m, 3H), 7.18 (t, J=7.5 Hz, 1H), 7.10-7.14 (m, 4H), 5.98 (d, J=2.1 Hz, 1H), 4.24 (dd, J=10.5, 4.0 Hz, 1H), 2.96 (dd, J=13.0, 4.0 Hz, 1H), 2.72 (dd, J=13.0, 10.5 Hz, 1H), 2.55 (d, J=15.3 Hz, 1H), 2.35 (m, 1H), 2.22 (bd, J=15.3 Hz, 1H), 1.88 (m, 1H), 1.80 (m, 1H), 1.64-1.73 (m, 2H), 1.44 (dd, J=10.5, 3.0 Hz, 1H), 1.28 (m, 1H), 1.02 (s, 3H), 0.94 (s, 9H), 0.21 (s, 3H), 0.19 (s, 3H).

Step 2:

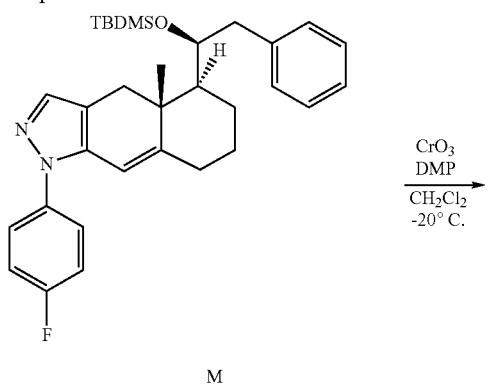

M

CrO$_3$
DMP
———
CH$_2$Cl$_2$
−20° C.

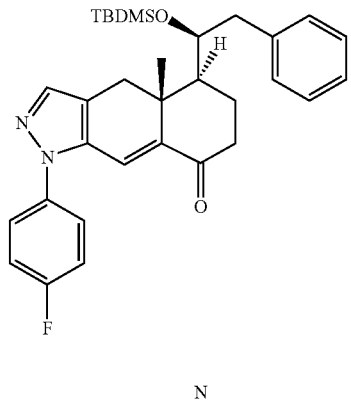

N

CrO$_3$ (550 mg, 5.5 mmol) was placed in a 50 mL round-bottom flask equipped with a stir bar, and 15 mL of dry CH$_2$Cl$_2$ was added. The suspension was cooled to −20° C. and 3,5-dimethylpyrrole (793 mg, 8.25 mmol) was added. The reaction was stirred for 15 min. at −20° C. and compound M (142 mg, 0.275 mmol) was added by cannula in CH$_2$Cl$_2$ (6 mL). The reaction was stirred for 1.5 h while the temperature was maintained between −20 and —15° C. The reaction was then diluted with 100 mL of 3:1 hexanes/Et$_2$O and filtered through a plug of silica gel. The filtrate was concentrated and the residue was purified by flash chromatography with 15% EtOAc/hexanes and then with 2% TBME/toluene to afford 20.8 mg (14%) of compound N. R$_f$=0.29 (15% EtOAc/hexanes). LCMS=531; (M+1)$^+$. $^1$H NMR (CDCl$_3$, 500 MHz) δ 7.44 (s, 1H), 7.39-7.41 (m, 2H), 7.29-7.32 (m, 2H), 7.22 (s, 1H), 7.13-7.21 (m, 5H), 4.33 (dd, J=10.5, 4.0 Hz, 1H), 3.04 (dd, J=13.0, 4.0 Hz, 1H), 2.70-2.79 (m, 3H), 2.32 (m, 1H), 2.01-2.07 (m, 1H), 1.85 (d, J=16.1 Hz, 1H), 1.75 (m, 1H), 1.11 (s, 3H), 0.93 (s, 9H), 0.24 (s, 3H), 0.20 (s, 3H).

Step 3:

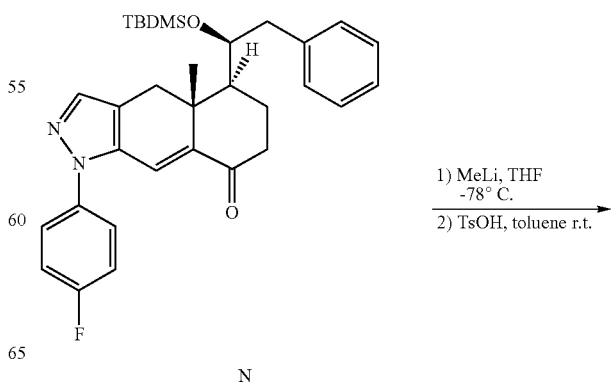

N

1) MeLi, THF
   −78° C.
———————
2) TsOH, toluene r.t.

-continued

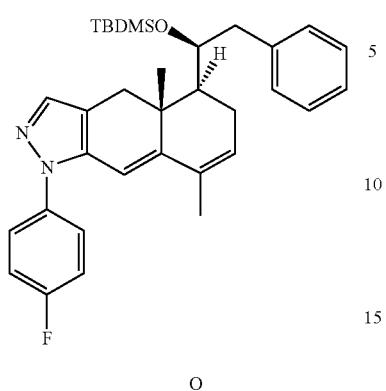

O

Compound N (15.8 mg, 0.0298 mmol) was dissolved in THF (4.5 mL) and the solution was cooled to −78° C. and MeLi (42 μL of a 1.4 M solution in Et$_2$O (0.0596 mmol)) was added dropwise by syringe. The reaction was stirred for 15 min. at −78° C. and then quenched with isopropyl alcohol (100 μL). The cold solution was poured into saturated NH$_4$Cl (10 mL) and the mixture was extracted with EtOAc (50 mL). The organic layer was washed with H$_2$O and brine (15 mL each), dried over Na$_2$SO$_4$, filtered, and concentrated in vacuo. The crude residue (17.0 mg) was dissolved in toluene (2 mL) and p-toluenesulphonic acid monohydrate (5 mg, 0.0263 mmol) was added. The reaction was stirred at room temperature for 15 min. and then diluted with EtOAc (40 mL). The organic solution was washed with saturated NaHCO$_3$ and brine (15 mL of each). The organic layer was dried over Na$_2$SO$_4$, filtered, and concentrated in vacuo. The residue was purified by flash chromatography (15% EtOAc/hexanes) to afford 5.7 mg (36%) of compound O. $R_f$=0.30 (15% EtOAc/hexanes). LCMS=529; (M+1)$^+$. $^1$H NMR (CDCl$_3$, 500 MEz) δ 7.40-7.43 (m, 3H), 7.25-7.28 (m, 21), 7.12-7.18 (m, 51), 6.10 (s, 1H), 5.88 (d, J=5.5 Hz, 1H), 4.40 (dd, J=10.3, 4.1 Hz, 1H), 2.95 (dd, J=13.0, 4.1 Hz, 1H), 2.70-2.75 (m, 2H), 2.61 (m, 1H), 2.25 (dt, J=19.0, 5.0 Hz, 1H), 1.96 (d, J=15.4 Hz, 1H), 1.76 (s, 3H), 1.73 (dd, J=12.5, 4.3 Hz, 1H), 1.04 (s, 3H), 0.94 (s, 9H), 0.20 (s, 6H).

Step 4:

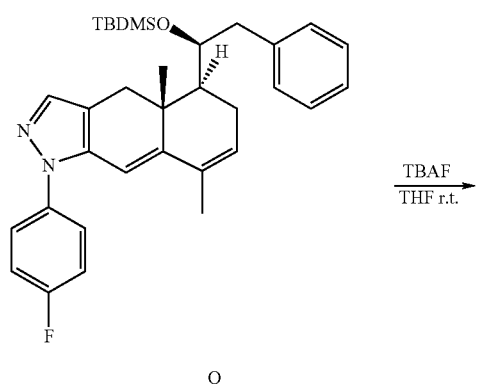

O

TBAF
―――→
THF r.t.

-continued

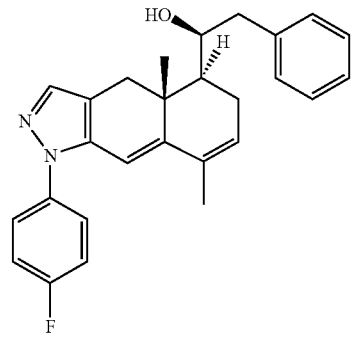

Example 89

Compound O (5.7 mg, 0.0108 mmol) was dissolved in THF (3 mL) and TBAF (150 μL of a 1 M solution in TBF, 0.15 mmol) was added. The reaction was stirred at room temperature for 3 h and then poured into saturated NH$_4$Cl (10 mL). The mixture was extracted with EtOAc (50 mL) and the organic layer was washed with H$_2$O and brine (15 mL each), dried over Na$_2$SO$_4$, filtered, and concentrated in vacuo. The residue was purified by preparatory thin layer chromatography (30% EtOAc/hexanes) to afford 3.5 mg (78%) of Example 89. $R_f$=0.39 (40% EtOAc/hexanes). LCMS=415; (M+1)$^+$. $^1$H NMR (CDCl$_3$, 500 MHz) δ 7.46-7.48 (m, 2H), 7.43 (s, 1H), 7.41 (t, J=7.5 Hz, 2H), 7.23-7.27 (m, 3H), 7.15-7.18 (m, 2H), 6.22 (s, 1H), 5.92 (d, J=5.5 Hz, 1H), 4.31 (m, 1H), 2.97 (d, J=15.4 Hz, 1H), 2.86 (dd, J=13.0, 9.0 Hz, 1H), 2.70 (dd, J=13.0, 5.0 Hz, 1H), 2.63 (m, 1H), 2.48 (d, J=15.1 Hz, 1H), 2.31 (dt, J=18.7, 5.0 Hz, 1H), 1.89 (dd, J=12.3, 4.3 Hz, 1H), 1.83 (s, 3H), 1.14 (s, 3H).

Example 90

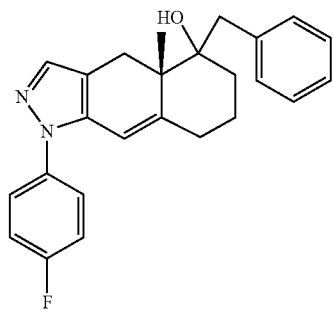

Step 1:

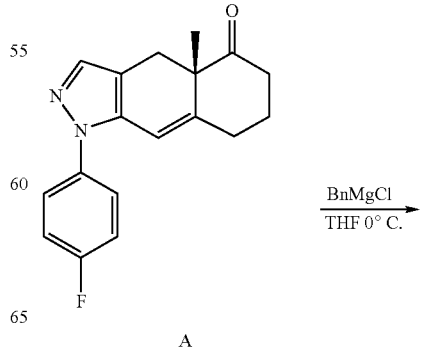

A

BnMgCl
―――→
THF 0° C.

-continued

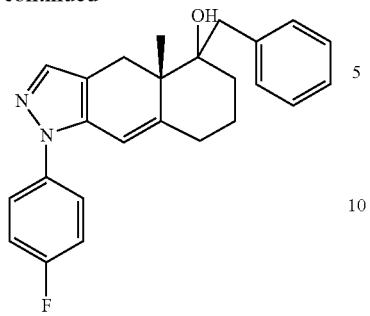

Example 90

Ketone A (18.6 mg, 0.063 mmol) was dissolved in THF and cooled to ° C. BnMgCl (314 µL of a 1 M solution in TBF, 0.314 mmol) was added and the reaction was stirred at 0° C. for 1 hour. Saturated NH₄Cl (1 mL) was added to quench the reaction and the mixture was extracted with EtOAc (40 mL). The organic layer was washed with H₂O and brine (15 mL each), dried over Na₂SO₄, filtered, and concentrated in vacuo. The residue was purified by flash chromatography (5 to 20% EtOAc/hexanes) to afford 14.0 mg (57%) of Example 90. $R_f$=0.21 (25% EtOAc/hexanes). LCMS=389; (14+1)⁺. ¹H NMR (CDCl₃, 500 MHz) δ 7.45-7.48 (m, 2H), 7.38 (s, 3H), 7.15-7.30 (m, 7H), 6.26 (s, 1H), 3.52 (d, J=17.1 Hz, 1H), 2.98 (d, J=14.0 Hz, 1H), 2.86 (d, J=14.0 Hz, 1H), 2.68 (d, J=17.1 Hz, 1H), 2.61 (m, 1H), 2.20 (dd, J=9.0, 4.4 Hz, 1H), 1.61-1.75 (m, 3H), 1.46 (m, 1H), 1.37 (s, 3H).

Example 91

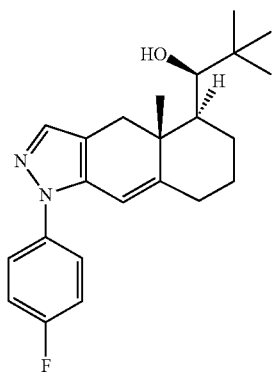

Step 1:

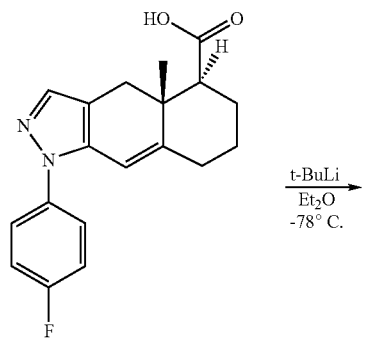

B

-continued

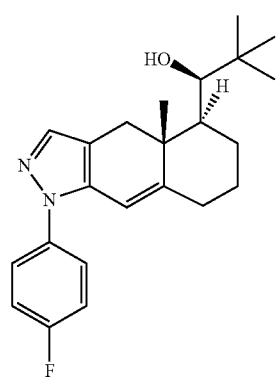

Example 91

A solution of t-BuLi (150 µL of a 1.7 M solution in pentanes, 0.258 mmol) in Et₂O (5 mL) was cooled to −78° C. and aldehyde B (16.0 mg, 0.0516 mmol) was added as a solution in TEF (2 mL). The reaction was allowed to warm slowly to −20° C. and then cooled back to −78° C. The reaction was quenched by the addition of isopropyl alcohol (1 mL) and then poured into saturated NH₄Cl (10 mL). The mixture was extracted with EtOAc (40 mL), and the organic layer was washed with H₂O and brine (15 mL each), dried over Na₂SO₄, filtered, and concentrated in vacuo. The residue was purified by flash chromatography (5 to 20% EtOAc/hexanes) to afford 8.0 mg (42%) of 91. $R_f$=0.24 (25% EtOAc/hexanes). LCMS=369; (M+1)⁺. ¹H NMR (CDCl₃, 500 MHz) δ 7.43-7.46 (m, 2H, 7.41 (s, 1H), 7.14 (t, J=8.5 Hz, 1H), 6.11 (d, J=1.6 Hz, 1H), 3.49 (s, 1H), 2.83 (d, J=15.1 Hz, 1H), 2.45 (d, J=15.1 Hz, 1H), 2.39 (m, 1H), 2.32 (br d, J=14.6 Hz, 1H), 1.59-1.86 (m, 3H), 1.41 (m, 1H), 1.07 (s, 3H), 0.96 (s, 9H).

Example 92

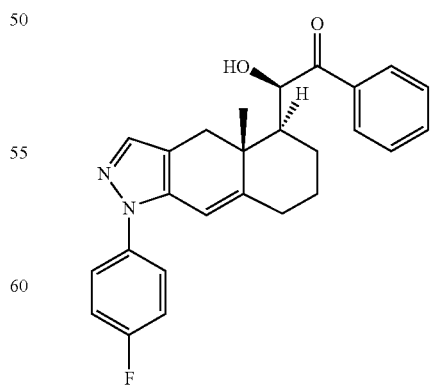

Step 1:

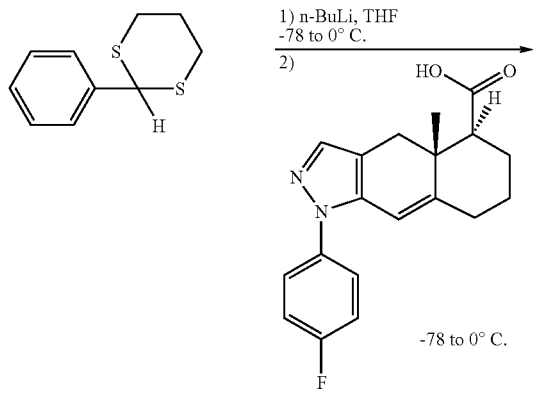

5H), 2.17-2.30 (m, 3H), 1.92-1.96 (m, 2H), 1.58 (m, 1H), 1.37 (qd, J=13.5, 2.0 Hz, 1H), 1.18 (m, 1H), 1.00 (s, 3H), 0.90 (m, 1H).

Step 2:

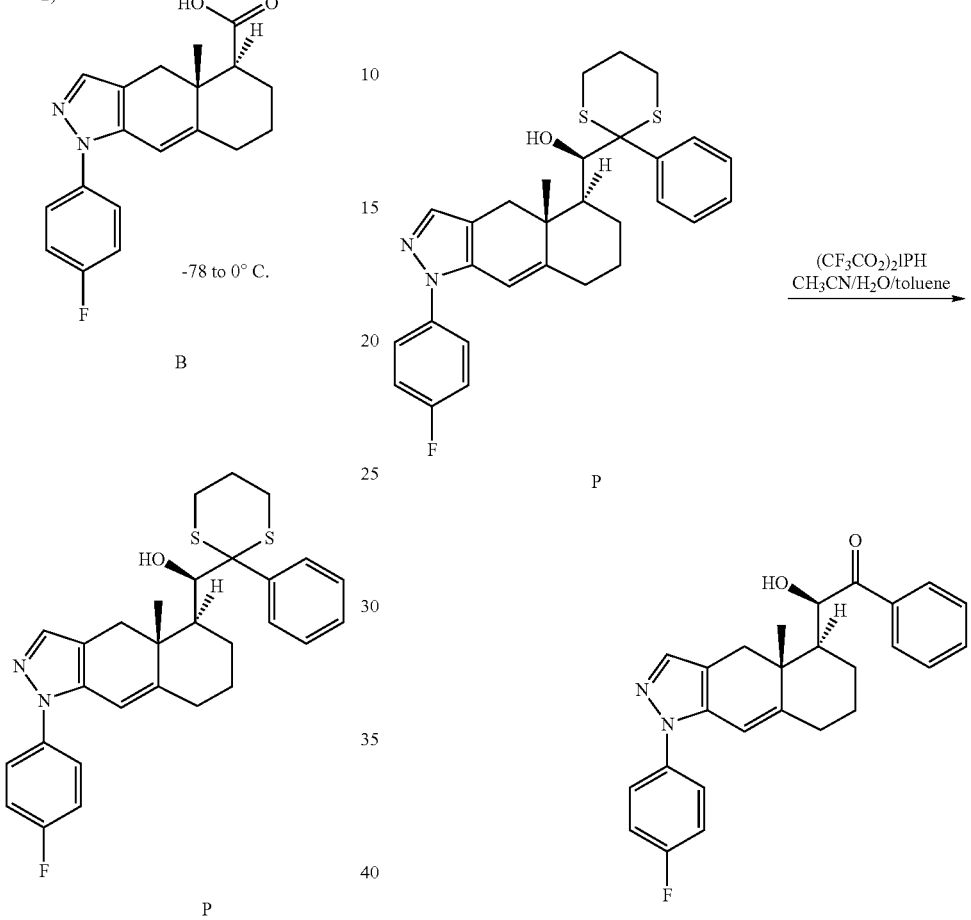

Example 92

2-phenyl-1,3-dithiane (408 mg, 2.08 mmol) was dissolved in THF (8 mL) and cooled to −78° C. n-BuLi (865 μL of a 1.6 M solution in hexanes, 1.38 mmol) was added and the reaction was warmed to 0° C. The reaction was stirred at 0° C. for 30 min. and then cooled back to −78° C. A solution of aldehyde B (53.7 mg, 0.173 mmol) was added in THF (2 mL) by cannula. The reaction was stirred at −78° C. for 10 min. and then warmed to 0° C. and stirred at that temperature for 1 hour. The reaction was quenched with isopropyl alcohol (1 mL) and then poured into saturated NH$_4$Cl (20 mL). The mixture was extracted with EtOAc (50 mL), and the organic layer layer was washed with H$_2$O and brine (20 mL each), dried over Na$_2$SO$_4$, filtered, and concentrated in vacuo. The residue was purified by flash chromatography (5 to 15% EtOAc/hexanes) to afford 54.0 mg (62%) of P. R$_f$=0.23 (25% EtOAc/hexanes). LCMS=507; (M+1)$^+$. $^1$H NMR (CDCl$_3$, 500 MHz) δ 8.04 (d, J=7.6 Hz, 2H), 7.41-7.45 (m, 4H), 7.38 (s, 1H), 7.32 (t, J=7.3 Hz, 1H), 7.13 (m, 2H), 6.04 (d, J=2.1 Hz, 1H), 4.12 (m, 1H), 2.64-2.75 (m, To dithiane P (10.3 mg, 0.020 mmol) was added CH$_3$CN (900 μL), toluene (200 μL), and H$_2$O (100 μL). The biphasic solution was stirred vigorously, and [bis(trifluoracetoxy)iodo]benzene (17.5 mg, 0.041 mmol) was added. After 15 min., an additional portion of [bis(trifluoracetoxy)iodo]benzene (25 mg, 0.058 mmol) was added. The reaction was stirred for an additional 10 min. and then quenched with saturated NaHCO$_3$ (5 mL). The mixture was extracted with EtOAc (40 mL), and the organic layer was washed with brine (10 mL), dried over Na$_2$SO$_4$, filtered and concentrated in vacuo. The residue was purified by preparatory thin layer chromatography to yield 4.4 mg (52%) of 92. R$_f$=0.33 (25% EtOAc/hexanes, 2 elutions). LCMS=417; (M+1)$^+$. $^1$H NMR (CDCl$_3$, 500 MHz) δ 7.90 (d, J=7.1 Hz, 2H), 7.62 (t, J=7.4 Hz, 1H), 7.49-7.63 (m, 3H), 7.42-7.45 (m, 2H), 7.13-7.17 (m, 2H), 6.08 (d, J=2 Hz, 1H), 5.44 (d, J=6.2 Hz, 1H), 3.79 (d, J=6.2 Hz, 1H), 3.30 (d, J=14.6 Hz, 1H), 2.85 (d, J=14.7 Hz, 1H), 2.36 (m, 1H), 2.22 (m, 1H), 1.90 (dd, J=12.5, 2.0 Hz, 1H), 1.76 (m, 1H), 1.70 (dd, J=12.5, 2.0 Hz, 1H), 1.29 (s, 3H), 1.10-1.18 (m, 2H).

93

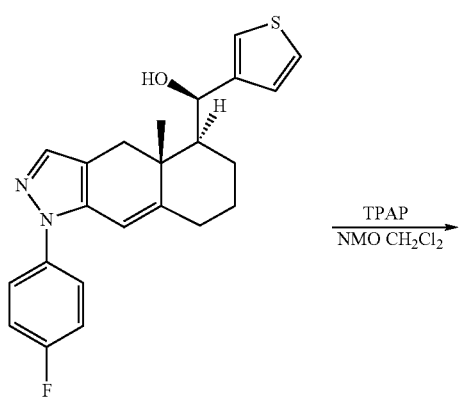

Example 42

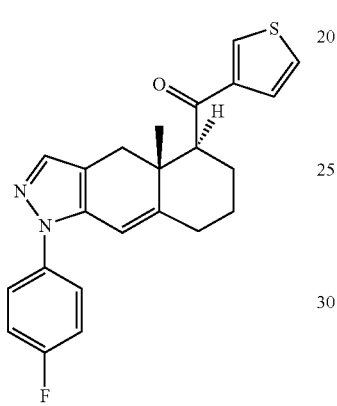

Example 93

Example 42 (50 mg, 0.13 mmol) was dissolved in CH$_2$Cl$_2$ (8 mL) and NMO (22.8 mg, 0.195 mmol) was added. The reaction was stirred at 0° C. for 5 min. and TPAP (4.5 mg, 0.013 mmol) was added. Stirring was continued at 0° C. for an additional 1 h. The reaction was diluted with hexanes (2 mL) and filtered through a plug of silica gel with 10% EtOAc/hexanes to afford 40 mg (80%) of Example 93 as a yellow oil. R$_f$=0.35 (25% EtOAc/hexanes). LCMS=393; (M+1)$^+$.

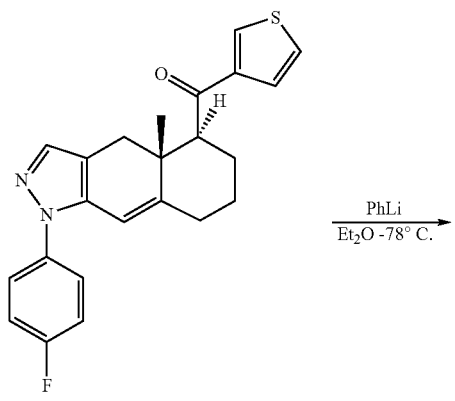

Example 93

94

-continued

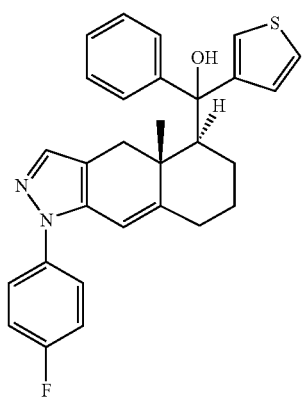

Example 94

Example 93 (20 mg, 0.051 mmol) was dissolved in diethyl ether (5 mL) and the solution was cooled to −78° C. Phenyl lithium (300 μL of a 1.8 M solution in Et$_2$O (0.53 mmol)) was added dropwise by syringe. The reaction was stirred for 1 h at −78° C. and then quenched with isopropyl alcohol (500 μL). The cold solution was poured into saturated NH$_4$Cl (10 mL) and the mixture was extracted with EtOAc (50 mL). The organic layer was washed with H$_2$O and brine (15 mL each), dried over Na$_2$SO$_4$, filtered, and concentrated in vacuo. The residue was purified by reverse-phase HPLC (20% AcCN/H$_2$O) to afford 16 mg (67%) of Example 94 as a single diastereomer. R$_f$=0.20 (30% EtOAc/hexanes). LCMS=471; (M+1)$^+$. $^1$H NMR (CDCl$_3$, 500 MHz) δ 7.61-7.59 (m, 1H), 7.49-7.45 (m, 1H), 7.35-7.27 (m, 1H), 7.32-7.11 (m, 9H), 7.03-7.02 (dd, J=3.5, 4.8 Hz, 1H), 6.13 (br s, 1H), 2.76 (dd, J=3.4, 11.0 Hz, 1H), 2.58 (d, J=16 Hz, 1H), 2.45-2.39 (m, 3H), 2.23 (d, J=16.0 Hz, 1H), 1.04 (s, 3H).

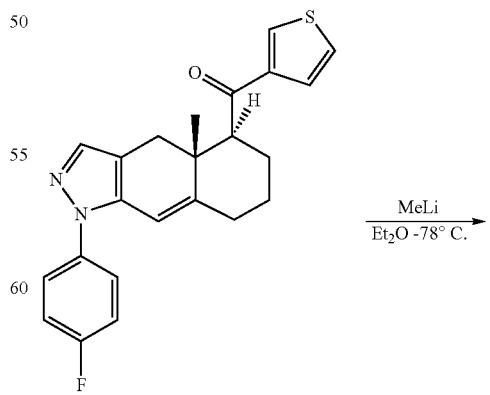

Example 93

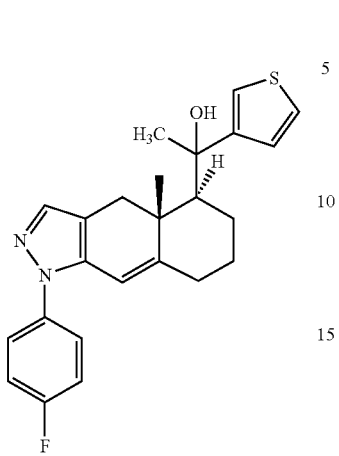

Example 95

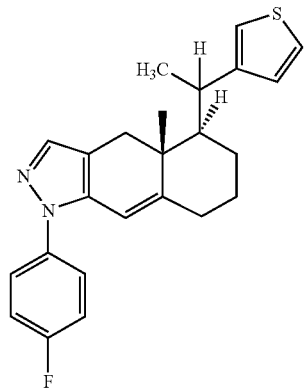

Example 96

Example 93 (20 mg, 0.051 mmol) was dissolved in diethyl ether (5 mL) and the solution was cooled to −78° C. Methyl lithium (760 µL of a 1.4 M solution in Et₂O) was added dropwise by syringe. The reaction was stirred for 3 h at −78° C. and then quenched with isopropyl alcohol (1 mL). The cold solution was poured into saturated NH₄Cl (10 mL) and the mixture was extracted with EtOAc (50 mL). The organic layer was washed with H₂O and brine (15 mL each), dried over Na₂SO₄, filtered, and concentrated in vacuo. The residue was purified by flash chromatography (30% EtOAc/hexanes) to afford 8.8 mg (42%) of Example 95. R$_f$=0.60 (30% EtOAc/hexanes). LCMS=409; (M+1)⁺. ¹H NMR (CDCl₃, 500 MHz) δ 7.48-7.45 (m, 2H), 7.31-7.27 (m, 2H), 7.29-7.14 (m, 1H), 6.13 (br s, 1H), 3.29 (d, J=16 Hz, 1H), 2.70 (d, J=16 Hz, 1H), 2.39-2.28 (m, 2H), 2.08-2.05 (m, 2H), 1.71 (s, 3H), 1.66-1.57 (m, 4H), 1.28 (s, 3).

Example 95 (6.2 mg, 0.015 mmol) was dissolved in dichloromethane (7 mL) and the solution was cooled to 0° C. Boron trifluoride diethyl etherate (19 µL, 0.15 mmol) and triethylsilane (24 µL, 0.15 mmol) were added dropwise by syringe. The reaction was stirred for 1 h at 0° C. and then quenched with saturated NaHCO₃ (2 mL). The solution was poured into H₂O (10 mL) and the mixture was extracted with EtOAc (75 mL). The organic layer was washed with H₂O and brine (15 mL each), dried over Na₂SO₄, filtered, and concentrated in vacuo. The residue was purified by flash chromatography (20% EtOAc/hexanes) to afford 3.5 mg (59%) of Example 96. R$_f$=0.60 (15% EtOAc/hexanes). LCMS=393; (M+1)⁺. ¹H NMR (CDCl₃, 500 MHz) δ 7.47-7.46 (m, 3H), 7.24 (dd, J=4.9, 3.0 Hz, 1H), 7.17-7.14 (m, 3H), 6.13 (br s, 1H), 3.41-3.39 (dq, J=7.3 Hz, 2.3 Hz, 1H), 3.11 (d, J=15.4 Hz, 1H), 2.75 (d, J=15.4 Hz, 1H), 2.32-2.23 (m, 2H), 1.89-1.84 (m, 2H), 1.71 (dt, J=5.4, 2.8 Hz, 1H), 1.41-1.38 (m, 1H), (d, J=7.3 Hz, 3H), 1.33-1.24 (m, 2H), 0.84 (s, 3H).

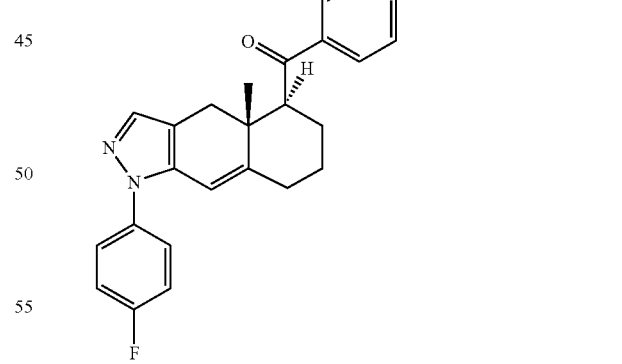

Example 97

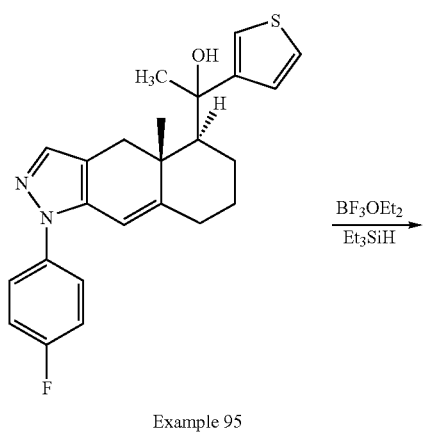

BF₃OEt₂
Et₃SiH

Example 95

Example 35 and IPAP and NMO were processed as in Example 93 to provide the desired compound. R$_f$=0.40 (25% EtOAc/hexanes). LCMS=393; (M+1)⁺. ¹H NMR (CDCl₃, 500 MHz) δ 7.99-7.97 (m, 2H), 7.61-7.59 (m, 1H), 7.52 (t, J=8.5 Hz, 1H), 7.47-7.43 (m, 4H), 7.19 (t, J=8.5 Hz, 1H), 6.19 (br s, 1H), 3.73-3.70 (dd, J=9.6 Hz, 2.7 Hz, 1H), 2.73 (d, J=15.6 Hz, 1H), 2.51-2.40 (m, 2H), 2.38-2.35 (m, 1H), 2.07-1.99 (m, 2H), 1.81-1.77 (m, 1H), 1.27 (s, 3H).

Example 98
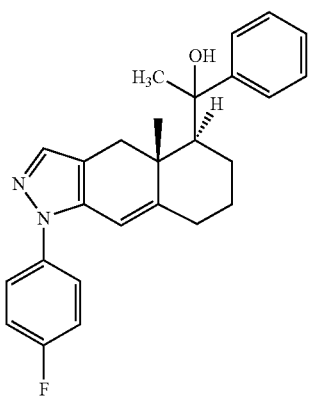
Example 97 and MeLi were processed as in Example 95 to provide the desired compound. $R_f$=0.30 (25% EtOAc/hexanes). LCMS=403; $(M+1)^+$. $^1H$ NMR (CDCl$_3$, 500 MHz) δ 7.53-7.30 (m, 8H), 7.17-7.13 (m, 2H), 6.11 (br s, 1H), 3.16-3.13 (d, J=16 Hz, 1H), 2.65-2.61 (d, J=16 Hz, 1H), 2.47-2.30 (m, 2H), 1.70 (s, 3H), 1.63-1.52 (m, 2H), 1.29 (s, 3H).
The following compounds were synthesized following procedures analogous to those described for examples 93 and 95:
| Compound | Molecular structure | LCMS (M + 1)+ |
|---|---|---|
| 99 |  | 405 |
| 100 |  | 405 |
| 101 | 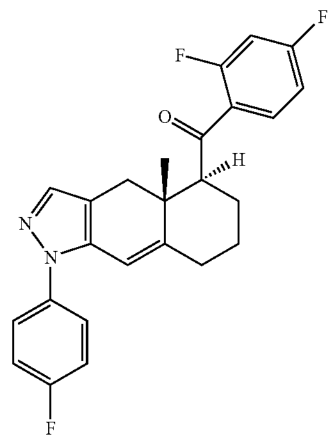 | 423 |
| 102 | 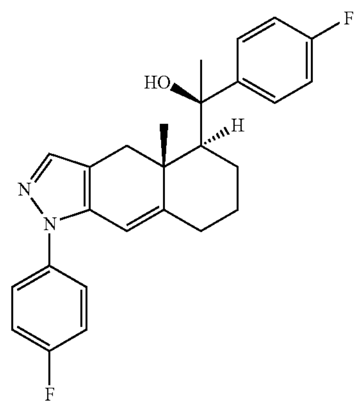 | 421 |
| 103 | 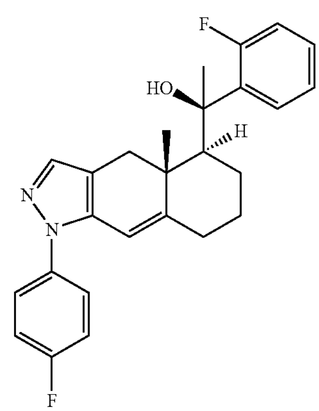 | 421 |

-continued

| Compound | Molecular structure | LCMS (M + 1)+ |
|---|---|---|
| 104 | 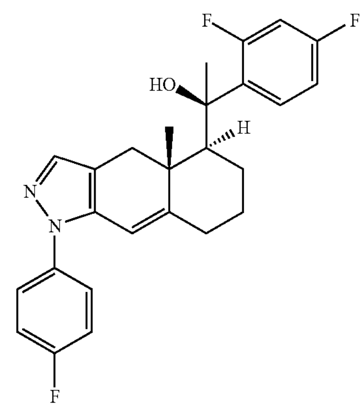 | 439 |

Example 105 and 106

105

106

Step 1: Addition of Grignard Reagents to Aldehyde F

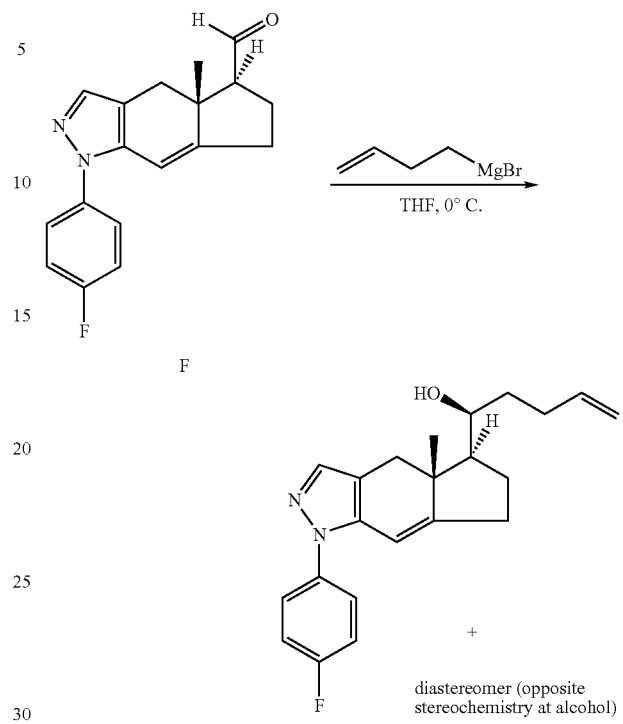

F

+ diastereomer (opposite stereochemistry at alcohol)

Aldehyde F (16.7 mg, 0.0564 mmol) was dissolved in THF (3 mL) and cooled to 0° C. 3-butenyl magnesium chloride (1.1 mL of a 0.5 M solution in THF, 0.564 mmol) was added dropwise by syringe. The reaction was stirred at 0° C. for 1 hour and then quenched with saturated $NH_4Cl$ (10 mL). The mixture was extracted with EtOAc (40 mL) and the organic layer was washed with $H_2O$ and brine (10 mL each), dried over $Na_2SO_4$, filtered, and concentrated in vacuo. The two diastereomeric products were isolated by flash chromatography (5 to 20% EtOAc/hexanes) to afford 9.6 mg (48%) of the less polar diastereomer and 5.0 mg (25%) of the more polar diastereomer. Less Polar diastereomer: $R_f$=0.17 (25% EtOAc/hexanes). LCMS=353; (M+1)+. $^1$H NMR (CDCl$_3$, 500 MHz): δ 7.44-7.47 (m, 2H), 7.40 (s, 1H), 7.14 (t, J=8.5 Hz, 2H), 6.13 (s, 1H), 5.88 (m, 1H), 5.10 (dd, J=17, 1.4 Hz, 1H), 5.02 (d, J=10.3 Hz, 1H), 3.77 (m, 1H), 2.85 (d, J=15.3 Hz, 1H), 2.61 (m, 1H), 2.57 (d, J=15.3 Hz, 1H), 2.42 (m, 1H), 2.29 (m, 1H), 2.20 (m, 1H), 2.05 (m, 1H), 1.81-1.91 (m, 2H), 1.72 (m, 1H), 1.60 (m, 1H), 1.00 (s, 3H).

More Polar diastereomer: $R_f$=0.12 (25% EtOAc/hexanes). LCMS=353; (M+1)+. $^1$H NMR (CDCl$_3$, 500 MHz): δ 7.45-7.48 (m, 2H), 7.39 (s, 1H), 7.14 (t, J=9.0 Hz, 2H), 6.13 (s, 1H), 5.88 (m, 1H), 5.09 (dd, J=17, 1.4 Hz, 1H), 5.01 (d, J=10.0 Hz, 1H), 3.71 (m, 1), 3.13 (d, J=15.3 Hz, 1H), 2.65 (d, J=15.3 Hz, 1H), 2.60 (m, 1H), 2.45 (m, 1H), 2.29 (m, 1H), 2.19 (m, 1H), 1.83-1.91 (m, 2H), 1.72 (m, 1H), 1.45-1.56 (m, 2H), 1.04 (s, 3H).

The following compounds were synthesized following procedures analogous to those described for examples 105 and 106:

| Compound | Molecular structure | LCMS (M + 1)+ |
|---|---|---|
| 107 | 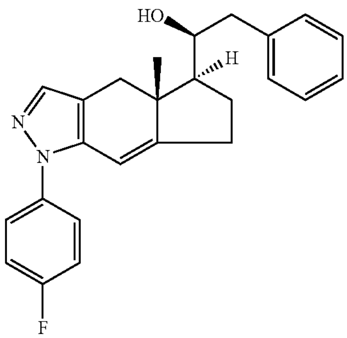 | 389 |
| 108 | 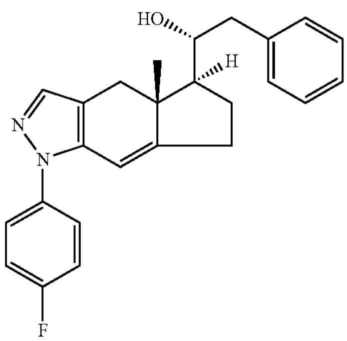 | 389 |
| 109 | 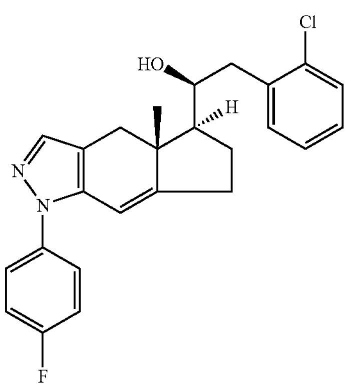 | 423 |
| 110 | 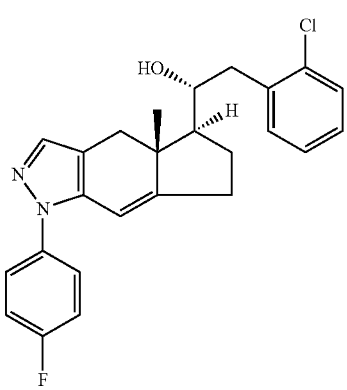 | 423 |

| Compound | Molecular structure | LCMS (M + 1)+ |
|---|---|---|
| 111 | | 425 |
| 112 | | 425 |
| 113 | | 403 |

-continued

| Compound | Molecular structure | LCMS (M + 1)+ |
|---|---|---|
| 114 | 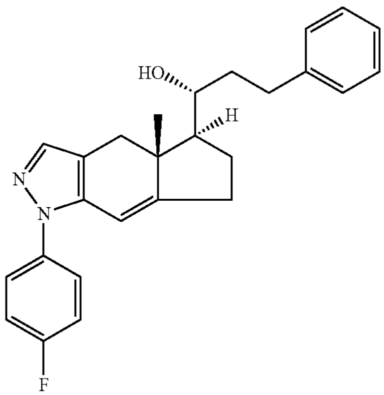 | 403 |

Example 115 and 116

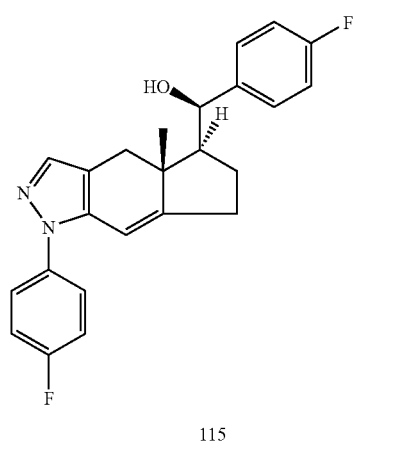

115

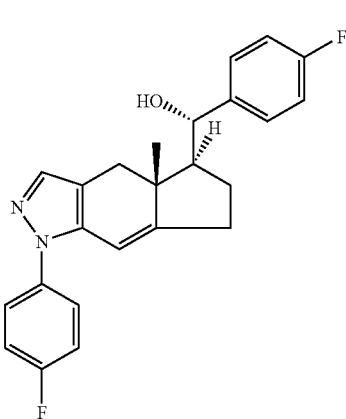

116

Step 1: Addition of Aryl Lithium Reagents to Aldehyde F

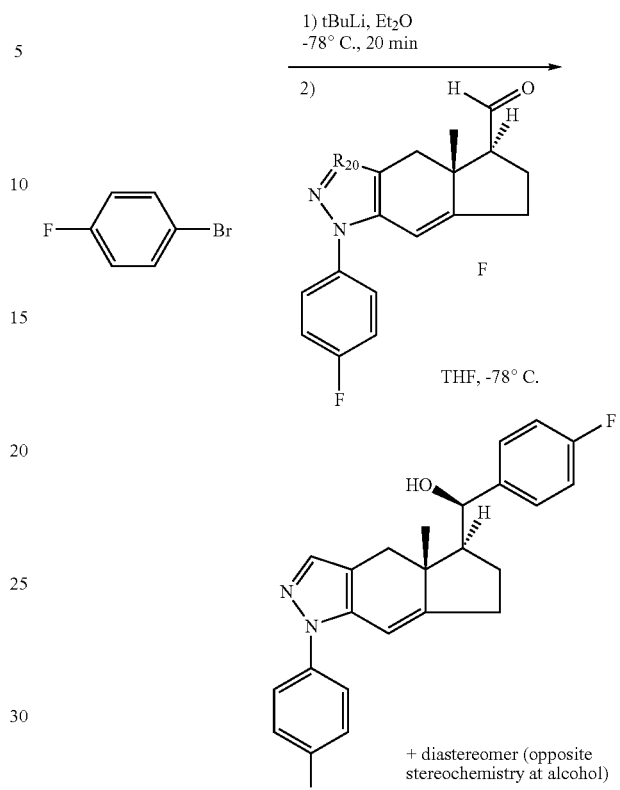

Example 115 + 116

A solution of 1-Bromo-4-fluorobenzene (85 μL, 0.777 mmol) in Et$_2$O (8 mL) was cooled to −780C and tBuLi (914 μL of a 1.7 M solution in pentanes, 1.55 mmol) was added dropwise by syringe. The reaction was stirred at −78° C. for 20 minutes and then aldehyde F (23.0 mg, 0.0777 mmol) in IBF (2 mL) was added by cannula. The reaction was stirred at −78° C. for 45 minutes. 1 mL of isopropyl alcohol was added at −78° C. and then the reaction was poured into saturated NH$_4$Cl (10 mL). The mixture was extracted with EtOAc (50 mL) and the organic layer was washed with water and brine (15 mL each). The organic layer was dried over Na$_2$SO$_4$, filtered, and concentrated in vacuo. Purification by flash chromatography (5 to 20% EtOAc/hexanes) yielded a mixture of 2 diastereomers. Further purification by PTLC (20/60/20 hexanes/CH$_2$Cl$_2$/Et$_2$O) afforded 13.8 mg (45%) of the less polar diastereomer and 9.0 mg (30%) of the more polar diastereomer.

Less Polar diastereomer (115): R$_f$=0.42 (20/60/20 hexanes/CH$_2$Cl$_2$/Et$_2$O). LCMS=393; (M+1)+. $^1$H NMR (CDCl$_3$, 500 Mz): δ 7.36-7.43 (m, 4H), 7.19 (s, 1H), 7.08-7.14 (m, 4H), 6.11 (s, 1H), 4.66 (d, J=8.5 Hz, 1H), 2.63 (m, 1H), 2.45 (m, 1H), 2.22-2.32 (m, 2H), 2.09 (d, J=15.6 Hz, 1H), 1.95 (m, 1H), 1.71 (d, J=15.6 Hz, 1H), 1.00 (s, 3H).

More Polar diastereomer (116): R$_f$=0.20 (20/60/20 hexanes/CH$_2$Cl$_2$Et$_2$O). LCMS=393; (M+1)+. $^1$H NMR (CDCl$_3$, 500 MHz): δ 7.45-7.48 (m, 2H), 7.41 (s, 1H), 7.33-7.36 (m, 2H), 7.12-7.15 (m, 2H), 7.03-7.06 (m, 2H), 6.14 (s, 1H), 4.64 (d, J=10.1 Hz, 1H), 3.25 (d, J=15.8 Hz, 1H), 2.78 (d, J=15.8 Hz, 1H), 2.53 (m, 1H), 2.33 (m, 1H), 2.17 (m, Ii), 1.93 (br s, 1H), 1.46 (m, 1H), 1.23 (m, 1H), 1.17 (s, 3H).

The following compounds were synthesized following procedures analogous to that described for Examples 115 and 116:

| Compound | Molecular structure | LCMS (M + 1)+ |
|---|---|---|
| 117 | 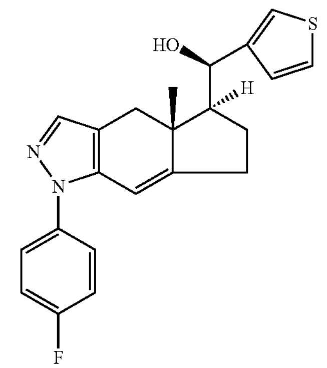 | 381 |
| 118 | 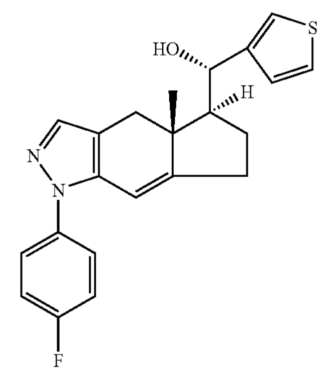 | 381 |
| 119 | 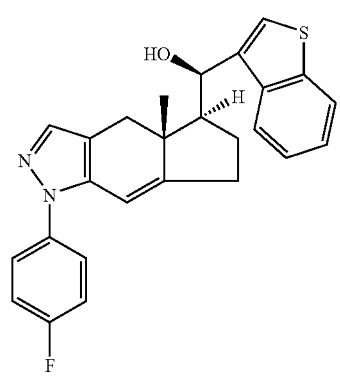 | 431 |
| 120 | 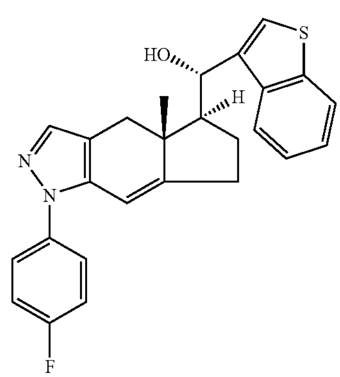 | 431 |
| 121 | | 425 |
| 122 | | 425 |
| 123 | | 425 |

-continued
| Compound | Molecular structure | LCMS (M + 1)+ |
|---|---|---|
| 124 | 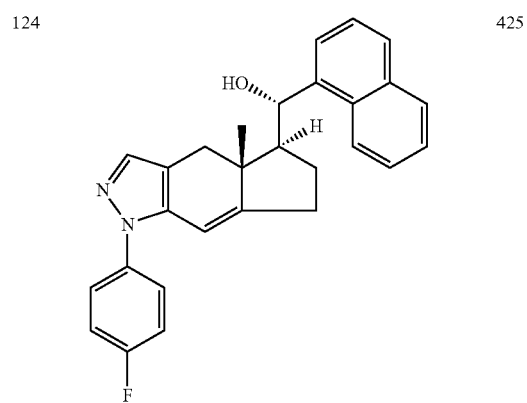 | 425 |
| 125 | 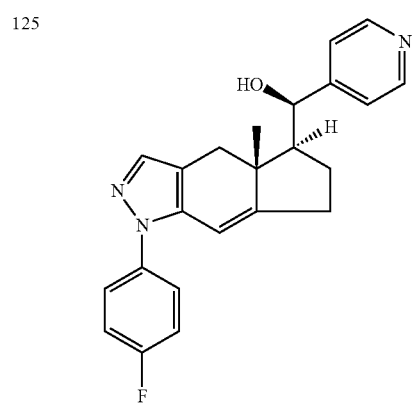 | 376 |
| 126 | 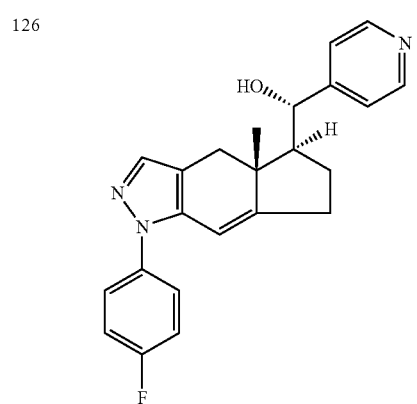 | 376 |
-continued
| Compound | Molecular structure | LCMS (M + 1)+ |
|---|---|---|
| 127 | 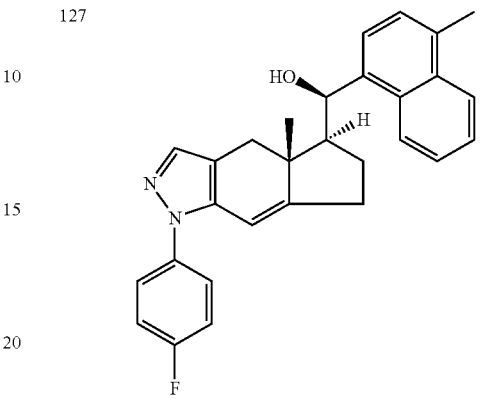 | 439 |
| 128 | 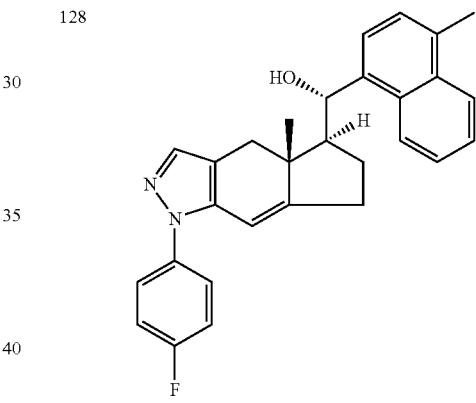 | 439 |
| 129 | 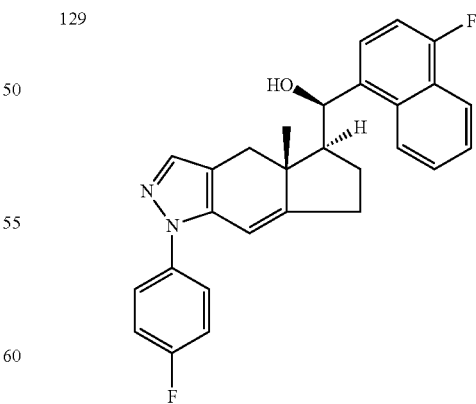 | 443 |

-continued
| Compound | Molecular structure | LCMS (M + 1)+ |
|---|---|---|
| 130 | 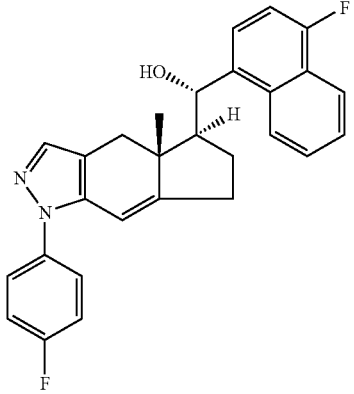 | 443 |
| 131 | 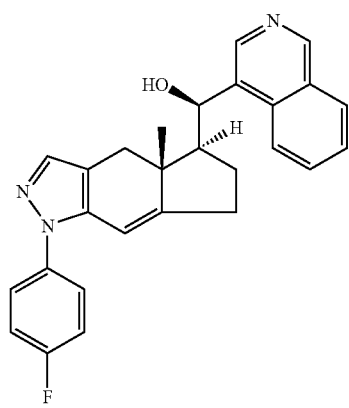 | 426 |
| 132 | 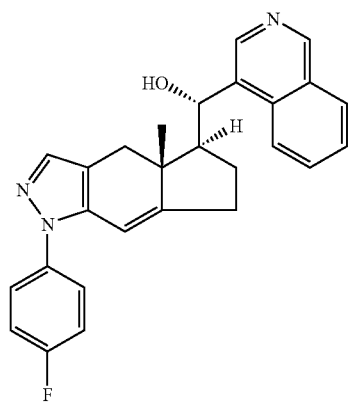 | 426 |
-continued
| Compound | Molecular structure | LCMS (M + 1)+ |
|---|---|---|
| 133 | 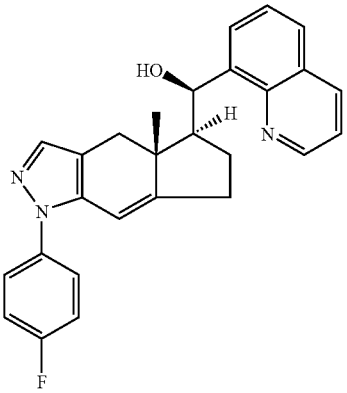 | 426 |
| 134 | 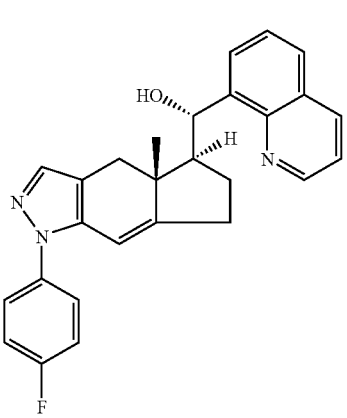 | 426 |
| 135 | 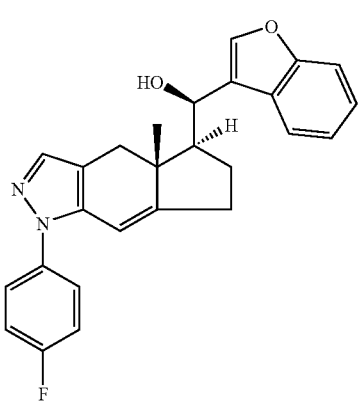 | 415 |

-continued

| Compound | Molecular structure | LCMS (M + 1)+ |
|---|---|---|
| 136 | 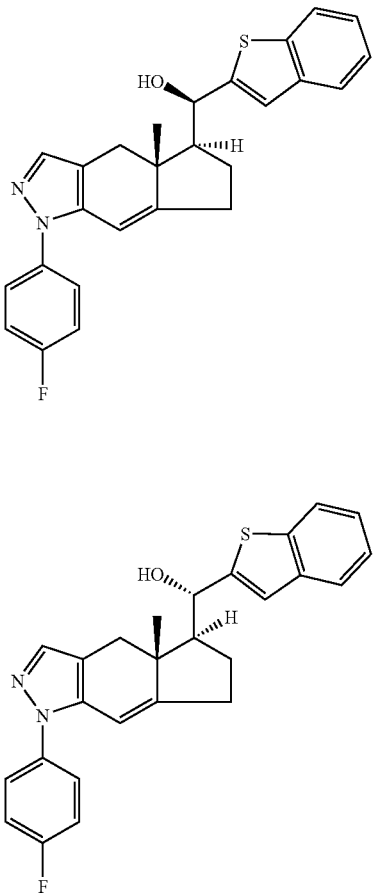 | 415 |

Example 137+138

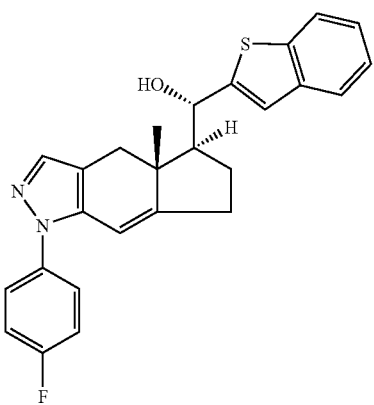

Step 1: Addition of Lithium Reagents Generated by Deprotonation with BuLi to Aldehyde F

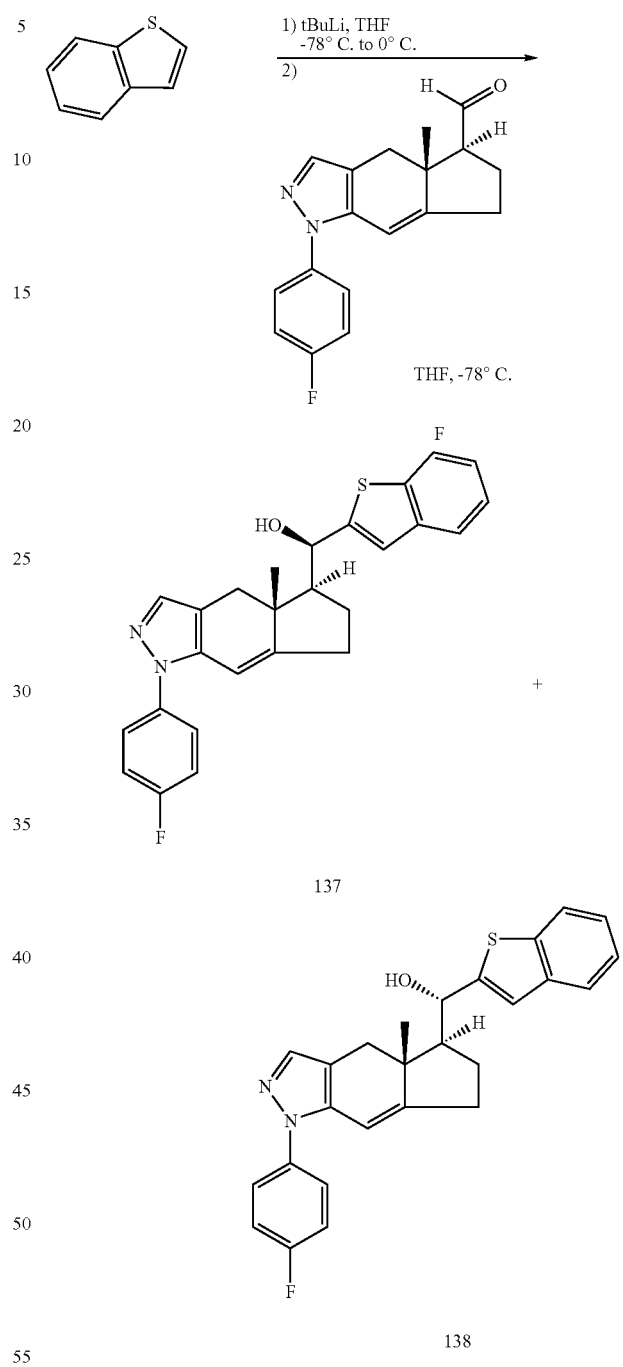

A solution of benzothiophene (403 μL, 3.45 mmol) in TBF (16 mL) was cooled to −78° C. and nBuLi (1.73 JnL of a 1.6 M solution in hexanes, 2.76 mmol) was added dropwise by syringe. The reaction was warmed to 0° C. for 15 minutes and then cooled back to −78° C. Aldehyde F (68.1 mg, 0.230 mmol) in THF (4 mL) was added by cannula and the reaction was stirred at −78° C. for 45 minutes. 1 mL of isopropyl alcohol was added at −78° C. and then the reaction was poured into saturated NH₄Cl (10 mL). The mixture was extracted with EtOAc (50 mL) and the organic layer was washed with water and brine (15 mL each). The organic layer was dried over Na$_2$SO$_4$, filtered, and concentrated in vacuo. Purification of the residue by flash chromatography (5 to 25% EtOAc/hexanes) gave the product as a mixture of diastereomers. The two diastereomers were separated by preparatory TLC in 40/40/20 CH$_2$Cl$_2$/hexanes/Et$_2$O followed by preparatory TLC in 50/50/3 hexanes/CH$_2$Cl$_2$/MeOH. 22.6 mg of 137 (23%) and 28.4 mg of 138 (29%) were isolated.

Characterization for 137: R$_f$=0.18 (25% EtOAc/hexanes). LCMS=431; (M+1)$^+$. $^1$H NMR (CDCl$_3$, 500 M) δ 7.87 (d, J=7.5 Hz, 1H), 7.79 (d, J=7.0 Hz, 1H), 7.35-7.44 (m, 4H), 7.30 (s, 1H), 7.17 (s, 1H), 7.12 (m, 2H), 6.14 (t, J=2 Hz, 1H), 5.07 (dd, J=8.5, 3 Hz, 1H), 2.66 (dd, J=19, 10.5 Hz, 1H), 2.48 (m, 1H), 2.32-2.41(m, 3H), 2.07-2.10 (m, 2H), 1.98 (m, 1H), 1.08 (s, 3H).

Characterization for 138: R$_f$=0.18 (25% EtOAc/hexanes). LCMS=431; (M+1)$^+$. $^1$H NMR (CDCl$_3$, 500 MHz) δ 7.84 (d, J=7.5 Hz, 1H), 7.73 (d, J=7.0 Hz, 1H), 7.47 (m, 2H), 7.42 (s, 1H), 7.33 (m, 2H), 7.23 (s, 1H), 7.14 (m, 2H), 6.16 (t, J=2.0 Hz, 1H) 5.02 (dd, J=10.0, 3.0 Hz, 1H), 3.25 (d, J=15.5 Hz, 1H), 2.81 (d, J=15.5 Hz, 1H), 2.58 (m, 1H), 2.34-2.44 (m, 2H), 2.11 (d, J=3 Hz, 1H), 1.55 (m, 1H), 1.19 (s, 3H).

The following compounds were synthesized following procedures analogous to that described for examples 137 and 138:

| Compound | Molecular structure | LCMS (M + 1)$^+$ |
|---|---|---|
| 139 | 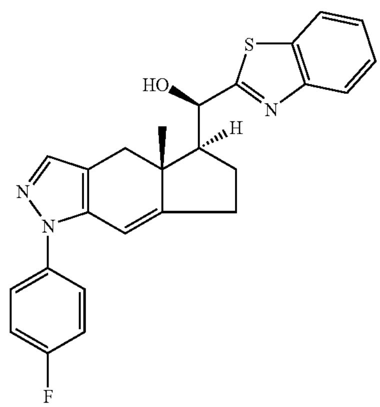 | 432 |
| 140 | 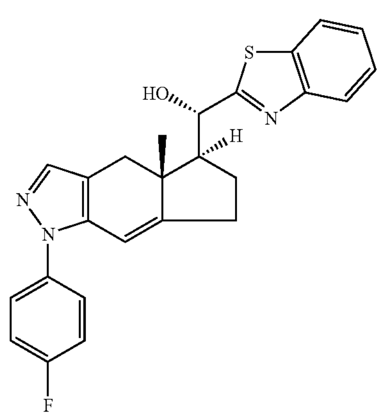 | 432 |
| 141 | | 543 |
| 142 | | 543 |

Example 143

Step 1: Addition of Lithium Reagents Generated by Deprotonation with BuLi to Aldehyde B

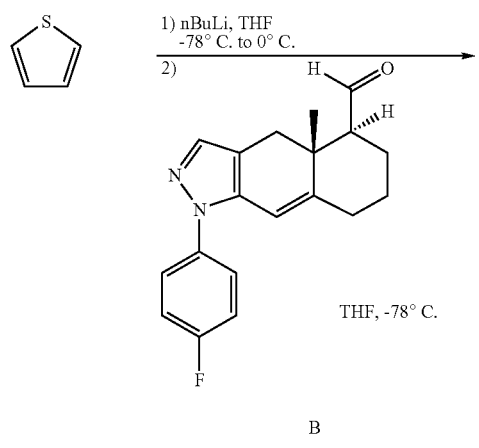

Example 143

A solution of thiophene (82 µL, 1.021 mmol) in THF (8 mL) was cooled to −78° C. and nBuLi (510 µL of a 1.6 M solution in hexanes, 0.816 mmol) was added dropwise by syringe. The reaction was warmed to 0° C. for 15 minutes and then cooled back to −78° C. Aldehyde B (21.1 mg, 0.068 mmol) in THF (2 mL) was added by cannula and the reaction was stirred at −78° C. for 45 minutes. 1 mL of isopropyl alcohol was added at −78° C. and then the reaction was poured into saturated NH$_4$Cl (10 mL). The mixture was extracted with EtOAc (50 mL) and the organic layer was washed with water and brine (15 mL each). The organic layer was dried over Na$_2$SO$_4$, filtered, and concentrated in vacuo. Purification of the residue by flash chromatography (5 to 15% EtOAc/hexanes) afforded 20.5 mg (76%) of 143. R$_f$=0.18 (25% EtOAc/hexanes). LCMS=395; (M+1)$^+$. $^1$H NMR (CDCl$_3$, 500 MHz) δ 7.44-7.46 (m, 2I), 7.43 (s, 1H), 7.22 (dd, J=5.0, 1.0 Hz, 1H), 7.14-7.17 (m, 2H), 6.99 (dd, J=5.0, 3.5 Hz, 1H), 6.95 (d, J=3.5 Hz, 1H), 6.12 (d, J=2.2 Hz, 1H), 5.38 (s, 1H), 3.10 (d, J=15.1 Hz, 1H), 2.70 (d, J=15.1 Hz, 1H), 2.42 (m, 1H), 2.31 (m, 1H), 2.2 (br s, 1H), 1.91 (dd, J=12.3, 3.4 Hz, 1H), 1.88 (m, 1H), 1.70-1.79 (m, 2H), 1.33 (m, 1H), 1.23 (s, 3H).

The following compounds were synthesized following procedures analogous to that described in Example 143:

| Compound | Molecular structure | LCMS (M + 1)$^+$ |
|---|---|---|
| 144 | 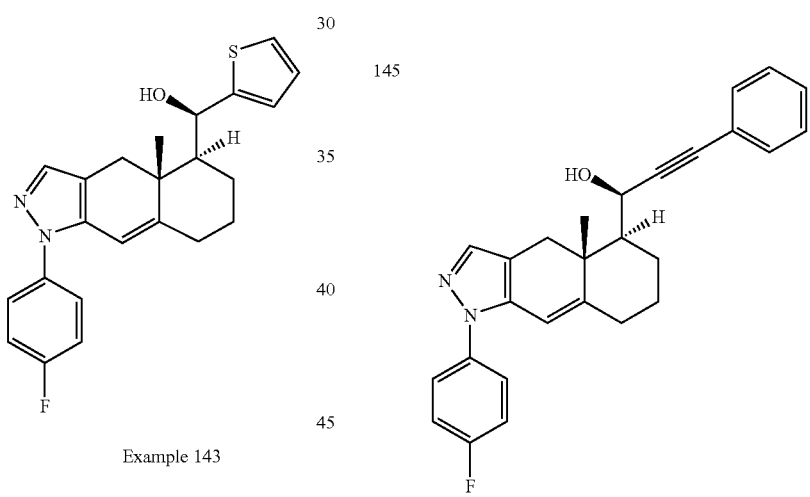 | 445 |
| 145 | 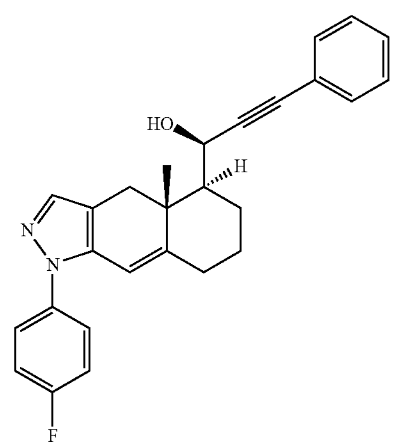 | 413 |
| 146 | 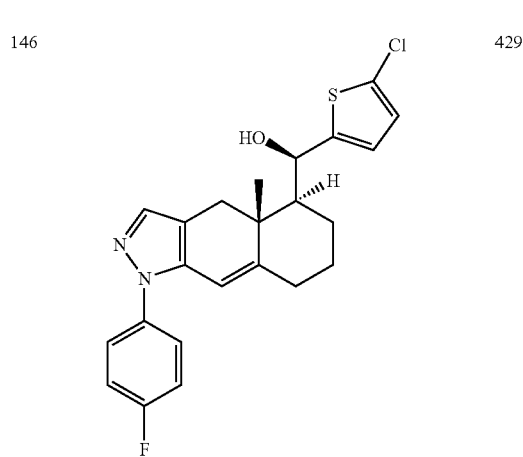 | 429 |

117

-continued

| Compound | Molecular structure | LCMS (M + 1)+ |
|---|---|---|
| 147 | 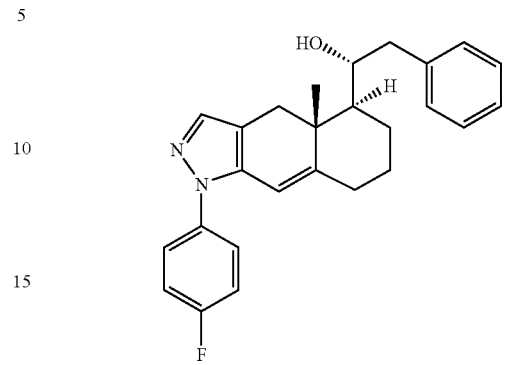 | 396 |

The following compounds were synthesized following procedures analogous to those described for examples 93 and 95 and starting from example 115/116:

| Compound | Molecular structure | LCMS (M + 1)+ |
|---|---|---|
| 148 | 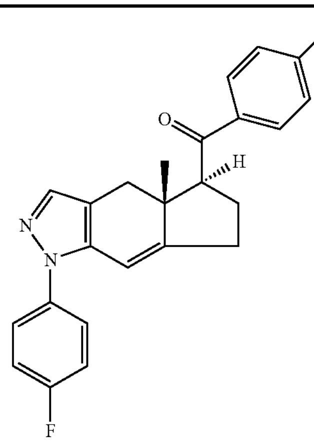 | 391 |
| 149 | 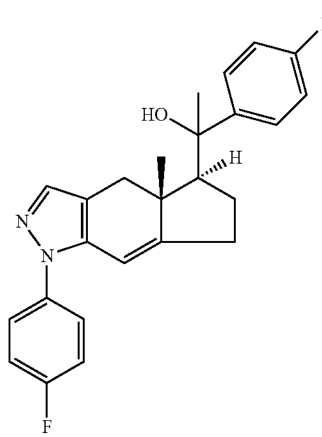 | 407 |

118

Example 150

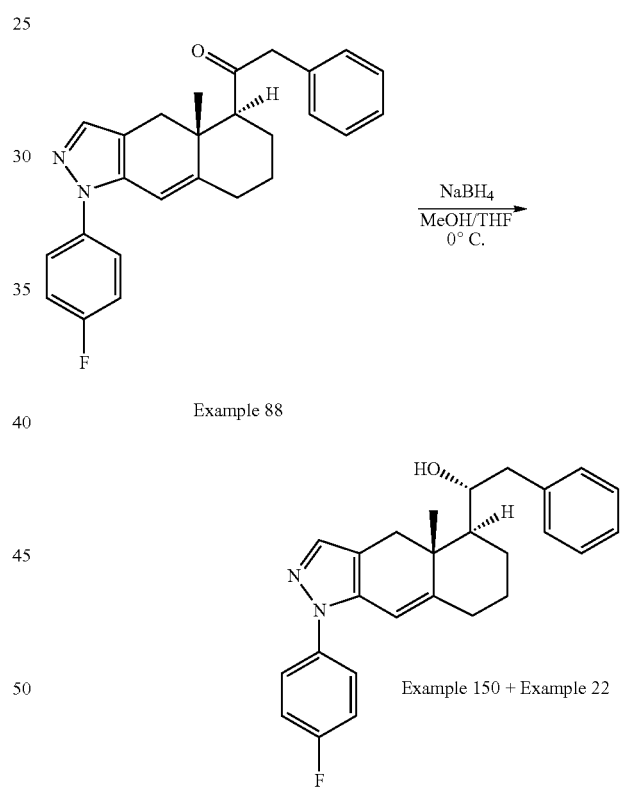

Step 1. Reduction of Ketone

Example 88

Example 150 + Example 22

Example 88 (10.0 mg, 0.025 mmol) was dissolved in THF (1 mL) and MeOH (1 mL) was added. The solution was cooled to 0° C. and NaBH (15 mg, 0.125 mmol) was added. The reaction was stirred at 0° C. for 2 hours and then quenched with saturated $NH_4Cl$ (1 mL). The mixture was extracted with EtOAc (25 mL) and the organic layer was washed with $H_2O$ and brine (5 mL each). The organic layer was dried over $Na_2SO_4$, filtered and concentrated in vacuo. The residue was purified by PTLC to afford 7.9 mg (79%) of alcohol as a 3:1 mixture of diastereomers favoring 150 over 22. Further purification by chiral HPLC (OD column, 35% IPA/heptanes) gave 4.7 mg (47%) of pure 150 (slower eluting isomer). $R_f$=0.23 (25% EtOAc/hexanes). LCMS=403; (M+1)$^+$. $^1$H NMR (CDCl$_3$, 500 MHz) δ 7.45-7.47 (m, 2H), 7.40 (s, 1H), 7.36 (t, J=7.4 Hz, 2H), 7.28 (t, J=7.7 Hz, 3H), 7.14-7.17 (m, 2H), 6.14 (s, 1H), 4.02 (m, 1H), 3.22 (d, J=15.5 Hz, 1H), 3.03 (d, J=12.5 Hz, 1H), 2.71 (d, J=15.5 Hz, 1H), 2.60 (dd, J=13.1, 10.6 Hz, 1H), 2.36 (m, 2H), 2.02 (m, 1H), 1.93 (m, 1H), 1.86 (dt, J=12.4, 3.6 Hz, 1H), 1.39-1.55 (m, 2H), 1.14 (s, 3H).

Example 151 and 152

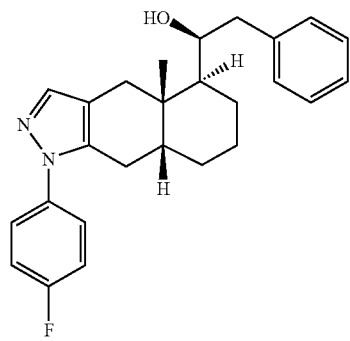

+

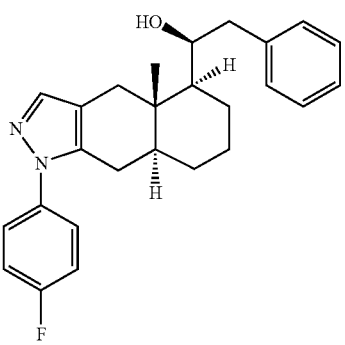

Step 1.

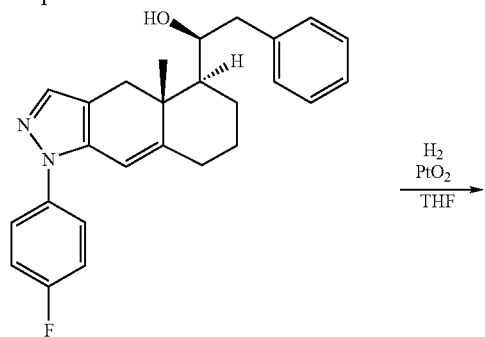

Example 22

-continued

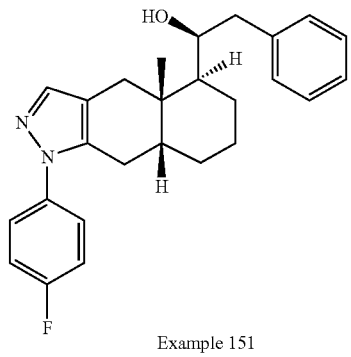

Example 151

+

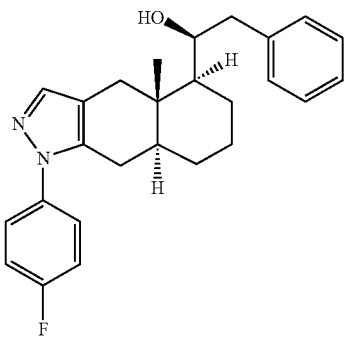

Example 152

Example 22 (21.3 mg, 0.053 mmol) was dissolved in THF (3 mL) and PtO$_2$ (6 mg) was added. The solution was placed under H$_2$ and stirred at room temperature. After 3 hours, the catalyst was filtered off and the filtrate was concentrated. Purification by flash chromatography (5 to 20% EtOAc/hexanes) afforded 7.7 mg (36%) of 151 as a white solid and 9.2 mg (43%) of 152 as a white solid.

151 (Less Polar diastereomer): $R_f$=0.28 (25% EtOAc/hexanes). LCMS=405; (M+1)$^+$. $^1$H NMR (CDCl$_3$, 500 MHz): δ 7.44-7.46 (m, 2H), 7.38 (s, 1H), 7.27 (t, J=7.4 Hz, 2H), 7.19 (t, J=7.4 Hz, 1H), 7.13 (m, 4H), 4.22 (m, 1H), 2.92 (d, J=16.0 Hz, 1H), 2.81 (dd, J=13.3, 8.9 Hz, 1H), 2.72 (dd, J=16.8, 6.2 Hz, 1H), 2.62 (dd, J=13.3, 4.5 Hz, 1I), 2.54 (dd, J=16.9, 6.1 Hz, 1H), 2.15 (d, J=16.0 Hz, 1H), 2.08 (br s, 1H), 1.86 (m, 1H), 1.79 (m, 1H), 1.67-1.72 (m, 2H), 1.59 (m, 1H), 1.28-1.37 (m, 2H), 1.15 (s, 3H).

152 (More Polar diastereomer): $R_f$=0.21 (25% EtOAc/hexanes). LCMS=405; (M+1)$^+$. $^1$H NMR (CDCl$_3$, 500 MHz): δ 7.46-7.48 (m, 2H), 7.42 (s, 1H), 7.35 (t, J=7.6 Hz, 2H), 7.26 (t, J=7.9 Hz, 3H), 7.12-7.15 (m, 2H), 4.26 (m, 1H), 2.90 (dd, J=13.3, 8.6 Hz, 1H), 2.74 (d, J=15.4 Hz, 1H), 2.72 (dd, J=13.3, 5.5 Hz, 1H), 2.53 (dd, J=16.3, 4.8 Hz, 1H), 2.38 (dd, J=16, 12 Hz, 1H), 2.01 (d, J=15.1 Hz, 1H), 1.91 (m, 1H), 1.73 (m, 1H), 1.64 (m, 1H), 1.57 (m, 1H), 1.51 (m, 1H), 1.34-1.43 (m, 2H), 1.29 (m, 1H), 0.95 (s, 3H).

Example 153

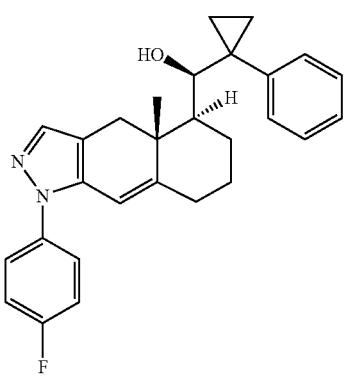

Step 1. Cyclopropanation of the Alkene

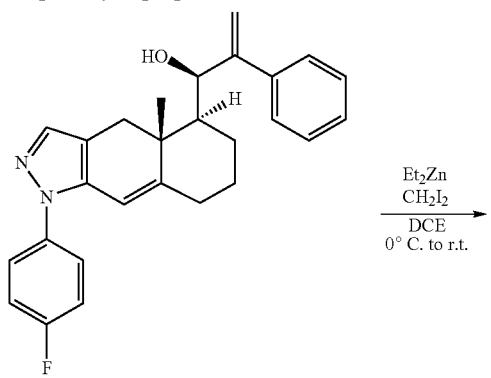

A solution of Et₂Zn (410 µL of a 1 M solution in hexanes, 0.41 mmol) in dichloroethane (1 mL) was cooled to 0° C. and CH₂I₂ (66 µL, 0.821 mmol) was added. The reaction was stirred for 5 minutes and the formation of a white precipitate was observed. A solution of 43 (17.0 mg, 0.041 mmol) in dichloroethane (1 mL) was added by cannula. The reaction was warmed to room temperature and stirred for 1 hour. After this period of time, the reaction was quenched with 1 N HCl (1 mL). The mixture was extracted with EtOAc (50 mL). The organic layer was washed with H₂O, aq. NaHSO₃, saturated NaHCO₃, and brine (15 mL each), dried over Na₂SO₄, filtered, and concentrated in vacuo. Purification of the residue by flash chromatography (5 to 20% EtOAc/hexanes) afforded 10.2 mg (58%) of 153. $R_f$=0.14 (25% EtOAc/hexanes). LCMS=429; (M+1)⁺. ¹H NMR (CDCl₃, 500 MHz) δ 7.37-7.44 (m, 5H), 7.30 (t, J=7.4 Hz, 2H), 7.23 (t, J=7.4 Hz, 1H), 7.12-7.16 (m, 2H), 6.05 (d, J=2.1 Hz, 1H), 3.59 (s, 1H), 2.79 (d, J=15.1 Hz, 1H), 2.19-2.31 (m, 3H), 1.83 (dd, J=12.7, 3.0 Hz, 1H), 1.63 (m, 1H), 1.11-1.34 (m, 1H), 1.04 (s, 3H) 1.00 (m, 1H), 0.89 (m, 1H), 0.83 (m, 1H), 0.78 (m, 1H).

Example 154 was synthesized following procedures analogous to that described for Example 153:

| Compound | Molecular structure | LCMS (M + 1)⁺ |
|---|---|---|
| 154 | 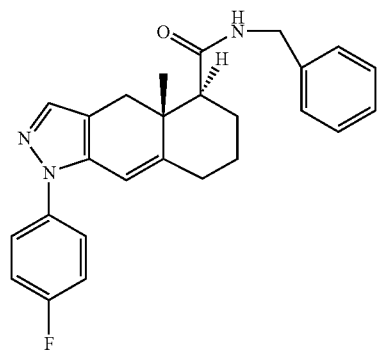<br>from example 16 | 381 |

Example 156

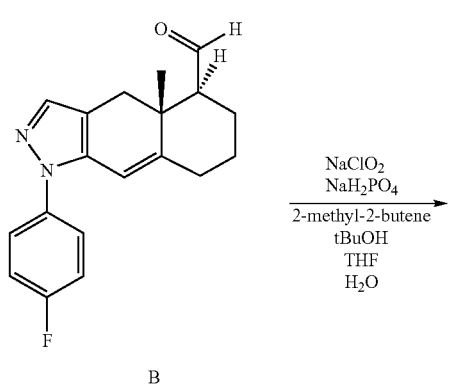

Step 1.

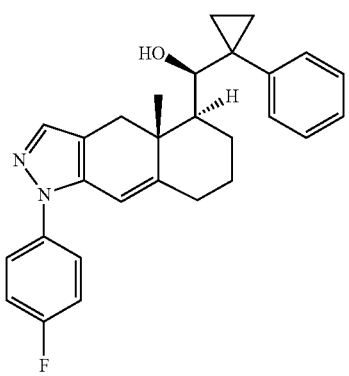

-continued

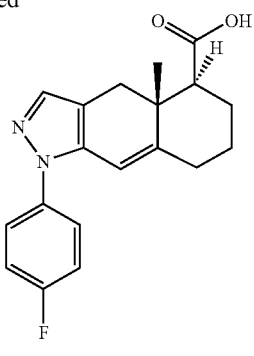

155

To a solution of aldehyde B (35.5 mg, 0.1145 mmol) in THF (200 μL) was added tBuOH (200 μL), 2-methyl-2-butene (200 μL), and a solution of NaClO$_2$ (23 mg, 0.252 mmol) and NaH$_2$PO$_4$ (35 mg, 0.252 mmol) in H$_2$O (250 μL). The reaction was stirred at room temperature for 2 hours and then partitioned between EtOAc and H$_2$O (25 mL of each). The aqueous layer was acidified with 1N HCl and extracted with EtOAc (3×25 mL). All of the organic extracts were combined and washed with brine (25 mL). The organic layer was dried over Na$_2$SO$_4$, filtered and concentrated in vacuo. The residue was purified by flash chromatography (40/60/1 EtOAc/hexanes/HOAc) to afford 33.3 mg (89%) of acid 155. R$_f$=0.22 (40/60/1 EtOAc/hexanes/HOAc). LCMS=327; (M+1)$^+$.

Step 2. Coupling of Carboxylic Acid to Amine

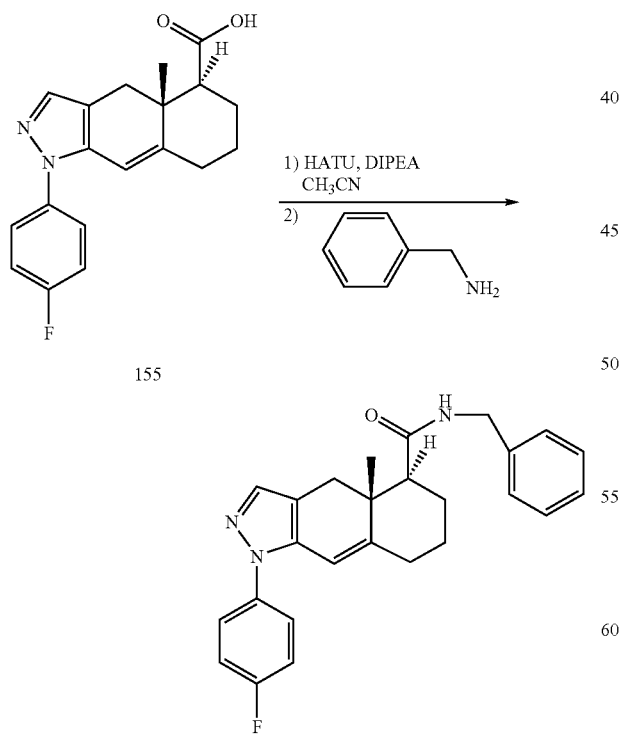

Example 156

To a solution of 155 (10.5 mg, 0.0322 mmol) in CH$_3$CN (0.5 mL) was added DIPEA (23 μL, 0.129 mmol) and HATU (15 mg, 0.0387 mmol). The reaction was stirred at room temperature for 5 minutes and then benzylamine (6 μL, 0.0483 mmol) was added. After 30 minutes, the reaction was diluted with EtOAc (40 mL) and washed with saturated NaHCO$_3$, brine, 1 N HCl, saturated NaHCO$_3$, and brine (10 mL each). The organic layer was dried over Na$_2$SO$_4$, filtered, and concentrated in vacuo. Purification by flash chromatography (20 to 60% EtOAc/hexanes) afforded 9.4 mg (70%) of 156. R$_f$=0.22 (40% EtOAc/hexanes). LCMS=416; (M+1)$^+$. $^1$H NMR (CDCl$_3$, 500 MHz) δ 7.41-7.44 (m, 2H), 7.29-7.38 (m, 6H), 7.12-7.16 (m, 2H), 6.11 (d, J=1.8 Hz, 1H), 5.87 (t, J=5.4 Hz, 1H), 4.47 (m, 2H), 2.81 (d, J=15.3 Hz, 1H), 2.68 (d, J=15.3 Hz, 1H), 2.43 (m, 1H), 2.29 (m, 1H), 2.25 (dd, J=12.7, 3.3 Hz, 1H), 1.97 (qd, J=13, 3.4 Hz, 1H) 1.89 (m, 1H), 1.79 (m, 1H), 1.37 (m, 1H), 1.19 (s, 3H).

Example 157 was synthesized following procedures analogous to that described for Example 156:

| Compound | Molecular structure | LCMS (M + 1)$^+$ |
|---|---|---|
| 157 | 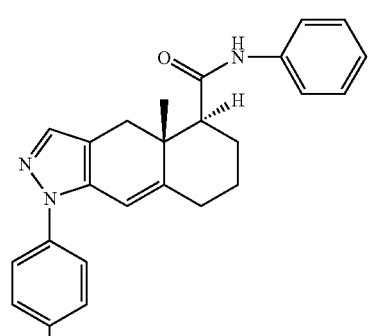 | 402 |

Example 159

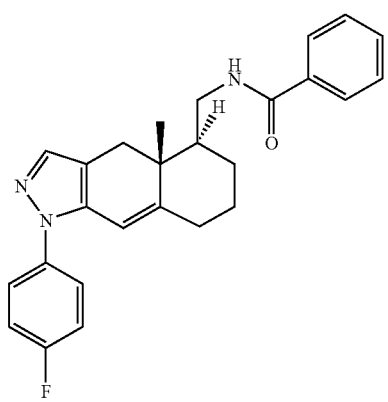

Step 1.

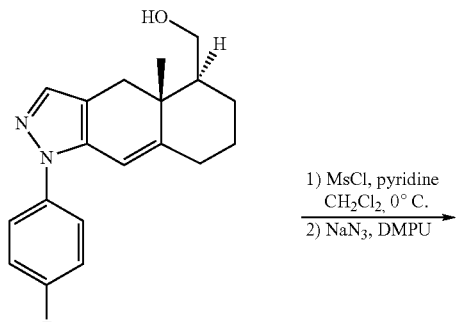

Example 87

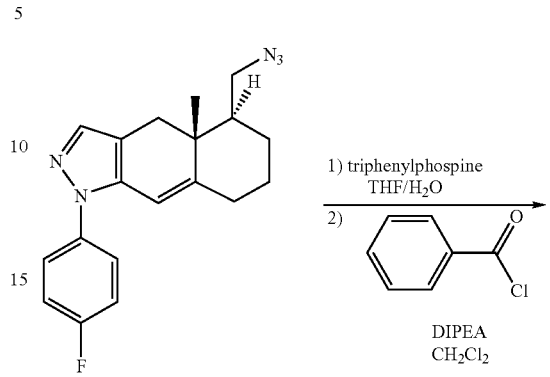

158

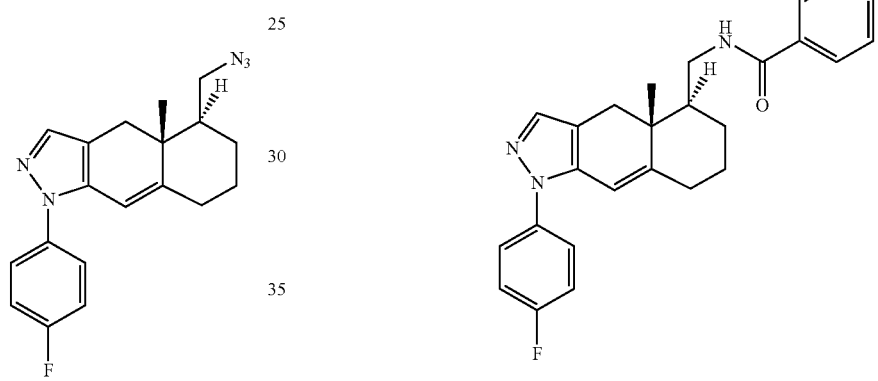

Example 159

Step 2.

Example 158

To a 0° C. solution of 87 (35.4 mg, 0.113 mmol) in CH$_2$Cl$_2$ was added pyridine (270 μL, 2.72 mmol) and MsCl (105 μL, 1.36 mmol). The reaction was stirred at 0° C. for 1 hour and then diluted with EtOAc (50 mL). The organic solution was washed with saturated NaHCO$_3$, H$_2$O, 1 N HCl, and brine (10 mL each). The organic layer was dried over Na$_2$SO$_4$, filtered, and concentrated in vacuo. The crude residue was dissolved in DMPU (4 mL) and NaN$_3$ (37 mg, 0.565 mmol) was added. The reaction was stirred at room temperature for 3 days and then heated to 50° C. for 6 hours. The reaction was cooled to room temperature, diluted with EtOAc (50 μL), and washed with H$_2$O and brine (10 mL each). The organic layer was dried over Na$_2$SO$_4$, filtered, and concentrated in vacuo. Purification by flash chromatography (20% EtOAc/hexanes) afforded 32.2 mg (84%) of 158. R$_f$=0.38 (25% EtOAc/hexanes). LCMS=338; (M+1)$^+$. $^1$H NMR (CDCl$_3$, 500 MHz) δ 7.43-7.46 (m, 2H), 7.41 (s, 1H), 7.13-7.17 (m, 2H), 6.14 (d, J=1.9 Hz, 1H), 3.61 (dd, J=12.1, 3.7 Hz, 1H), 3.11 (dd, J=12.0, 9.7 Hz, 1H), 2.91 (d, J=15.4 Hz, 1H), 2.63 (d, J=15.4 Hz, 1H), 2.29-2.40 (m, 2H), 1.97 (m, 1H), 1.87 (m, 1H), 1.71 (m, 1H), 1.31-1.43 (m, 2H), 0.96 (s, 3H).

To a solution of 158 (3.8 mg, 0.0113 mmol) in THF (300 μL) was added triphenylphosphine (10 mg, 0.0381 mmol) and water (20 μL). The reaction was stirred at room temperature overnight, and then DIPEA was added (50 μL). The reaction was diluted with CH$_2$Cl$_2$ (30 mL), dried over Na$_2$SO$_4$, filtered, and concentrated in vacuo. The residue was dissolved in CH$_2$Cl$_2$ (1 mL) and DIPEA (100 μL, 0.574 mmol) and benzoyl chloride (20 μL, 0.172 mmol) were added. The reaction was stirred at room temperature for 10 minutes, diluted with EtOAc (25 mL) and washed with saturated NaHCO$_3$, brine, 1 N HCl, and brine (5 mL each). The organic layer was dried over Na$_2$SO$_4$, filtered, and concentrated in vacuo. Purification by flash chromatography (60% EtOAc/hexanes) afforded 4.1 mg (88%) of 159. R$_f$=0.35 (60% EtOAc/hexanes). LCMS=416; (M+1)$^+$. $^1$H NMR (CDCl$_3$, 500 MHz) δ 7.78 (d, J=7.4 Hz, 2H), 7.43-7.52 (m, 6H), 7.15 (t, J=8.5 Hz, 2H), 6.20 (s, 1H), 6.13 (d, J=1.6 Hz, 1H), 3.75 (m, 1H), 3.32 (m, 1H), 3.07 (d, J=15.3 Hz, 1H), 2.78 (d, J=15.3 Hz, 1H) 2.40 (m, 1H), 2.32 (m, 1H), 1.88 (m, 2H), 1.76 (m, 1H), 1.32-1.50 (m, 2H), 1.05 (s, 3H).

The following compounds were synthesized following procedures analogous to that described for Example 159:

| Compound | Molecular structure | LCMS (M + 1)+ |
|---|---|---|
| 160 | 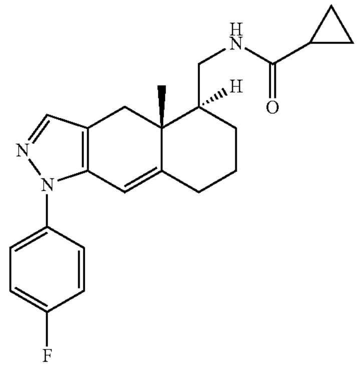 | 380 |
| 161 | 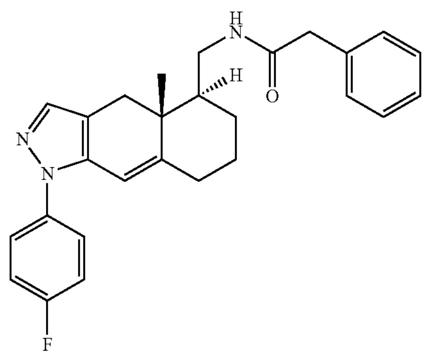 | 430 |
| 162 | 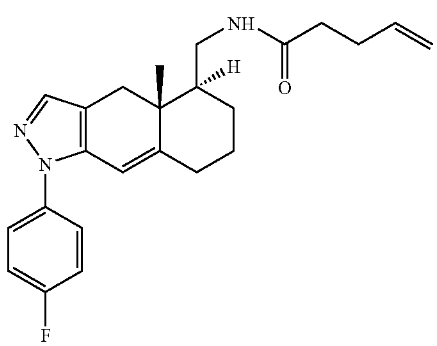 | 394 |
| 163 | 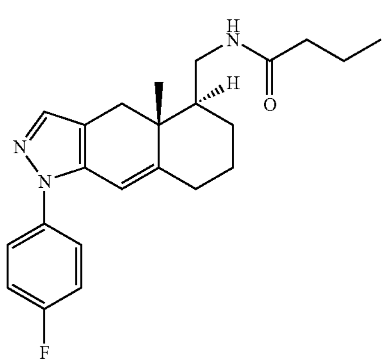 | 382 |

Example 164

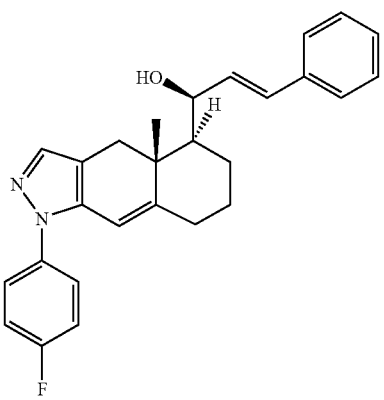

Step 1.

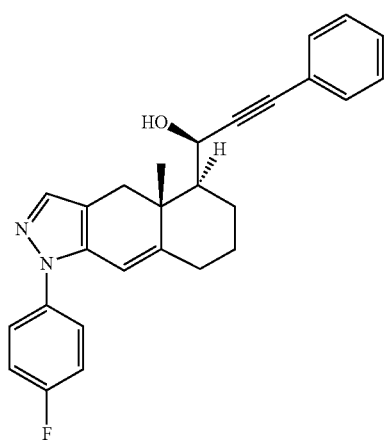

Example 145

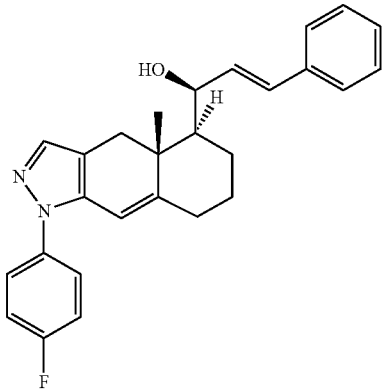

Example 164

To a solution of 145 (7.4 mg, 0.018 mmol) in THF (1 mL) was added LAH (144 µL of a 1 M solution in Et$_2$O, 0.144 mmol). The reaction was stirred at room temperature for 24 hours and then added slowly to a mixture of Et$_2$O/1N HCl (10/1, 20 mL). The mixture was washed with H$_2$O and brine (5 mL each), dried over Na$_2$SO$_4$, filtered, and concentrated in vacuo. Purification of the residue by flash chromatography (5 to 20% EtOAc/hexanes) afforded 4.5 mg (61%) of 164. R$_f$=0.17 (25% EtOAc/hexanes). LCMS=415; (M+1)$^+$.
$^1$H NMR (CDCl$_3$, 500 MHz) δ 7.45-7.47 (m, 2H), 7.43 (s, 1H), 7.40 (d, J=7.4 Hz, 2H), 7.33 (t, J=7.7 Hz, 2H), 7.25 (t, J=7.3 Hz, 1H), 7.15 (t, J=8.5 Hz, 2H), 6.62 (d, J=15.9 Hz, 1H), 6.31 (dd, J=16.0, 5.4 Hz, 1H), 6.12 (d, J=1.8 Hz, 1H), 4.73 (d, J=5.0 Hz, 1H), 3.09 (d, J=15.1 Hz, 1H), 2.62 (d, J=15.1 Hz, 1H), 2.42 (m, 1H), 2.32 (m, 1H), 1.91 (m, 1H), 1.79 (m, 1H), 1.67-1.72 (m, 2H), 1.38 (m, 1H), 1.22 (s, 3H).

Example 165

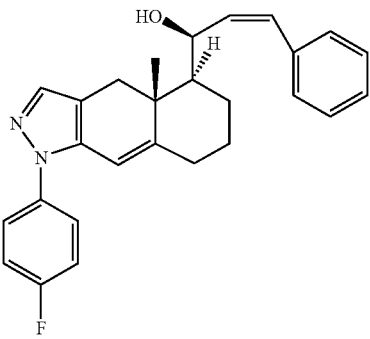

Step 1.

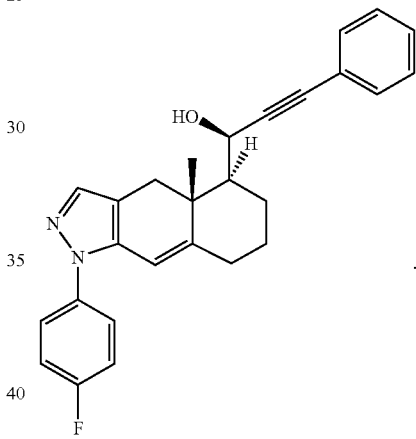

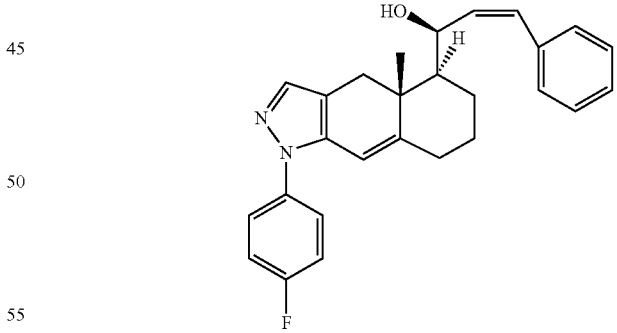

Example 165

To a solution of 145 (12.9 mg, 0.031 mmol) in hexanes/TBF (3/1; 1.6 mL) was added Pd on CaCO$_3$ poisoned with lead (4 mg) and quinoline (15 µL). The mixture was stirred at room temperature for 15 minutes and then placed under H$_2$. The reaction was stirred at room temperature for 2 hours and then the catalyst was removed by filtration. The filtrate was diluted with EtOAc (35 mL), washed with 1 N HCl and brine (10 mL each), dried over Na$_2$SO$_4$, filtered, and concentrated in vacuo. Purification of the residue by flash chromatography (5 to 20% EtOAc/hexanes) afforded 7.3 mg (56%) of 165. $R_f$=0.17 (25% EtOAc/hexanes). LCMS=415; (M+1)$^+$. $^1$H NMR (CDCl$_3$, 500 MHz) δ 7.38-7.44 (m, 4H), 7.32-7.35 (m, 4H), 7.14 (t, J=8.6 Hz, 2H), 6.56 (d, J=11.7 Hz, 1H), 6.08 (d, J=1.8 Hz, 1H), 5.90 (dd, J=11.7, 9.0 Hz, 1H), 4.91 (d, J=8.9 Hz, 1H), 2.76 (d, J=15.2 Hz, 1H), 2.29-2.42 (m, 3H), 1.88-1.96 (m, 2H), 1.77 (qd, J=9.6, 3.3 Hz, 1H), 1.62 (dd, J=12.5, 2.4 Hz, 1H), 1.41 (m, 1H), 1.10 (s, 3H).

Example 166+167

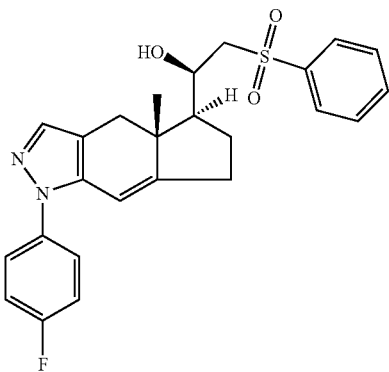

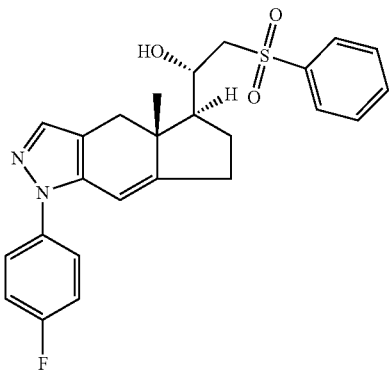

Step 1: Addition of Lithium Phenyl Sulfone Reagent to Aldehyde F

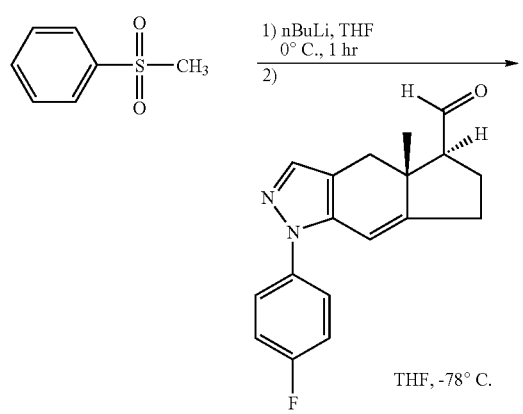

-continued

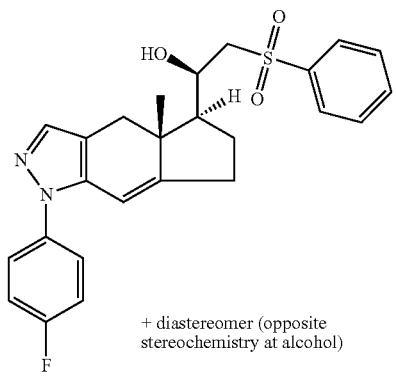

+ diastereomer (opposite stereochemistry at alcohol)

Example 166 + 167

A solution of methyl phenyl sulfone (285 mg, 1.83 mmol) in THF (16 mL) was cooled to 0° C. and nBuLi (950 μL of a 1.6 M solution in hexanes, 1.52 mmol) was added dropwise by syringe. The reaction was stirred at 0° C. for 1 hour and then it was further cooled to −78° C. Aldehyde F (45.1 mg, 0.152 mmol) in THF (4 mL) was added by cannula. The reaction was stirred at −78° C. for 45 minutes. 1 mL of isopropyl alcohol was added at −78° C. and then the reaction was poured into saturated NH$_4$Cl (25 mL). The mixture was extracted with EtOAc (50 mL) and the organic layer was washed with water and brine (15 mL each). The organic layer was dried over Na$_2$SO$_4$, filtered, and concentrated in vacuo. Purification by flash chromatography (10 to 50% EtOAc/hexanes) yielded a mixture of 2 diastereomers. Further purification by PTLC (20/40/40 hexanes/CH$_2$Cl$_2$/Et$_2$O) afforded 24.4 mg (35%) of the less polar diastereomer and 11.3 mg (16%) of the more polar diastereomer.

Less Polar diastereomer: $R_f$=0.32 (50% EtOAc/hexanes). LCMS=453; (M+1)$^+$. $^1$H NMR (CDCl$_3$, 600 MHz): δ 7.98 (d, J=7.8 Hz, 2H), 7.70 (t, J=7.5 Hz, 1H), 7.61 (t, J=7.8 Hz, 2H), 7.42 (m, 2H), 7.36 (s, 1H), 6.08 (s, 1H), 4.32 (m, 1H), 3.48 (s, 1H), 3.32 (m, 2H), 2.67 (d, J=15 Hz, 1H), 2.57 (m, 1H), 2.51 (d, J=15 Hz, 1H), 2.15 (s, 1H), 1.99 (m, 1H), 1.91 (m, 1H), 1.83 (m, 1H), 0.89 (s, 3H).

More Polar diastereomer: $R_f$=0.32 (50% EtOAc/hexanes). LCMS=453; (M+1)$^+$. $^1$H NMR (CDCl$_3$, 600 MHz): δ 7.95 (d, J=8.4 Hz, 2H), 7.68 (m, 1H), 7.61 (t, J=9 Hz, 2H), 7.45 (m, 2H), 7.38 (s, 1H), 7.13 (t, J=9 Hz, 2H), 6.11 (s, 1H), 4.26 (m, 1H), 3.27 (s, 2H), 3.15 (d, J=19.2 Hz, 2H), 2.63 (d, J=19.2 Hz, 1H), 2.57 (m, 1H), 2.42 (m, 1H), 2.15 (s, 1H), 1.98 (m, 1H), 1.71 (m, 2H), 1.42 (m, 1H), 1.03 (s, 3H).

Starting from the appropriate aldehyde, the following compounds were synthesized following procedures analogous to those described for examples 166 and 167:

| Compound | Molecular structure | LCMS (M + 1)+ |
|---|---|---|
| 168 | 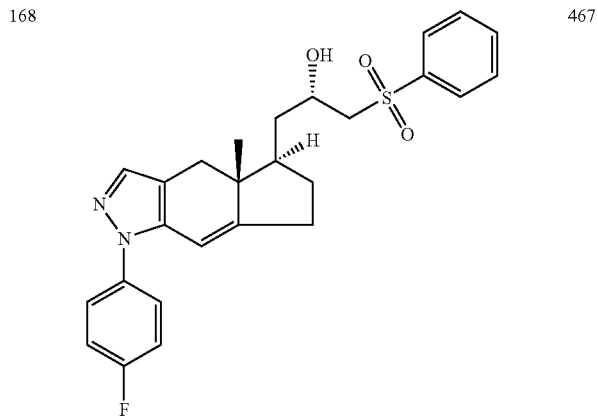 | 467 |
| 169 | 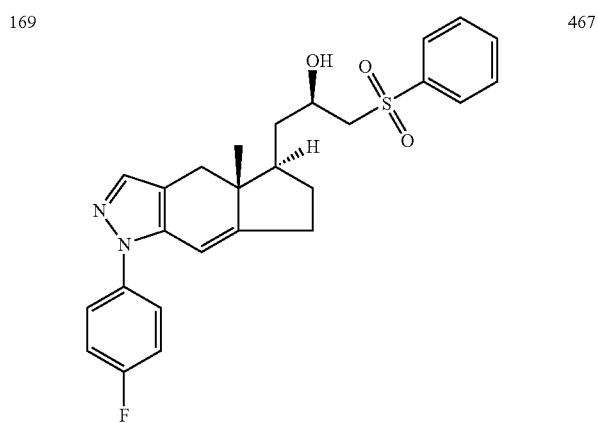 | 467 |
Epoxide Q/R
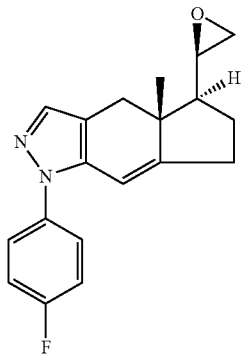
-continued
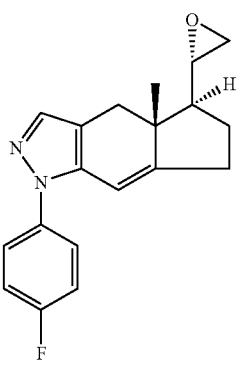

Step 1:

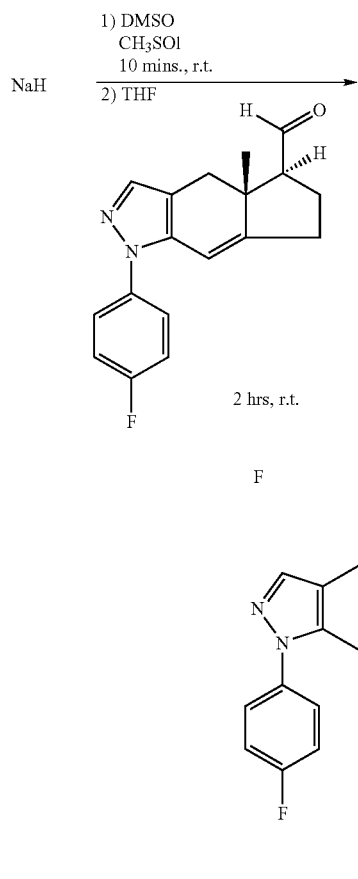

Q/R

Trimethyl sulfoxonium iodide (240 mg, 1.09 mmol) was added as a solid to a suspension of sodium hydride (36.5 mg, 0.91 mmol of a 60% dispersion in mineral oil) in DMSO (2 mL). The reaction was stirred at room temperature for 10 minutes. Aldehyde F (54.0 mg, 0.18 mmol) in THF (4 mL) was added by cannula. The reaction was stirred at room temperature for 2 hours. 1 mL of water was added and then the reaction was poured into saturated NaHCO$_3$ (25 mL). The mixture was extracted with EtOAc (50 mL) and the organic layer was washed with water and brine (15 mL each). The organic layer was dried over Na$_2$SO$_4$, filtered, and concentrated in vacuo. Purification by flash chromatography (5 to 40% EtOAc/hexanes) yielded 8.8 mg (16%) of the less polar diastereomer and 11.2 mg (20%) of the more polar diastereomer.

Less Polar diastereomer: R$_f$=0.56 (50% EtOAc/hexanes). LCMS=311; (M+1)$^+$. $^1$H NMR (CDCl$_3$, 600 MHz): δ 7.15 (m, 2H), 6.91 (s, 1H), 6.80 (t, J=8.7 Hz, 2H), 5.85 (s, 1H), 2.56 (m, 1H), 2.44 (d, J=15.6 Hz, 1H), 2.32 (m, 1H), 2.24 (m, 1H), 2.18 (d, J=15.6 Hz, 1H), 2.12 (m, 1H), 2.02 (m, 1H), 1.45 (m, 2H), 1.31 (m, 1H), 0.63 (s, 3H).

More Polar diastereomer: R$_f$=0.52 (50% EtOAc/hexanes). LCMS=311; (M+1)$^+$. $^1$H NMR (CDCl$_3$, 600 MHz): δ 7.12 (m, 2H), 6.94 (s, 1H), 6.84 (t, J=8.7 Hz, 2H), 5.82 (s, 1H), 2.50 (m, 1H), 2.47 (s, 1H), 2.79 (m, 1H), 2.17 (m, 2H), 2.07 (m, 2H), 1.44 (m, 2H), 1.19 (m, 1H), 0.67 (s, 3H).

Starting from the appropriate aldehyde, the following compounds were synthesized following procedures analogous to those described for Q/R:

| Compound | Molecular structure | LCMS (M + 1)$^+$ |
|---|---|---|
| S | 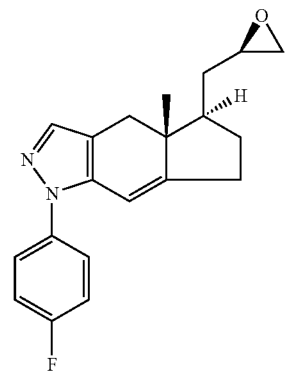 | 326 |
| T | 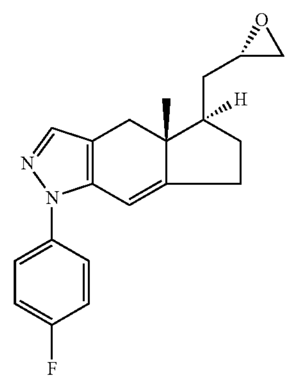 | 326 |

Example 170 and 171

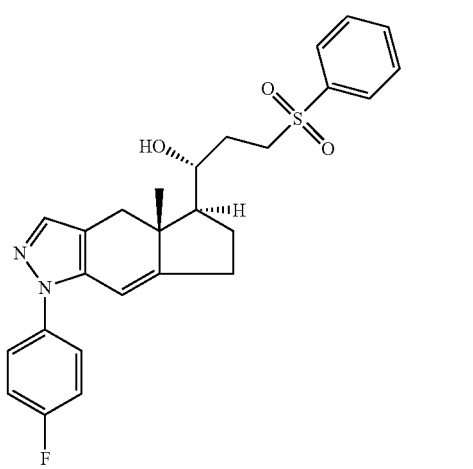

-continued

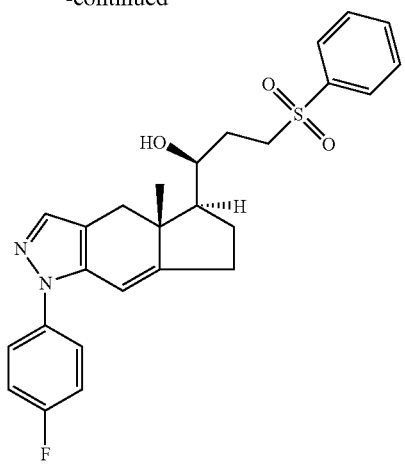

Step 1: Addition of Lithium Phenyl Sulfone Reagent to Epoxide R

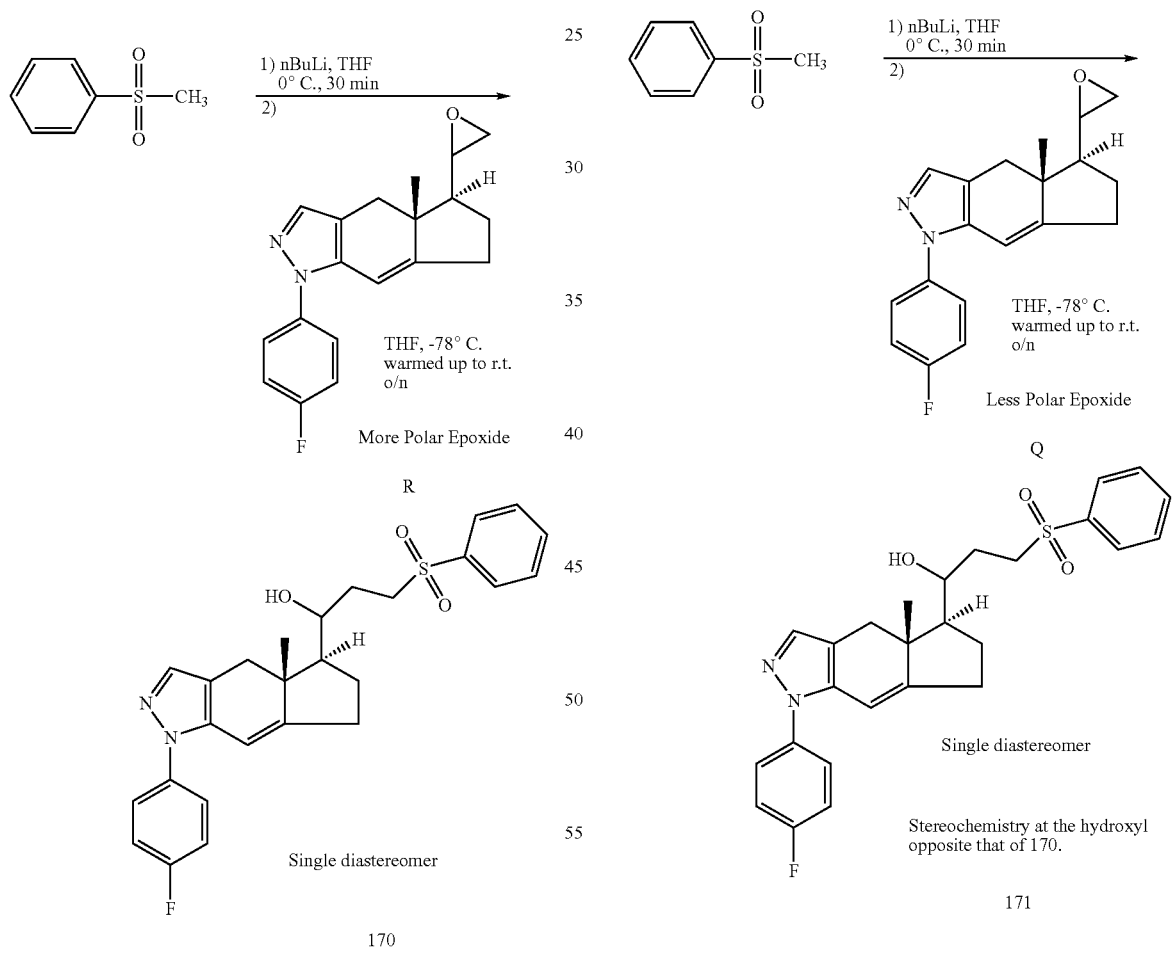

A solution of methyl phenyl sulfone (305 mg, 1.92 mmol) in TBF (12 mL) was cooled to 0° C. and nBuLi (1 mL of a 1.6 M solution in hexanes, 1.6 mmol) was added dropwise by syringe. The reaction was stirred at 0° C. for 30 min. and then cooled to −78° C. Epoxide R (10 mg, 0.032 mmol) in TBF (2 mL) was added by cannula. The reaction was stirred at −78° C. for 45 minutes. The reaction was warmed to room temperature and left at room temperature overnight. After stirring overnight at room temperature, 1 mL of isopropyl alcohol was added, and the reaction was poured into saturated NH$_4$Cl (10 mL). The mixture was extracted with EtOAc (25 mL) and the organic layer was washed with water and brine (10 mL each). The organic layer was dried over Na$_2$SO$_4$, filtered, and concentrated in vacuo. Purification by flash chromatography (5 to 100% EtOAc/hexanes) yielded a mixture of desired product and minor impurities. Further purification by PTLC (20/40/40 hexanes/CH$_2$Cl$_2$/Et$_2$O) afforded 4.9 mg (33%) of 170. R$_f$=0.17 (50% EtOAc/hexanes). LCMS=467; (M+1)$^+$. $^1$H NMR (CDCl$_3$, 600 MHz): δ 7.94 (d, J=7.8 Hz, 2H), 7.68 (t, J=7.5 Hz, 1H), 7.59 (t, J=7.8 Hz, 2H), 7.45 (m, 2H), 7.37 (s, 1H), 7.13 (t, J=8.1 Hz, 2H), 6.13 (s, 1H), 3.82 (t, J=7.8 Hz, 1H), 3.29 (m, 2H), 3.05 (d, J=15.6 Hz, 1H), 2.61 (m, 1H), 2.45 (m, 1H), 2.12 (m, 1H), 1.83 (m, 4H), 1.64 (m, 1H), 1.53 (m, 1H), 1.01 (s, 3H).

A solution of methyl phenyl sulfone (305 mg, 1.92 mmol) in TBF (12 mL) was cooled to 0° C. and nBuLi (1 mL of a 1.6 M solution in hexanes, 1.6 mmol) was added dropwise by syringe. The reaction was stirred at 0° C. for 30 min and then cooled to −78° C. Epoxide Q (10 mg, 0.032 mmol) in THF (2 mL) was added by cannula. The reaction was stirred at −78° C. for 45 minutes. The reaction was warmed to room temperature and left at room temperature overnight. After stirring overnight at room temperature, 1 mL of isopropyl alcohol was added and the reaction was poured into saturated NH$_4$Cl (10 mL). The mixture was extracted with EtOAc (25 mL) and the organic layer was washed with water and brine (10 mL each). The organic layer was dried over Na$_2$SO$_4$, filtered, and concentrated in vacuo. Purification by flash chromatography (5 to 100% EtOAc/hexanes) yielded a mixture of desired product and some minor impurities. Further purification by PTLC (20/40/40 hexanes/CH$_2$Cl$_2$/Et$_2$O) afforded 3.2 mg of example 171 (21%). R$_f$=0.17 (50% EtOAc/hexanes). LCMS=467; (M+1)$^+$. $^1$H NMR (CDCl$_3$, 600 MHz): δ 7.96 (d, J=7.8 Hz, 2H), 7.69 (m, 1H), 7.61 (m, 2H), 7.45 (m, 2H), 7.38 (s, 1H), 7.14 (t, J=7.8 Hz, 2H), 6.12 (s, 1H), 3.87 (m, 1H), 3.34 (m, 2H), 2.75 (d, J=15.5 Hz, 1H), 2.60 (m, 1H), 2.53 (d, J=15.5 Hz, 1H), 2.43 (m, 1H), 2.14 (m, 1H), 1.89 (m, 1H), 1.81 (m, 3H), 0.96 (s, 3H).

Starting from the appropriate epoxide, the following compounds were synthesized following procedures analogous to those described for examples 170 and 171:

Example 174

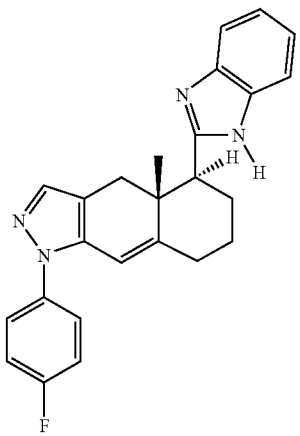

174

| Compound | Molecular structure | LCMS (M + 1)$^+$ |
|---|---|---|
| 172 | 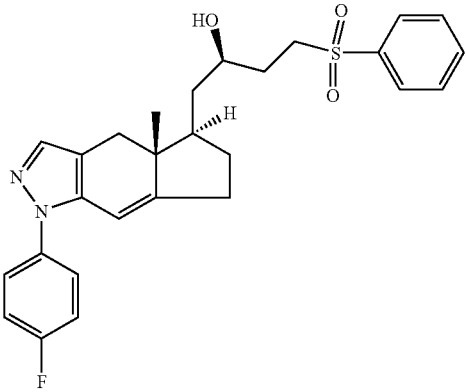 | 481 |
| 173 | 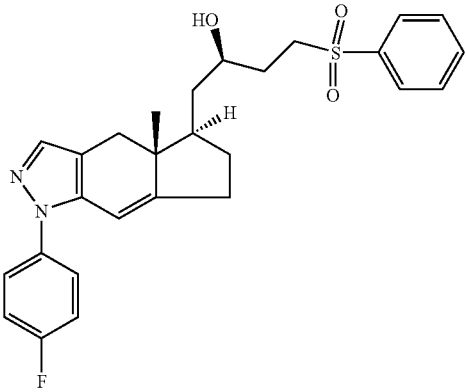 | 481 |

Step 1: Addition of 1,2 Phenylenediamine to Aldehyde B.

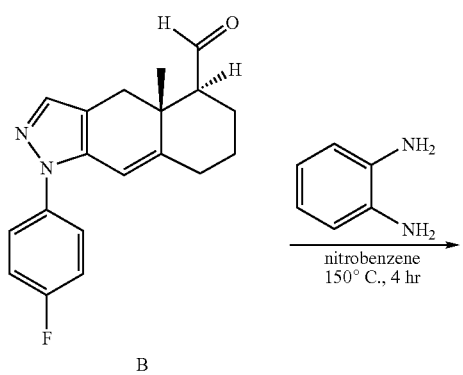

6.14 (s, 1H), 3.19 (m, 1H), 2.88 (d, J=15.5 Hz, 1H), 2.63 (d, J=15.5 Hz, 1H), 2.40 (m, 2H), 2.21 (m, 2H), 1.94 (m, 2H), 1.44 (m, 1H), 1.21 (s, 3H).

Starting from the appropriate aldehyde, the following compounds were synthesized following procedures analogous to those described for Benzimidazole 174:

| Compound | Molecular structure | LCMS $(M + 1)^+$ |
|---|---|---|
| 175 | 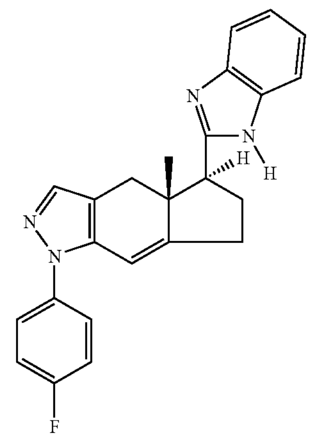 | 385 |
| 176 | 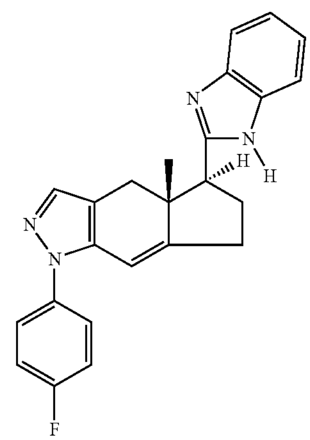 | 399 |

Example 177 and 178

1,2 Phenylenediamine (10.5 mg, 0.097 mmol) and aldehyde B (15.0 mg, 0.05 mmol) were placed in a flask under nitrogen. Nitrobenzene (500 μL) was added, and the reaction was heated to 150° C. The reaction was stirred at 150° C. for 4 hours. After cooling to room temperature, the reaction was loaded directyl onto silica gel and the column was eluted with 100% hexanes to remove the nitrobenzene, followed by 40 to 80% EtOAc/hexanes to afford a mixture of the desired product and some minor impurities. Further purification by PTLC (2/98 MeOH(CH$_2$Cl$_2$) gave 16.0 mg (84%) of example 174: $R_f$=0.19 (40% EtOAc/hexanes). LCMS=399; $(M+1)^+$. $^1$H NMR (CDCl$_3$, 500 MHz): δ 7.55 (s, 1H), 7.39 (m, 2H), 7.26 (s, 1H), 7.20 (m, 2H), 7.11 (t, J=8.5 Hz, 3H),

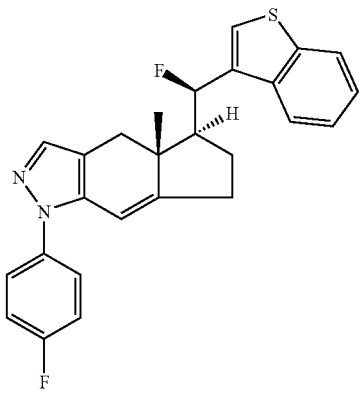

177

-continued

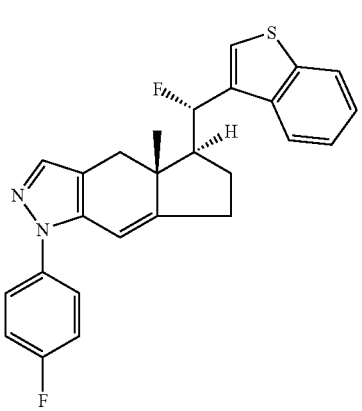

178

Step 1. Addition of DAST to Example 119.

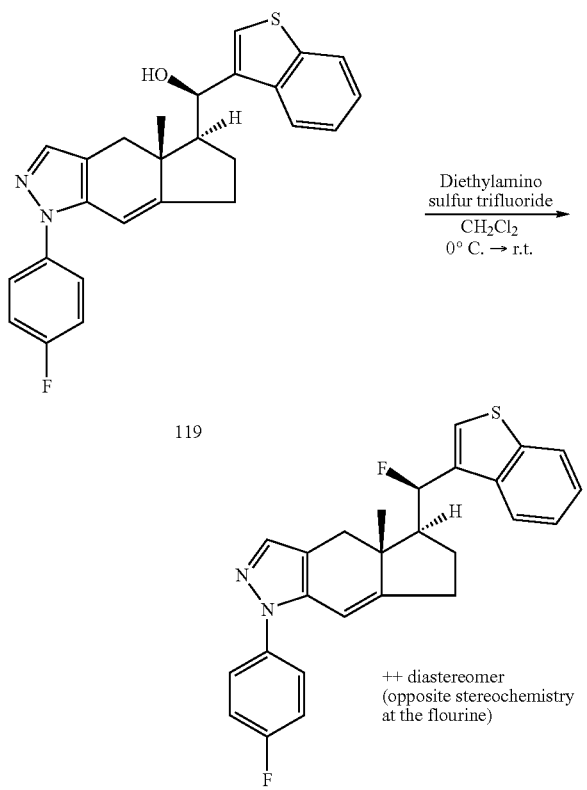

Example 177 and 178

In a plastic vial, a solution of Example 119 (38.2 mg, 0.089 mmol) in CH$_2$Cl$_2$ (500 μL) was cooled to 0° C. and diethylamino sulfur trifluoride (23.6 μL, 0.178 mmol) was added dropwise by syringe. The reaction was stirred at 0° C. for 10 minutes and then was warmed to room temperature. The reaction was stirred at room temperature for 2 hours. The reaction was poured into saturated NaHCO$_3$ (10 mL). The mixture was extracted with EtOAc (50 mL) and the organic layer was washed with brine (15 mL). The organic layer was dried over Na$_2$SO$_4$, filtered, and concentrated in vacuo. Purification by flash chromatography (5 to 20% EtOAc/hexanes) yielded a mixture of 2 diastereomers, which were separated using an OD chiral column (15% IPA/heptanes) to yield 4.6 mg (12%) of peak 1 and 6.9 mg (18%) of peak 2.

Peak 1: $R_f$=0.39 (40% EtOAc/hexanes). LCMS=433; (M+1)$^+$. $^1$H NMR (CDCl$_3$, 500 MHz): δ 8.00 (d, J=7.8 Hz, 1H), 7.89 (d, J=7.8 Hz, 1H), 7.48 (m, 2H), 7.46 (s, 1H), 7.15 (t, J=8.4 Hz, 2H), 6.17 (s, 1H), 5.81 (dd, J=47.4 Hz, 10.8 Hz, 1H), 3.21 (dd, J=15.9 Hz, 3.9 Hz, 1H), 2.88 (d, J=16.2 Hz, 1H), 2.80 (m, 1H), 2.59 (m, 1H), 2.40 (m, 1H), 1.59 (m, 1H), 1.48 (m, 1H), 1.26 (s, 3H).

Peak 2: $R_f$=0.44 (40% EtOAc/hexanes). LCMS=433; (M+1)$^+$. $^1$H NMR (CDCl$_3$, 500 MHz): δ 7.92 (d, J=1.8 Hz, 1H), 7.89 (d, J=2.4 Hz, 1H), 7.49 (d, J=1.8 Hz, 1H), 7.41 (m, 4H), 7.14 (t, J=9 Hz, 2H), 6.14 (t, J=1.8 Hz, 1H), 5.91 (dd, J=46.8 Hz, 6.6 Hz, 1H), 2.69 (m, 2H), 2.47 (m, 1H), 2.88 (dd, J=38.7 Hz, 15 Hz, 2H), 2.17 (m, 1H), 1.21 (d, J=6 Hz, 1H), 1.15 (s, 3H).

Aldehyde W

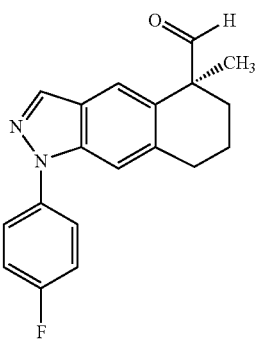

W

Step 1:

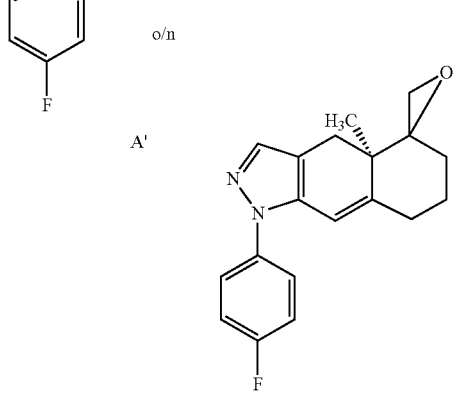

Trimethyl sulfoxonium iodide (334 mg, 1.52 mmol) was added as a solid to a suspension of sodium hydride (54 mg, 1.35 mmol of a 60% dispersion in mineral oil) in DMSO (4 mL). The reaction was stirred at room temperature for 10 minutes. Ketone A (100 mg, 0.338 mmol) in THF (0.5 mL) was added by cannula. The reaction was stirred at room temperature overnight. 1 mL of water was added and then the reaction was poured into saturated NaHCO₃ (25 mL). The mixture was extracted with EtOAc (50 mL) and the organic layer was washed with water and brine (15 mL each). The organic layer was dried over Na₂SO₄, filtered, and concentrated in vacuo. Purification by flash chromatography (5 to 40% EtOAc/hexanes) afforded 101.6 mg (97%) of U. R$_f$=0.56 (40% EtOAc/hexanes). LCMS=311; (M+1)⁺.

Step 2:

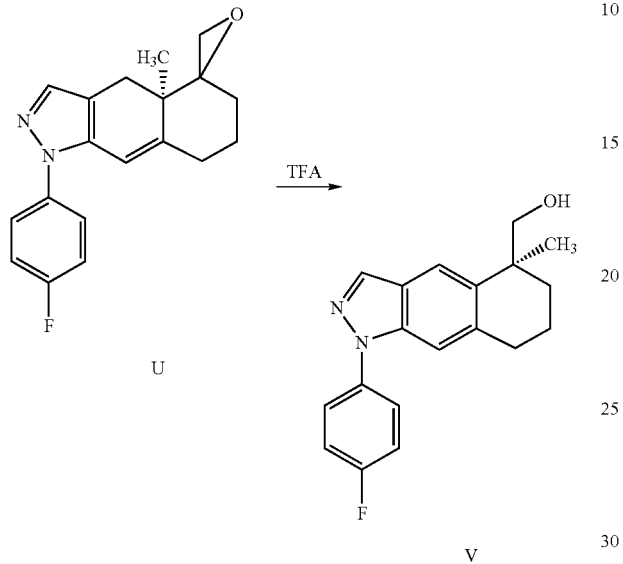

Trifluoroacetic acid (1.5 mL) was added to epoxide U (101.6 mg, 0.322 mmol). This reaction was stirred at room temperature for 20 minutes. The reaction was then poured into ice/H₂O and neutralized with 10% K₂CO₃. The mixture was extracted with EtOAc (20 mL) and the organic layer was washed with water and brine (15 mL each). The organic layer was dried over Na₂SO₄, filtered, and concentrated in vacuo. Purification by flash chromatography (5 to 40% EtOAc/hexanes) afforded 59.1 mg (58%) of V. R$_f$=0.42 (50% EtOAc/hexanes). LCMS=311; (M+1)⁺. ¹H NMR (CDCl₃, 600 MHz): δ 7.29 (s, 1H), 7.64 (s, 1H), 7.51 (m, 2H), 7.16 (s, 1H), 7.12 (t, J=8.4 Hz, 2H), 3.69 (d, J=10.8 Hz, 1H), 3.45 (d, J=10.8 Hz, 1H), 2.82 (m, 2H), 1.96 (m, 1H), 1.75 (m, 2H), 1.52 (m, 1H), 1.24 (m, 3H).

Step 3:

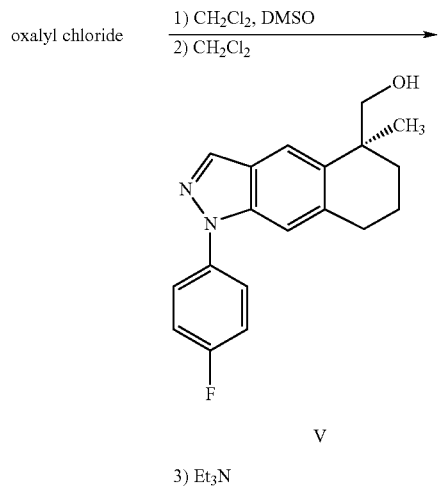

-continued

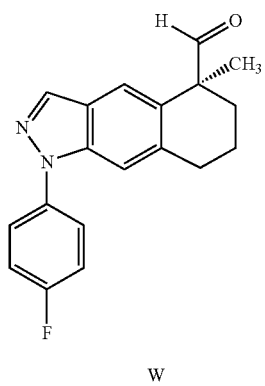

W

A solution of oxalyl chloride (75.4 µL, 0.86 mmol) in CH₂Cl₂ (4 mL) was cooled to −78° C. DMSO (122.7 µL, 1.73 mmols) was added. This reaction was stirred at room temperature for 10 minutes. Alcohol V (53.6 mg, 0.173 mmol) was dissolved CH₂Cl₂ (1 mL) and added to the reaction via cannula. This was stirred at −78° C. for 20 minutes. (482.0 µL, 3.46 mmol) of triethyl amine was added at −78° C. and then the reaction was warmed to room temperature. The mixture was extracted with EtOAc (20 mL) and the organic layer was washed with water, 1N HCl, NaHCO₃, and brine (15 mL each). The organic layer was dried over Na₂SO₄, filtered, and concentrated in vacuo. Purification by flash chromatography (5 to 50% EtOAc/hexanes) afforded 39.8 mg (75%) of W. R$_f$=0.69 (50% EtOAc/hexanes). LCMS=309; (M+1)⁺. ¹H NMR (CDCl₃, 600 MHz): δ 9.55 (s, 1H), 8.11 (s, 1H), 7.66 (m, 2H), 7.53 (s, 1H), 7.44 (s, 1H), 7.23 (t, J=8.4 Hz, 2H), 2.97 (m, 2H), 2.19 (m, 1H), 1.91 (m, 2H), 1.74 (m, 1H), 1.54 (m, 3H).

The following compound was synthesized following procedures analogous to those described for Aldehyde W starting from ketone A:

| Compound | Molecular structure | LCMS (M + 1)⁺ |
|---|---|---|
| X | <img of structure> | 309 |

Example 179 and 180

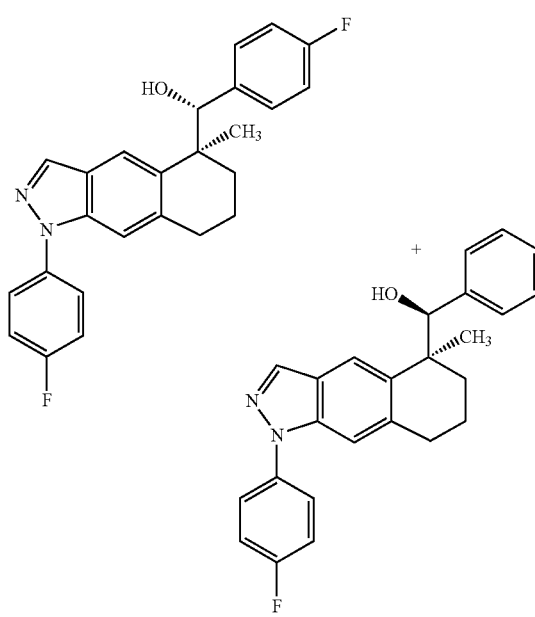

Step 1: Addition of Grignard Reagent to Aldehyde W

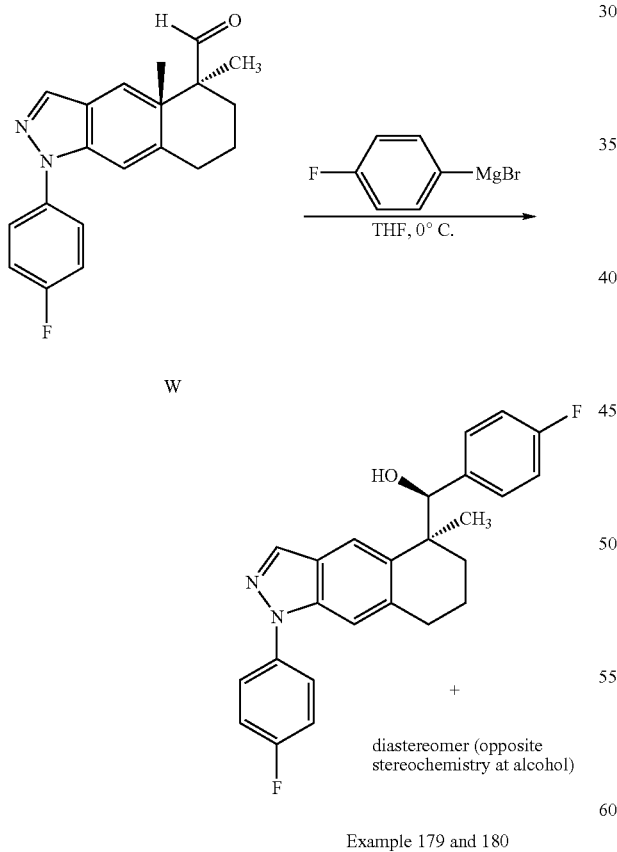

Example 179 and 180

Aldehyde W (38.2 mg, 0.121 mmol) was dissolved in THF (6 mL) and cooled to 0° C. 4-fluorobenzyl magnesium bromide (310 μL of a 2.0 M solution in diethyl ether, 0.620 mmol) was added dropwise by syringe. The reaction was stirred at 0° C. for 1 hour and then quenched with saturated NH$_4$Cl (10 mL). The mixture was extracted with EtOAc (40 mL) and the organic layer was washed with H$_2$O and brine (10 mL each), dried over Na$_2$SO$_4$, filtered, and concentrated in vacuo. Purification by flash chromatography (5 to 80% EtOAc/hexanes) yielded a mixture of 2 diastereomers, which were separated on an AD chiral column (30% IPA/ heptanes) to afford 24.4 mg (49%) of peak 1 and 17.2 mg (34%) of peak 2.

Peak 1: R$_f$=0.11 (25% EtOAc/hexanes). LCMS=405; (M+1)$^+$. $^1$H NMR (CDCl$_3$, 500 MHz): δ 8.03 (s, 1H), 7.83 (s, 1H), 7.56 (m, 2H), 7.15 (t, J=8.5 Hz, 2H), 7.09 (m, 2H), 7.16 (s, 1H), 6.86 (t, J=8.8 Hz, 2H), 4.76 (s, 1H), 2.72 (m, 2H), 2.43 (s, 1H), 1.97 (s, 1H), 1.74 (m, 2H), 1.46 (m, 1H), 1.35 (s, 3H).

Peak 2: R$_f$=0.11 (25% EtOAc/hexanes). LCMS=405; (M+1)$^+$. $^1$H NMR (CDCl$_3$, 500 MHz): δ 7.95 (s, 1H), 7.69 (s, 1H), 7.51 (m, 2H), 7.16 (s, 1H), 7.17 (m, 2H), 7.09 (m, 2H), 6.86 (t, J=8.8 Hz, 2H), 4.95 (s, 1H), 2.78 (m, 2H), 2.03 (m, 1H), 1.97 (s, 1H), 1.72 (s, 1H), 1.52 (m, 2H), 1.11 (s, 3H).

The following compounds were synthesized following procedures analogous to those described for Examples 179 and 180 and starting from Aldehyde X:

| Compound | Molecular structure | LCMS (M + 1)$^+$ |
|---|---|---|
| 181 | 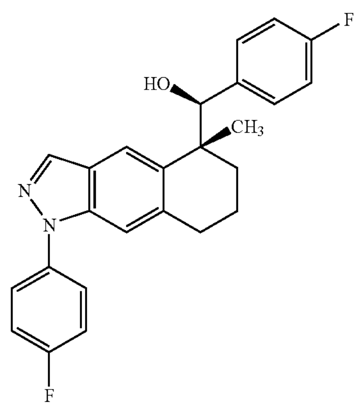 | 405 |
| 182 | 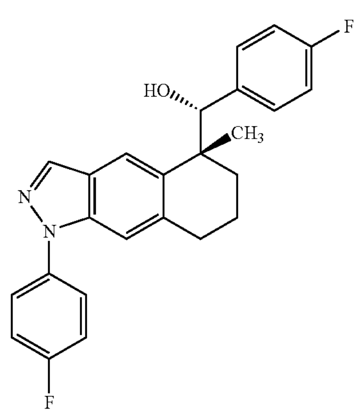 | 405 |

Example 183 and 184

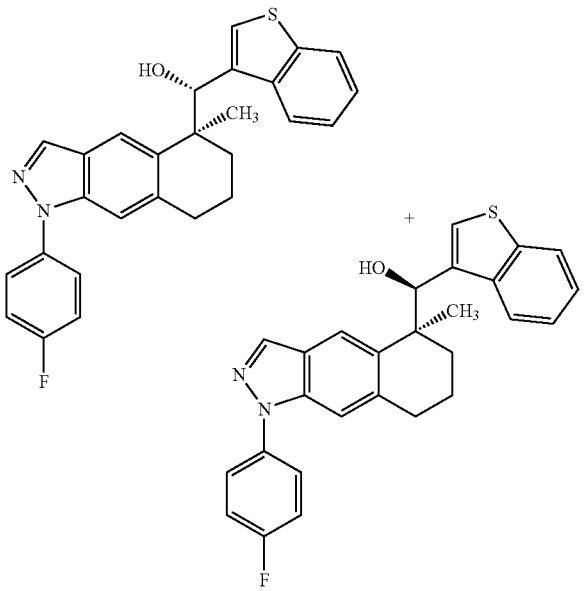

Step 1: Addition of Aryl Lithium to Aldehyde W

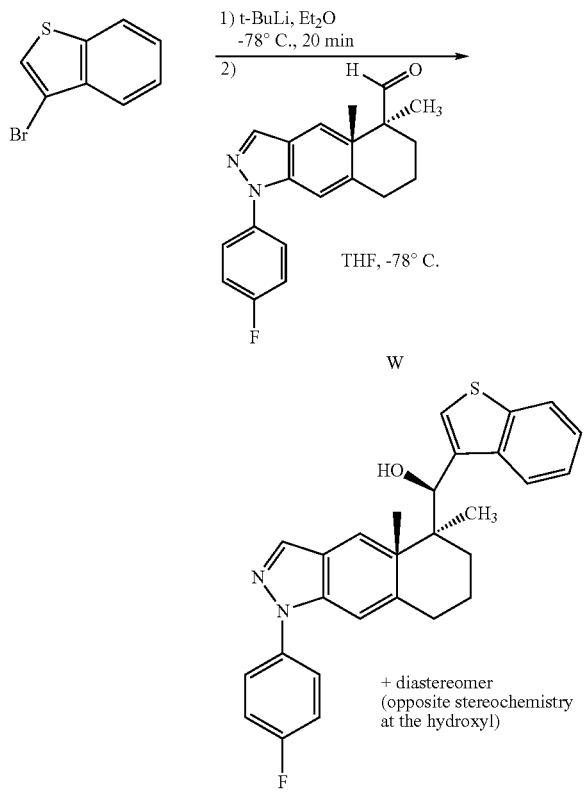

Example 183 and 184

A solution of 3-bromothianapthene (162.2 µL, 1.24 mmol) in Et₂O (16 mL) was cooled to −78° C. and t-BuLi (1.45 mL of a 1.7 M solution in pentanes, 2.48 mmol) was added dropwise by syringe. The reaction was stirred at −78° C. for 20 minutes and then aldehyde W (38.2 mg, 0.124 mmol) in THF (2 mL) was added by cannula. The reaction was stirred at −78° C. for 45 minutes. 1 mL of isopropyl alcohol was added at −78° C. and the reaction was poured into saturated NH₄Cl (10 mL). The mixture was extracted with EtOAc (50 mL) and the organic layer was washed with water and brine (15 mL each). The organic layer was dried over Na₂SO₄, filtered, and concentrated in vacuo. Purification by flash chromatography (5 to 20% EtOAc/hexanes) yielded a mixture of 2 diastereomers that were separated using an AD chiral column (25% IPA/heptanes) to yield 3.8 mg (6.9%) of Peak 1 and 6.7 mg (12%). Peak 2:

Peak 1: $R_f$=0.74 (40% EtOAc/hexanes). LCMS=443; (M+1)⁺. ¹H NMR (CDCl₃, 500 MHz): δ 8.01 (s, 1H), 7.90 (s, 1H), 7.83 (m, 1H), 7.73 (m, 1H), 7.55 (m, 1H), 7.16 (s, 1H), 7.19 (m, 2H), 5.23 (s, 1H), 2.72 (m, 2H), 2.09 (s, 1H), 1.93 (s, 1H), 1.83 (m, 1H), 1.61 (m, 1H), 1.45 (s, 3H).

Peak 2: $R_f$=0.74 (40% EtOAc/hexanes). LCMS=443; (M+1)⁺. ¹H NMR (CDCl₃, 500 MH): δ 7.90 (s, 1H), 7.78 (s, 1H), 7.69 (m, 1H), 7.64 (m, 1H), 7.51 (m, 1H), 7.20 (s, 1H), 7.14 (m, 2H), 7.08 (s, 1H), 7.07 (t, J=9.0 Hz, 2H), 5.47 (s, 1H), 2.73 (t, J=6.3 Hz, 1H), 2.17 (m, 1H), 1.93 (s, 1H), 1.79 (m, 1H), 1.57 (m, 1H), 1.48 (m, 1H), 1.38 (m, 1H), 1.21 (s, 3H).

The following compounds were synthesized following procedures analogous to those described for Examples 183 and 184 and starting from aldehyde X:

| Compound | Molecular structure | LCMS (M + 1)⁺ |
|---|---|---|
| 185 | 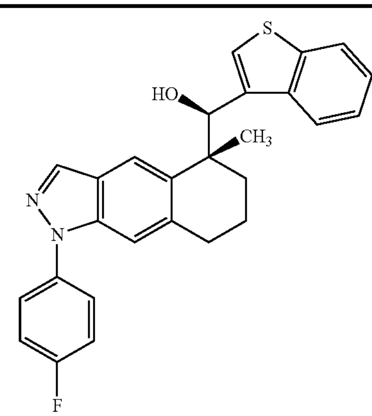 | 443 |
| 186 | 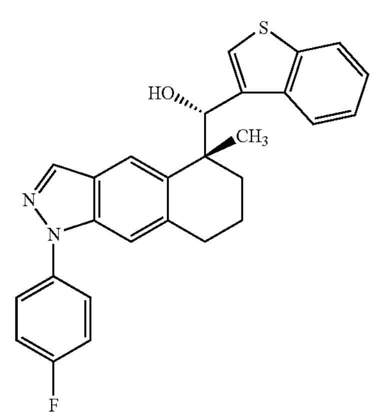 | 443 |

Aldehyde Y

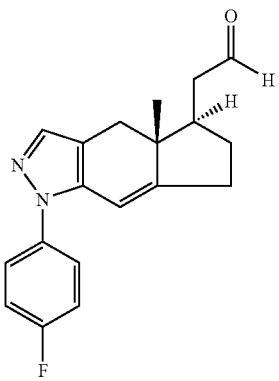

Step 1:

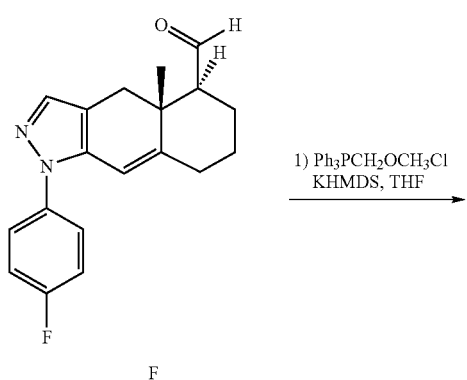

A suspension of (methoxymethyl)triphenylphosphonium chloride (763 mg, 2.2 mmol) in THF (8 mL) was cooled to 0° C. Potassium bis(trimethylsilyl) amide) (3.6 mL of a 0.5 M solution in toluene, 1.78 mmol) was added dropwise by syringe and the reaction turned bright orange/red. Next, a solution of aldehyde F (132 mg, 0.44 mmol) in THF (4 mL) was added by cannula. The reaction was allowed to warm to room temperature. After stirring at room temperature for 2 hours, 4N HCl was added slowly and the reaction was left stirring for another hour. The reaction was then diluted with EtOAc (50 mL), quenched with NaHCO₃ (50 mL), and washed with H₂O and brine (25 mL each). The organic layer was dried over Na₂SO₄, filtered, and concentrated in vacuo. The residue was purified by flash chromatography (5 to 35% EtOAc/hexanes) to afford 95.1 mg (69%) of Y. $R_f$=0.29 (25% EtOAc/hexanes). LCMS=311; (M+1)⁺. ¹H NMR (CDCl₃, 600 MHz) δ 9.86 (t, J=2.1 Hz, 1H), 7.44-7.47 (m, 2H), 7.39 (s, 1H), 7.13-7.16 (m, 1H), 6.17 (s, 1H), 2.68 (d, J=15.0 Hz, 1H), 2.60 (m, 2H), 2.55 (d, J=15.0 Hz, 1H), 2.46 (m, 2H), 2.34 (m, 1H), 2.10 (m, 1H), 1.58 (m, 2H), 0.93 (s, 3H).

Aldehyde Z

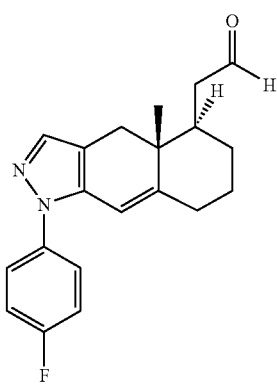

Aldehyde Z was synthesized from aldehyde B using the same procedure as was used in the synthesis of aldehyde Y.

Example 187 and 188

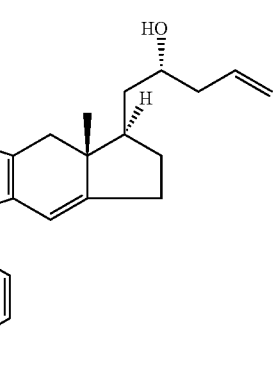

Step 1: Addition of Grignard Reagent to Aldehyde Y

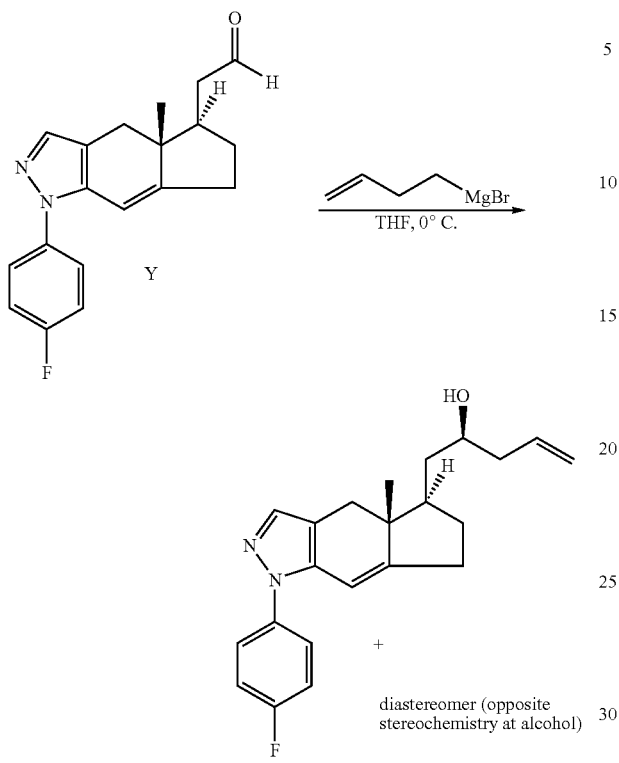

Example 187 and 188

Aldehyde Y (53.0 mg, 0.17 mmol) was dissolved in THF (6 mL) and cooled to 0° C. 3-butenyl magnesium chloride (1.7 mL of a 0.5 M solution in THF, 0.85 mmol) was added dropwise by syringe. The reaction was stirred at 0° C. for 1 hour and then 1 mL of isopropyl alcohol was added. The reaction was then poured into saturated NH$_4$Cl (25 mL) and extracted with EtOAc (40 mL). The organic layer was washed with H$_2$O and brine (25 mL each), dried over Na$_2$SO$_4$, filtered, and concentrated in vacuo. The two diastereomeric products were isolated by flash chromatography (5 to 20% EtOAc/hexanes) to afford 17.3 mg (28%) of the less polar diastereomer and 19.9 mg (32%) of the more polar diastereomer. Less Polar diastereomer: R$_f$=0.15 (25% EtOAc/hexanes). LCMS=366; (M+1)$^+$. $^1$H NMR (CDCl$_3$, 500 MHz): δ 7.44-7.47 (m, 2H), 7.33 (m, 2H), 7.30 (s, 1H), 7.01(m, 1H), 5.73 (m, 1H), 4.95(m, 1H), 4.87 (dd, J=8.5, 1.8 Hz, 1H), 4.86 (d, J=10.3 Hz, 2H), 3.63 (m, 1H), 2.62 (d, J=15.5 Hz, 1H), 2.47 (m, 1H), 2.42 (d, J=7.5 Hz, 1H), 2.07 (m, 2H), 1.92 (m, 1H), 1.74 (m, 1H), 1.38-1.56 (m, 6H), 0.80 (s, 3H).

More Polar diastereomer: R$_f$=0.14 (25% EtOAc/hexanes). LCMS=366; (M+1)$^+$. $^1$H NMR (CDCl$_3$, 500 MHz): δ 7.45 (m, 2H), 7.38 (m, 2H), 7.30 (s, 1H), 7.12 (m, 2H), 6.12 (m, 1H), 5.85 (m, 2H), 5.07(m, 1H), 4.99 (dd, J=8.5, 1.8 Hz, 1H), 3.69 (m, 1H), 2.72 (d, J=15.5 Hz, 1H), 2.57 (m, 1H), 2.51 (d, J=15.5 Hz, 1H), 2.51 (m, 1H), 2.41 (m, 1H), 2.19 (m, 2H), 2.07 (m, 2H), 1.61-1.39 (m, 6H), 0.90 (s, 3H).

The following compounds were synthesized following procedures analogous to those described for examples 187 and 188:

| Compound | Molecular structure | LCMS (M + 1)$^+$ |
|---|---|---|
| 189 | 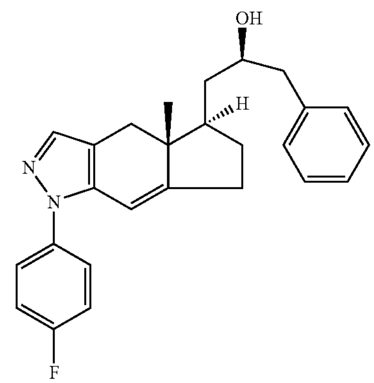 | 403 |
| 190 | 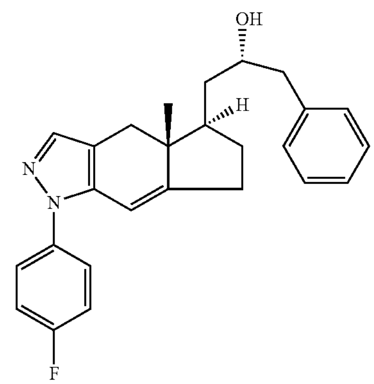 | 403 |
| 191 | 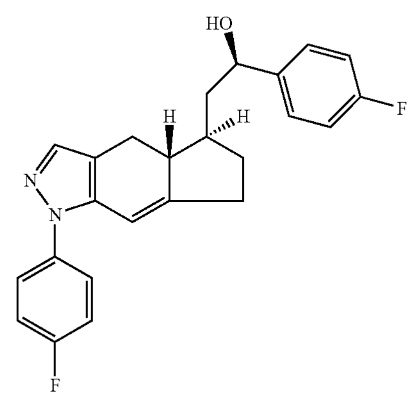 | 407 |
| 192 | 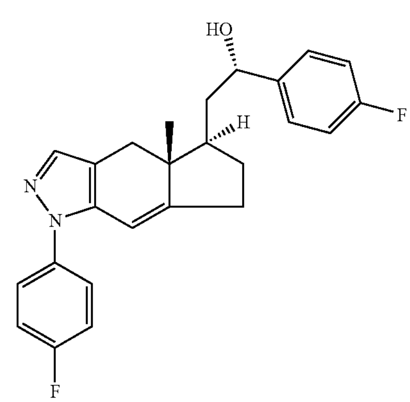 | 407 |

The following compounds were synthesized following procedures analogous to those described for examples 187 and 188 and starting from aldehyde Z:

| Compound | Molecular structure | LCMS (M + 1)+ |
|---|---|---|
| 193 | 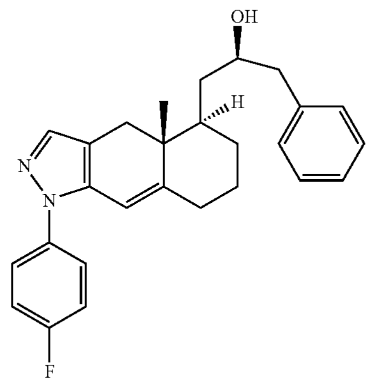 | 417 |
| 194 | 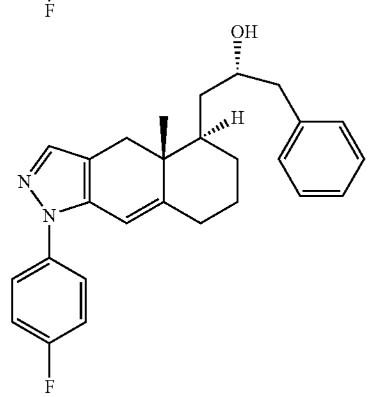 | 417 |
| 195 | 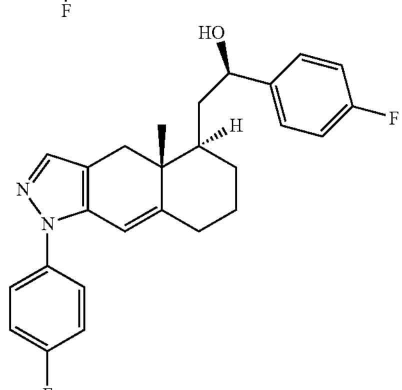 | 421 |
| 196 | 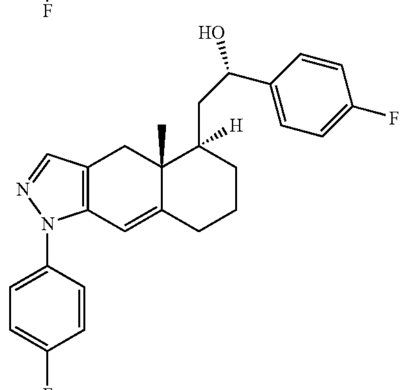 | 421 |

-continued

| Compound | Molecular structure | LCMS (M + 1)+ |
|---|---|---|
| 197 | 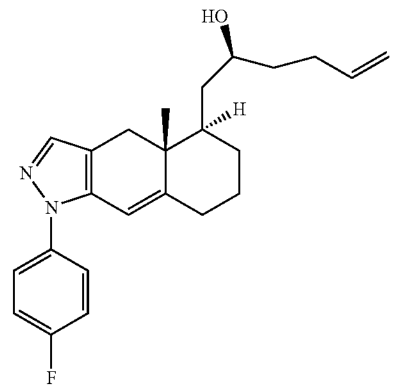 | 381 |
| 198 | 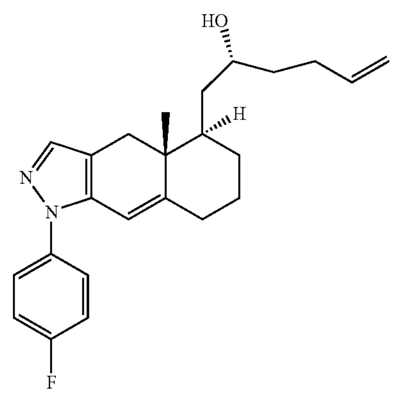 | 381 |

Example 199 and 200

199

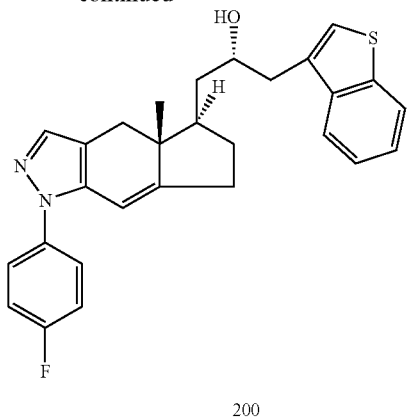

200

Step 1: Addition of Aryl Lithium Reagents to Aldehyde Y

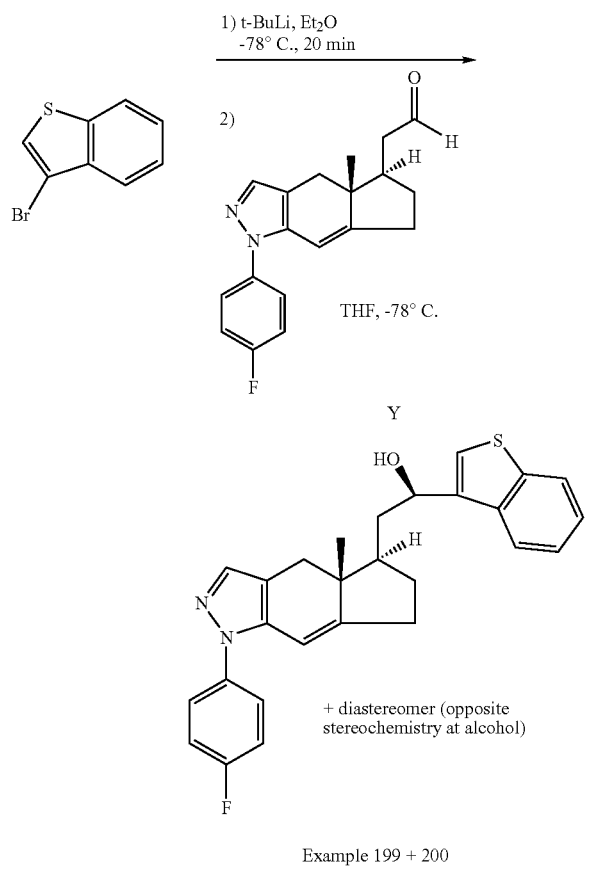

Example 199 + 200

A solution of 1-Bromothianapthene (259 μL, 1.98 mmol) in Et₂O (8 mL) was cooled to −78° C. and t-BuLi (2.3 mL of a 1.7 M solution in pentanes, 3.95 mmol) was added dropwise by syringe. The reaction was stirred at −78° C. for 20 minutes and then aldehyde Y (61.3 mg, 0.20 mmol) in ThF (2 mL) was added by cannula. The reaction was stirred at −78° C. for 45 minutes. 1 mL of isopropyl alcohol was added at −78° C. and then the reaction was poured into saturated NH₄Cl (25 mL). The mixture was extracted with EtOAc (50 mL) and the organic layer was washed with water and brine (15 mL each). The organic layer was dried over Na₂SO₄, filtered, and concentrated in vacuo. Purification by flash chromatography (5 to 20% EtOAc/hexanes) yielded a mixture of 2 diastereomers. Further purification by PTLC (40/40/20 hexanes/CH₂Cl₂/Et₂O) afforded 34.7 mg of the less polar diastereomer contaminated with minor impurities and 28.2 mg (32%) of the more polar diastereomer. Final purification of the less polar diastereomer using an AD Chiral Column (35% isopropyl alcohol/heptanes) afforded 22.3 mg (25%) of the less polar diastereomer.

Less Polar diastereomer: $R_f$=0.21 (25% EtOAc/hexanes). LCMS=445; (M+1)⁺. ¹H NMR (CDCl₃, 500 MHz): δ 7.86 (d, J=8 Hz, 1H), 7.80 (d, J=7.5 Hz, 1H), 7.33 (m, 3H), 7.29 (s, 1H), 7.20 (s, 1H), 7.02 (m, 2H), 6.00 (s, 1H), 5.09 (t, J=6.5 Hz, 1H), 2.64 (d, J=15 Hz, 1H), 2.48 (m, 1H), 2.33 (d, J=15 Hz, 1H), 2.70(m, 1H), 2.13 (m, 1H), 1.97 (m, 1H), 1.87 (m, 1H), 1.73 (m, 1H), 1.52 (m, 1H), 1.18 (m, 1H), 0.86 (s, 3H).

More Polar diastereomer: $R_f$=0.21 (25% EtOAc/hexanes). LCMS=445; (M+1)⁺. ¹H NMR (CDCl₃, 500 MHz): δ 7.88 (t, J=6 Hz, 2H), 7.34-7.45 (m, 6H), 7.13 (t, J=6.25 Hz, 2H), 6.13 (s, 1H), 5.16 (d, J=6.5 Hz, 1H), 2.73 (d, J=12.5 Hz, 1H), 2.59 (m, 1H), 2.54 (d, J=12.5 Hz, 1H), 2.46 (m, 1H), 2.17 (m, 2H), 2.05 (m, 1H), 1.86 (m, 1H), 1.59 (m, 1H), 1.25 (m, 1H), 0.90 (s, 3H).

The following compounds were synthesized following procedures us to that described for Examples 199 and 200:

| Compound | Molecular structure | LCMS (M + 1)⁺ |
|---|---|---|
| 201 | 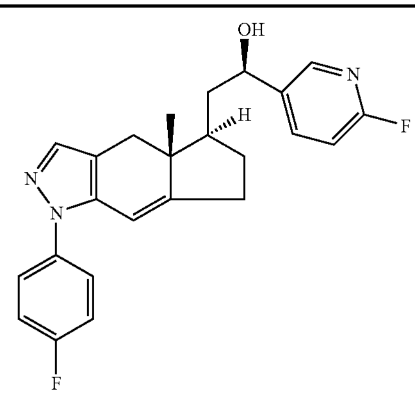 | 408 |
| 202 | 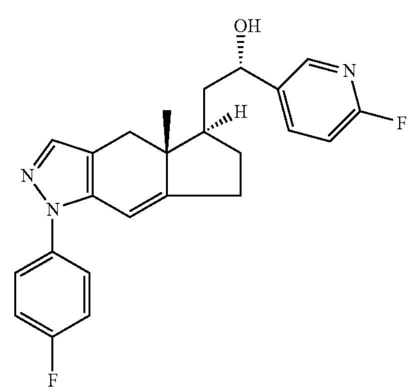 | 408 |

The following compounds were synthesized starring from aldehyde Z and following procedures analogous to that described for Examples 199 and 200:

| Compound | Molecular structure | LCMS (M + 1)+ |
|---|---|---|
| 203 | 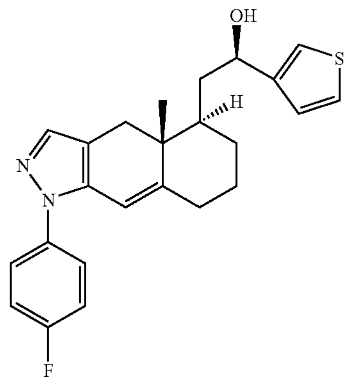 | 409 |
| 204 | 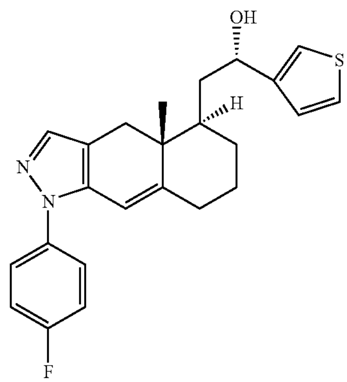 | 409 |
| 205 | 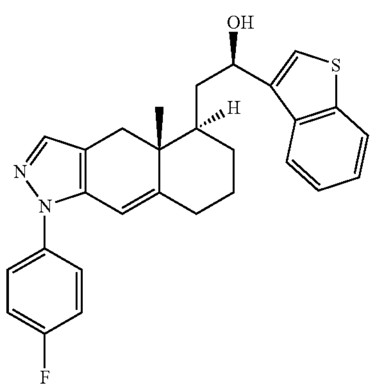 | 459 |
| 206 | 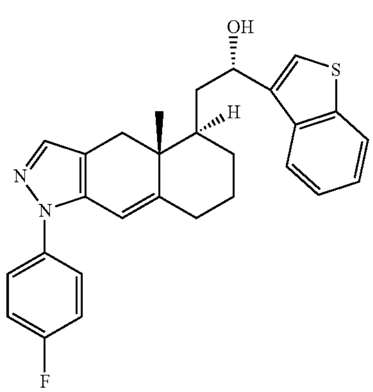 | 459 |

Example 207

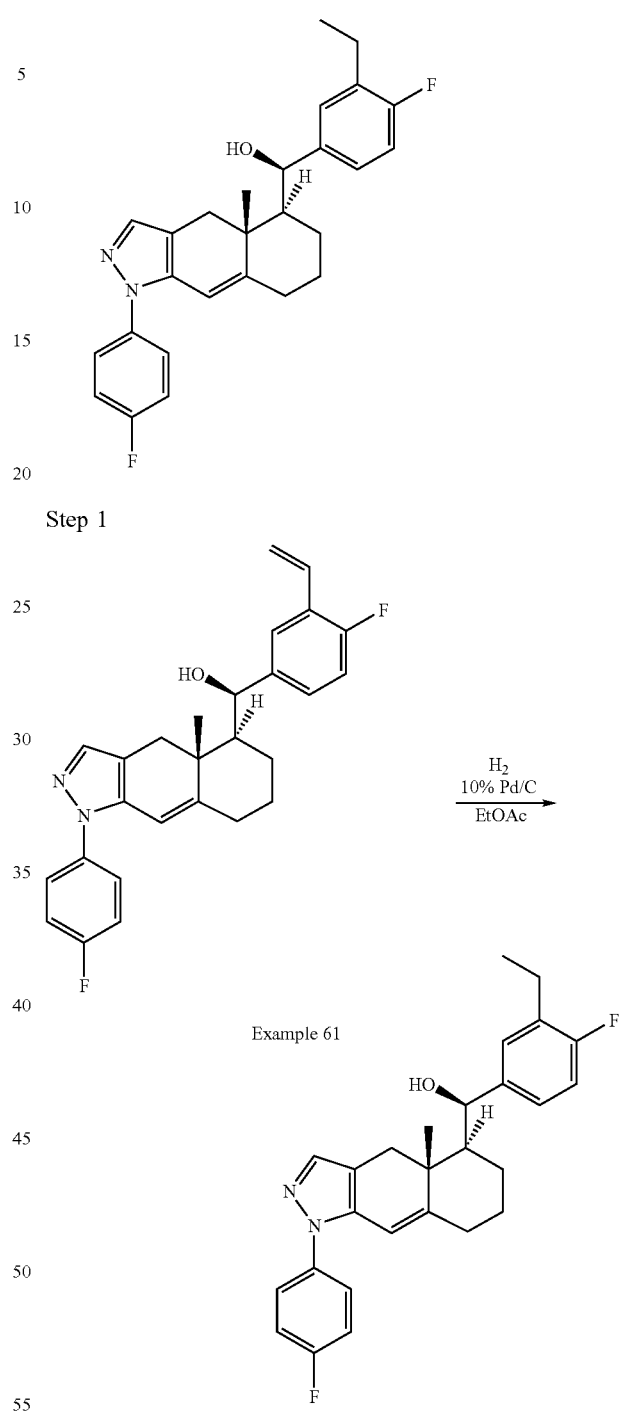

Step 1

Example 61 (4.3 mg, 0.01 mmol) was dissolved in EtOAc (0.5 mL) and 10% Pd on activated carbon (1.0 mg) was added. The reaction was placed under H₂ and stirred at room temperature for 45 minutes. The catalyst was removed by filtration. The filtrate was concentrated, and the residue was purified by preparatory thin layer chromatography (25% EtOAc/hexanes) to afford 2.8 mg (65%) of Example 207. $R_f$=0.15 (25% EtOAc/hexanes). LCMS=435; (M+1)+. ¹H NMR (CDCl₃, 600 MHz) δ 7.45-7.47 (m, 3H), 7.12-7.17 (m, 4H), 6.98 (t, J=8.4 Hz, 1H), 6.12 (s, 1H), 5.16 (s, 1H), 3.18 (d, J=15 Hz, 1H), 2.75 (d, J=15 Hz, 11), 2.65-2.70 (m, 2H), 2.41 (m, 1H), 2.28 (d, J=15 Hz, 1H), 1.59-1.83 (m, 5H), 1.26 (s, 3H), 1.24 (t, J=7.8 Hz, 3H).

Example 208

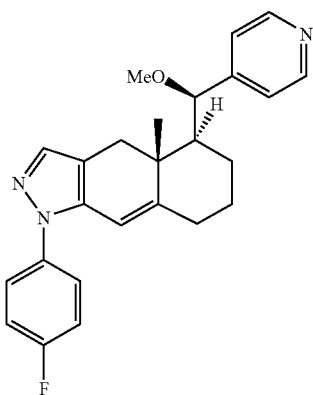

Step 1

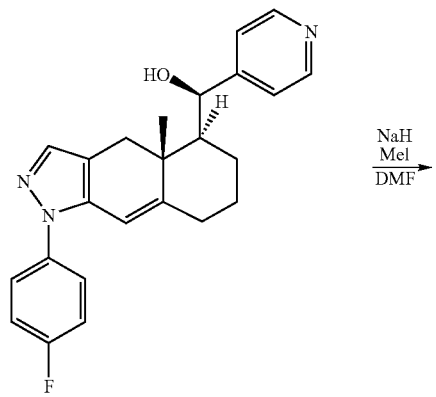

Example 38

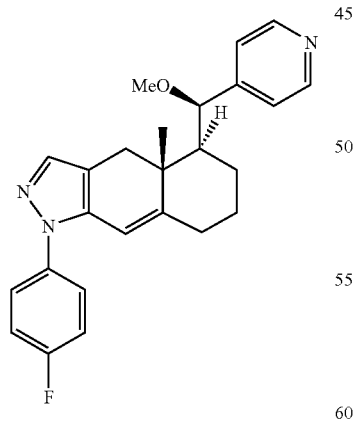

Example 208

Example 38 (11.6 mg, 0.03 mmol) was dissolved in EtOAc (2 mL) and NaH (10 mg, 0.42 mmol) was added. The reaction was stirred at room temperature for 5 minutes and then MeI (3 μL, 0.05 mmol) was added. After 15 minutes, the reaction was poured into water (10 mL) and extracted with EtOAc (25 mL). The organic layer was washed with brine, dried over $Na_2SO_4$, filtered, and concentrated. The residue was purified by preparatory thin layer chromatography (5% $MeOH/CH_2Cl_2$) to afford 10.0 mg (83%) of Example 208. $R_f$=0.18 (5% $MeOH/CH_2Cl_2$). LCMS=404; $(M+1)^+$. $^1H$ NMR ($CDCl_3$, 500 MHz) δ 8.59 (bs, 21), 7.44-7.47 (m, 3H), 7.21 (d, J=4.0 Hz, 2H), 7.15 (t, J=8.5 Hz, 2H), 6.11 (d, J=1.5 Hz, 1H), 4.48 (s, 1H), 3.28 (s, 3H), 3.17 (d, J=15 Hz, 1H), 2.75 (d, J=15 Hz, 1H), 2.38 (m, 1H), 2.25 (d, J=14.5 Hz, 1H), 1.68-1.79 (m, 2H), 1.48-1.57 (m, 2H), 1.18 (s, 3H), 1.10 (m, 1H).

The following compound was synthesized starting from Example 32 and following a procedure analogous to that described for Examples 208:

| Compound | Molecular structure | LCMS $(M + 1)^+$ |
|---|---|---|
| 209 | 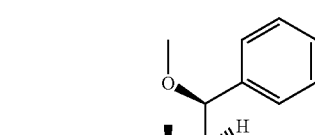 | 421 |

Example 210

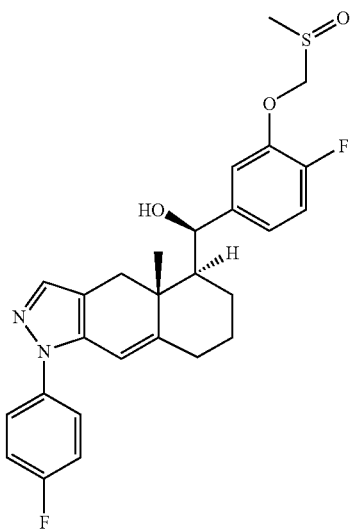

Step 1

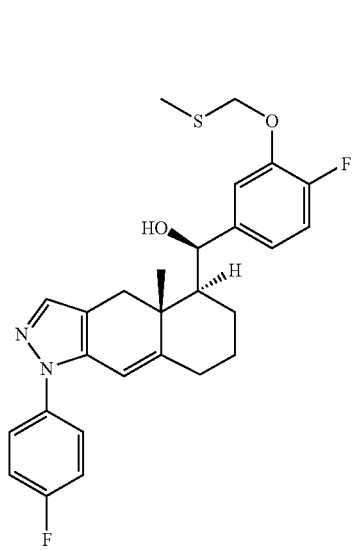

Example 81 m-CPBA
CH$_2$Cl$_2$
−40° C.

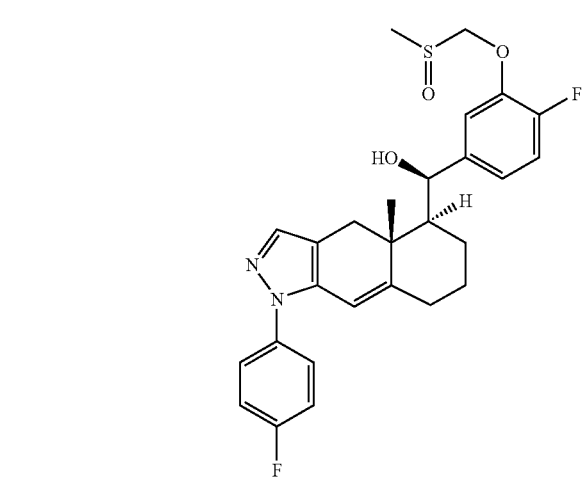

Example 210

Example 211

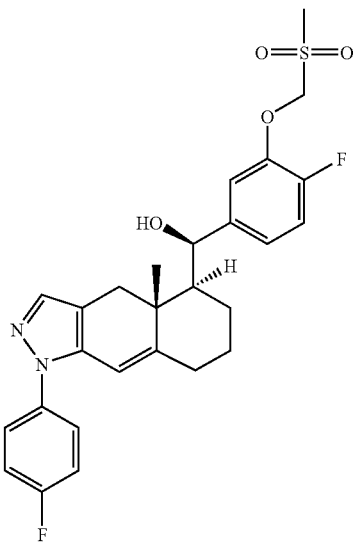

Example 81 oxone
THF/MeOH/water
0° C. to r.t.

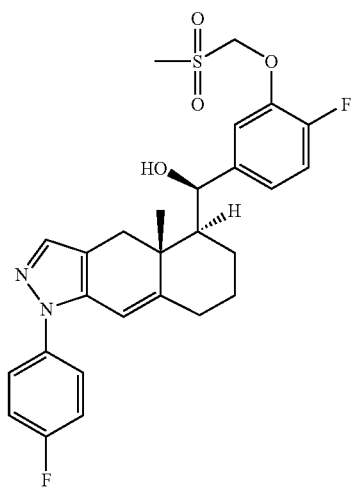

Example 211

Example 81 (9.0 mg, 0.019 mmol) was dissolved in CH$_2$Cl$_2$ (1 mL) and the solution was cooled to −40° C. m-CPBA (6.4 mg, 0.037 mmol) was added and the reaction was stirred at 40° C. for 20 minutes. The reaction was then diluted with EtOAc (25 mL), washed with saturated aq. NaHSO$_3$, saturated NaHCO$_3$, and brine (10 mL each). The organic layer was dried over Na$_2$SO$_4$, filtered, and concentrated. The residue was purified by flash chromatography (100% EtOAc to 5% MeOH/EtOAc) to afford 7.2 mg (78%) of Example 210. R$_f$=0.19 (EtOAc). LCMS=499; (M+1)$^+$. $^1$H NMR (CDCl$_3$, 600 MHz) δ 7.43-7.46 (m, 3H), 7.26 (m, 1H), 7.14-7.16 (m, 2H), 7.08 (dd, J=8.4, 10.0 Hz, 1H), 6.97 (m, 1H), 6.11 (d, J=2.4 Hz, 1H), 5.12 (s, 1H), 5.05 (dd, J=10.2, 3.0 Hz, 1H), 4.97 (dd, J=10.2, 8.4 Hz, 1H), 3.16 (d, J=15 Hz, 1H), 2.73 (d, J=15 Hz, 1H), 2.72 (s, 3H), 2.26-2.42 (m, 2H), 1.64-1.83 (m, 3H), 1.51 (m, 1H), 1.24 (s, 3H), 1.18 (m, 1H).

Example 81 (6.0 mg, 0.012 mmol) was dissolved in THF (100 μL) and MeOH (400 μL) was added. The solution was cooled to 0° C. Oxone (14 mg, 0.024 mmol) was dissolved in H$_2$O (400 μL) and this solution was added to the solution of 81. The reaction was warmed to room temperature and stirred for 4 hours. The reaction was then diluted with EtOAc (25 mL) and washed with water, saturated aq. NaHSO$_3$, saturated NaHCO$_3$, and brine (10 mL each). The organic layer was dried over Na$_2$SO$_4$, filtered, and concentrated. The residue was purified by preparatory thin layer chromatography (60% EtOAc/hexanes) to afford 1.6 mg (25%) of Example 211. R$_f$=0.54 (75% EtOAc/hexanes). LCMS=515; (M+1)$^+$. $^1$H NMR (CDCl$_3$, 500 MHz) δ 7.45-7.48 (m, 3H), 7.01-7.26 (m, 4H), 7.02 (m, 1H), 6.12 (d, J=2.0 Hz, 1H), 5.16 (s, 1H), 5.02 (s, 3H), 3.18 (d, J=15.5 Hz, 1H), 3.07 (s, 3H), 2.74 (d, J=15 Hz, 1H), 2.40 (m, 1H), 2.28 (m, 1H), 1.52-1.89 (m, 4H), 1.25 (s, 3H), 1.19 (m, 1H).

Example 212

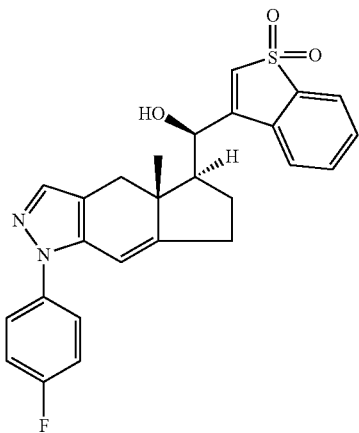

Step 1

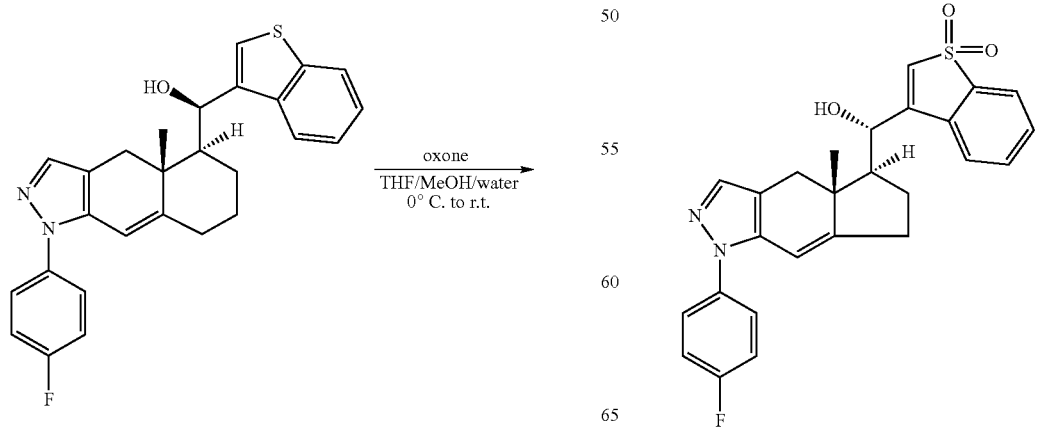

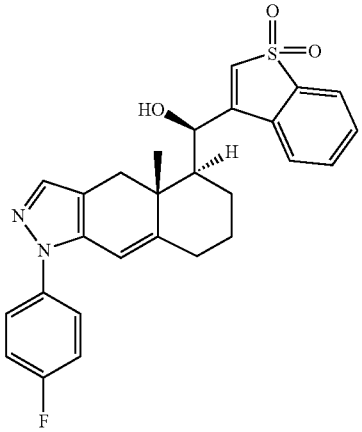

Example 212

Example 119 (11.0 mg, 0.026 mmol) was dissolved in THF (200 μL) and MeOH (200 μL) was added. The solution was cooled to 0° C. Oxone (32 mg, 0.051 mmol) was dissolved in H$_2$O (800 μL) and this solution was added to the solution of 119. The reaction was warmed to room temperature and stirred for 4 hours. At this point, additional oxone (32 mg, 0.051 mmol) was added as a solid. The reaction was stirred at room temperature for an additional 24 hours and then diluted with EtOAc (25 mL) and washed with water, saturated NaHCO$_3$, and brine (10 mL each). The organic layer was dried over Na$_2$SO$_4$, filtered, and concentrated. The residue was purified by preparatory thin layer chromatography (60% EtOAc/hexanes) to afford 2.5 mg (21%) of Example 212. R$_f$=0.13 (40% EtOAc/hexanes). LCMS=463; (M+1)$^+$. $^1$H NMR (CDCl$_3$, 500 MHz) δ 7.76 (d, J=7.5 Hz, 1H), 7.52-7.60 (m, 3H), 7.40-7.45 (m, 3H), 7.14 (t, J=8.5 Hz, 21), 6.72 (s, 1H), 6.14 (s, 1H), 5.02 (d, J=2.0 Hz, 1H), 2.89 (d, J=14.5 Hz, 1H), 2.65 (m, 1H), 2.55 (d, J=15 Hz, 1H), 2.37-2.45 (m, 2H), 2.28 (m, 1H), 1.96-2.14 (m, 3H), 1.14 (s, 3H).

Example 213

Example 213 was prepared in the same manner as example 212, starting from example 120.

Biological Assays

The activity of the compounds of the present invention as modulators of the glucocorticoid receptor can be evaluated using the following assays:

Ligand Binding Assays

For the hGRα ligand binding assay, cytosols were prepared from recombinant baculovirus expressed receptors. Frozen cell pellets were dounce homogenized in ice cold $KPO_4$ buffer (10 mM $KPO_4$, 20 mM sodium molybdate, 1 mM EDTA, 5 mM DTT and complete protease inhibitor tablets from Boehringer Mannheim) with a "B" plunger. The homogenates were centrifuged at 35,000×g for 1 h at 4° C. in a JA-20 rotor. The $IC_{50s}$ were determined by incubating the cytosols at a final concentration of 2.5 nM [1,2,4,6,7-$^3$H] Dexamethasone in the presence of increasing concentrations (10-11 to 10-6) of cold dexamethasone or the ligands at 4° C. for 24 h. Bound and free were separated by a gel filtration assay, (Geissler et al, personal communication). Half of the reaction was added to a gel filtration plate (MILLIPORE) containing sephadex G-25 beads that was previously equilibrated with KPO4 buffer containing 1 mg/ml BSA and centrifuged at 1000×g for 5 min. The reaction plate was centrifuged at 1000×g for 5 min. and the reactions were collected in a second 96-well plate and scintillation cocktail was added and counted in (Wallac) double coincidence beta counter. The $IC_{50s}$ were calculated using a 4-parameter fit program.

Compounds of the invention demonstrated an activity in the range of 0.1 nM to 1 μM in the assay procedure described above.

What is claimed is:

1. A compound which is:

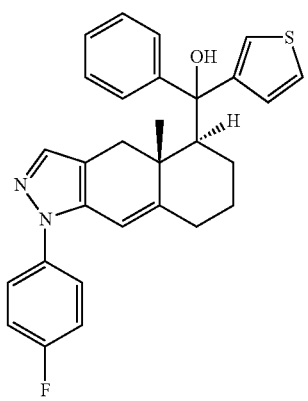

all possible diasteromers or a pharmaceutically acceptable salt thereof.

2. A compound selected from the following group:

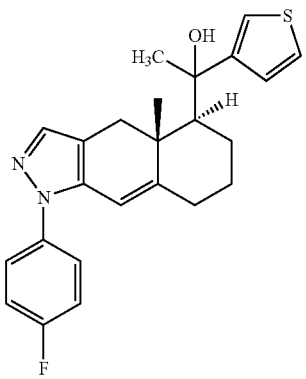

and all possible diasteromers

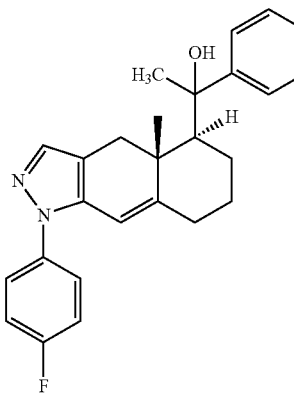

and all possible diasteromers

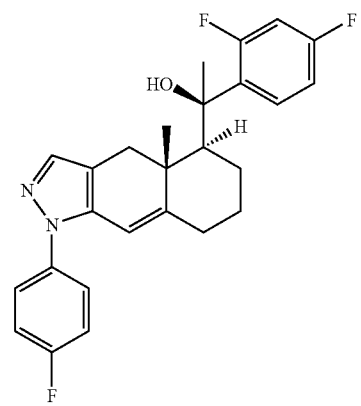

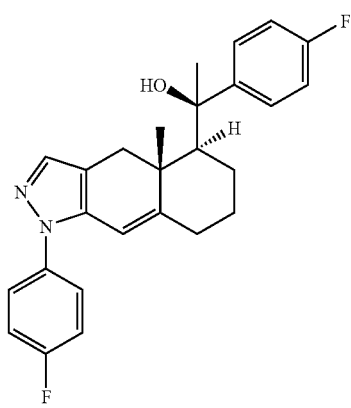
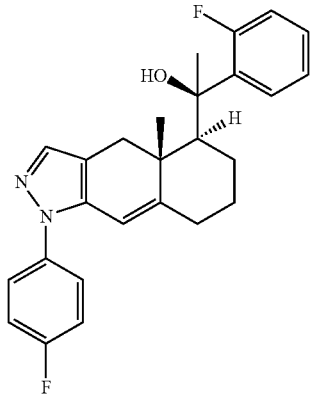
or a pharmaceutically acceptable salt of any of the foregoing compounds.
* * * * *